(12) United States Patent
Schulte et al.

(10) Patent No.: US 11,051,835 B2
(45) Date of Patent: Jul. 6, 2021

(54) ALIGNMENT FEATURES FOR ULTRASONIC SURGICAL INSTRUMENT

(71) Applicant: Ethicon LLC, Guaynabo, PR (US)

(72) Inventors: John B. Schulte, West Chester, OH (US); Craig N. Faller, Batavia, OH (US); Eric B. Smith, Cincinnati, OH (US); Patrick J. Scoggins, Loveland, OH (US); JoAnn M. Stegeman, Cincinnati, OH (US); Tylor C. Muhlenkamp, Cincinnati, OH (US); William D. Dannaher, Cincinnati, OH (US); Michael R. Lamping, Cincinnati, OH (US); Jacob S. Gee, Cincinnati, OH (US); William B. Weisenburgh, II, Maineville, OH (US); Brian D. Bertke, Fort Thomas, KY (US)

(73) Assignee: Cilag GmbH International, Zug (CH)

(*) Notice: Subject to any disclaimer, the term of this patent is extended or adjusted under 35 U.S.C. 154(b) by 202 days.

(21) Appl. No.: 16/209,048

(22) Filed: Dec. 4, 2018

(65) Prior Publication Data
US 2019/0167288 A1 Jun. 6, 2019

Related U.S. Application Data

(62) Division of application No. 14/031,665, filed on Sep. 19, 2013, now abandoned.

(51) Int. Cl.
*A61B 17/28* (2006.01)
*A61B 17/285* (2006.01)
(Continued)

(52) U.S. Cl.
CPC ........ *A61B 17/2816* (2013.01); *A61B 17/285* (2013.01); *A61B 2017/2825* (2013.01);
(Continued)

(58) Field of Classification Search
CPC .... A61B 17/320068; A61B 17/320092; A61B 17/32002; A61B 17/320032;
(Continued)

(56) References Cited

U.S. PATENT DOCUMENTS 5,322,055 A 6/1994 Davison et al.
5,324,299 A 6/1994 Davison et al.
(Continued)

FOREIGN PATENT DOCUMENTS

JP 2000-254138 A 9/2000
JP 2009-514566 A 4/2009
(Continued)

OTHER PUBLICATIONS

Chinese Office Action dated Jan. 29, 2018 for Application No. 20148000036.2, 8 pgs.
(Continued)

*Primary Examiner* — Melanie R Tyson
*Assistant Examiner* — Chima U Igboko
(74) *Attorney, Agent, or Firm* — Frost Brown Todd LLC

(57) ABSTRACT

An ultrasonic instrument comprises a body, a shaft assembly, an ultrasonic blade, and a pivoting member. The shaft assembly extends distally from the body. The ultrasonic blade is positioned distal to the shaft assembly. The pivoting member is pivotable with respect to the blade from an open position to a closed position to thereby clamp tissue between the pivoting member and the blade. One or both of the shaft assembly or the pivoting member comprise a guide feature. The guide feature is configured to provide lateral alignment of the distal portion of the pivoting member with the blade as the pivoting member is pivoted to the closed position.

13 Claims, 56 Drawing Sheets

(51) Int. Cl.
*A61B 17/32* (2006.01)
*A61B 17/29* (2006.01)

(52) U.S. Cl.
CPC .............. *A61B 2017/2929* (2013.01); *A61B 2017/2945* (2013.01); *A61B 2017/320093* (2017.08); *A61B 2017/320094* (2017.08); *A61B 2017/320095* (2017.08)

(58) Field of Classification Search
CPC ......... A61B 2017/320069; A61B 2017/32007; A61B 2017/320071; A61B 2017/320072; A61B 2017/320073; A61B 2017/320074; A61B 2017/320075; A61B 2017/320077; A61B 2017/320078; A61B 2017/32008; A61B 2017/320082; A61B 2017/320084; A61B 2017/320088; A61B 2017/320089; A61B 2017/32009; A61B 2017/320093; A61B 2017/320094; A61B 2017/320095; A61B 2017/320097; A61B 2017/320098; A61B 10/02; A61B 10/0233; A61B 10/0241; A61B 10/025; A61B 10/0266; A61B 10/0275; A61B 10/0283; A61B 10/0291; A61B 10/04; A61B 2010/0208; A61B 2010/0258; A61B 2010/045
See application file for complete search history.

(56) References Cited

U.S. PATENT DOCUMENTS

| | | | |
|---|---|---|---|
| 5,507,773 A * | 4/1996 | Huitema | A61B 17/07207 |
| | | | 600/564 |
| 5,873,873 A * | 2/1999 | Smith | A61B 17/320092 |
| | | | 606/1 |
| 5,980,510 A | 11/1999 | Tsonton et al. | |
| 6,325,811 B1 | 12/2001 | Messerly | |
| 6,773,444 B2 | 8/2004 | Messerly | |
| 6,783,524 B2 | 8/2004 | Anderson et al. | |
| 8,461,744 B2 | 6/2013 | Wiener et al. | |
| 8,591,536 B2 | 11/2013 | Robertson | |
| 8,623,027 B2 | 1/2014 | Price et al. | |
| 9,084,878 B2 | 7/2015 | Kawaguchi et al. | |
| 9,095,367 B2 | 8/2015 | Olson et al. | |
| 2005/0177177 A1 | 8/2005 | Viola | |
| 2006/0079874 A1 | 4/2006 | Faller et al. | |
| 2007/0043352 A1* | 2/2007 | Garrison | A61B 17/285 |
| | | | 606/51 |
| 2007/0191713 A1* | 8/2007 | Eichmann | A61B 17/320092 |
| | | | 600/471 |
| 2007/0282333 A1 | 12/2007 | Fortson et al. | |
| 2008/0200940 A1 | 8/2008 | Eichmann et al. | |
| 2010/0069940 A1 | 3/2010 | Miller et al. | |
| 2011/0087212 A1 | 4/2011 | Aldridge et al. | |
| 2011/0251609 A1* | 10/2011 | Johnson | A61B 17/3205 |
| | | | 606/46 |
| 2012/0078248 A1 | 3/2012 | Worrell et al. | |
| 2012/0112687 A1 | 5/2012 | Houser et al. | |
| 2012/0116265 A1 | 5/2012 | Houser et al. | |
| 2014/0005701 A1 | 1/2014 | Olson et al. | |
| 2015/0080925 A1 | 3/2015 | Schulte et al. | |
| 2016/0157928 A1 | 6/2016 | Eshkol et al. | |

FOREIGN PATENT DOCUMENTS

| | | |
|---|---|---|
| JP | 2011-235119 A | 11/2011 |
| JP | 2012-501805 A | 1/2012 |
| JP | 2012-531970 A | 12/2012 |
| WO | WO 2003/086207 A1 | 10/2003 |
| WO | WO 2007/047380 A2 | 4/2007 |
| WO | WO 2014/001200 A1 | 1/2014 |
| WO | WO 2013/062103 A1 | 4/2015 |

OTHER PUBLICATIONS

European Examination Report dated Sep. 29, 2017 for Application No. 14771676.5, 5 pgs.
Japanese Notification of Reason for Refusal dated May 29, 2018 for Application No. 2016-515402, 4pgs.
Japanese Search Report dated May 31, 2018 for Application No. 2016-515402, 21 pgs.
Japanese Decision of Reason for Refusal dated Dec. 30, 2018 for Application No. 2016-515402, 1 pg.
International Search Report and Written Opinion dated Mar. 13, 2015 for Application No. PCT/US2014/053842, 14 pgs.
U.S. Appl. No. 61/410,603, filed Nov. 5, 2010.
Brazilian Search Report dated Feb. 17, 2020 for Application No. BR 112016005855-0, 4 pgs.
European Examination Report dated Oct. 1, 2020 for Application No. EP 14771676.5, 5 pgs.
Indian Examination Report dated Sep. 23, 2020 for Application No. IN 201617011025, 6 pgs.

* cited by examiner

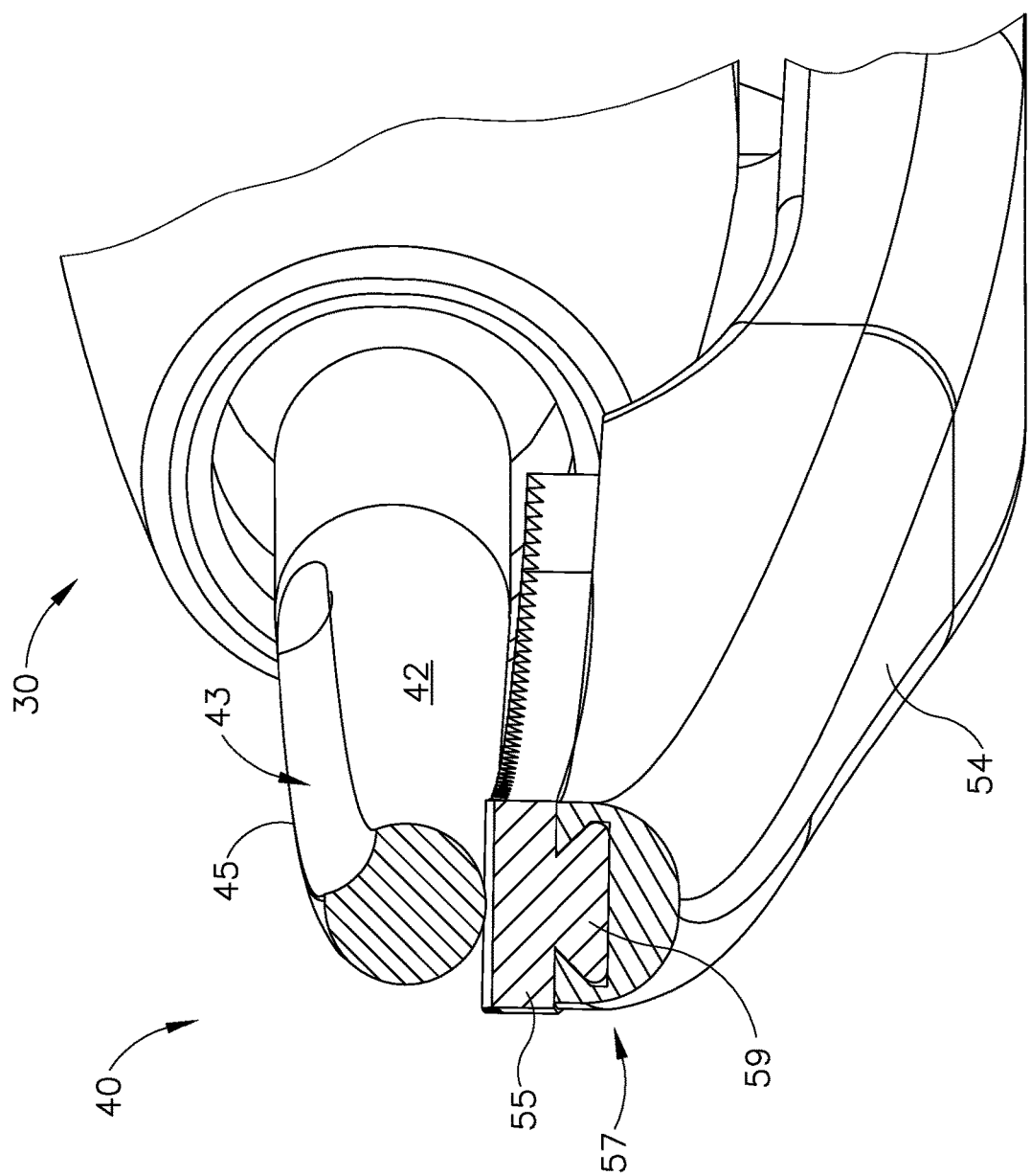

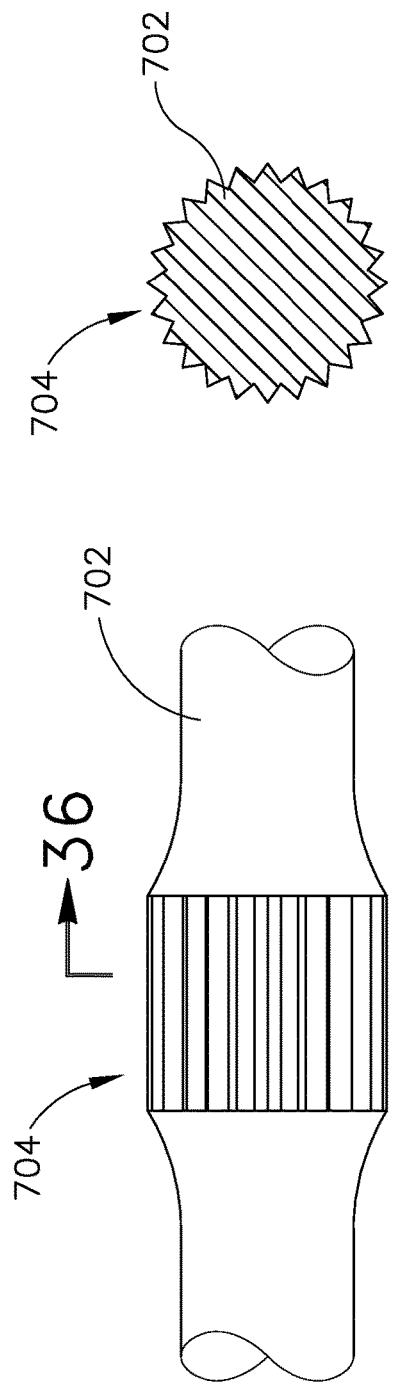
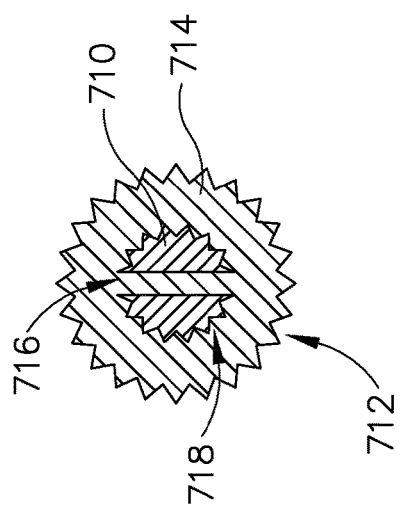
Fig.35
Fig.36
Fig.37

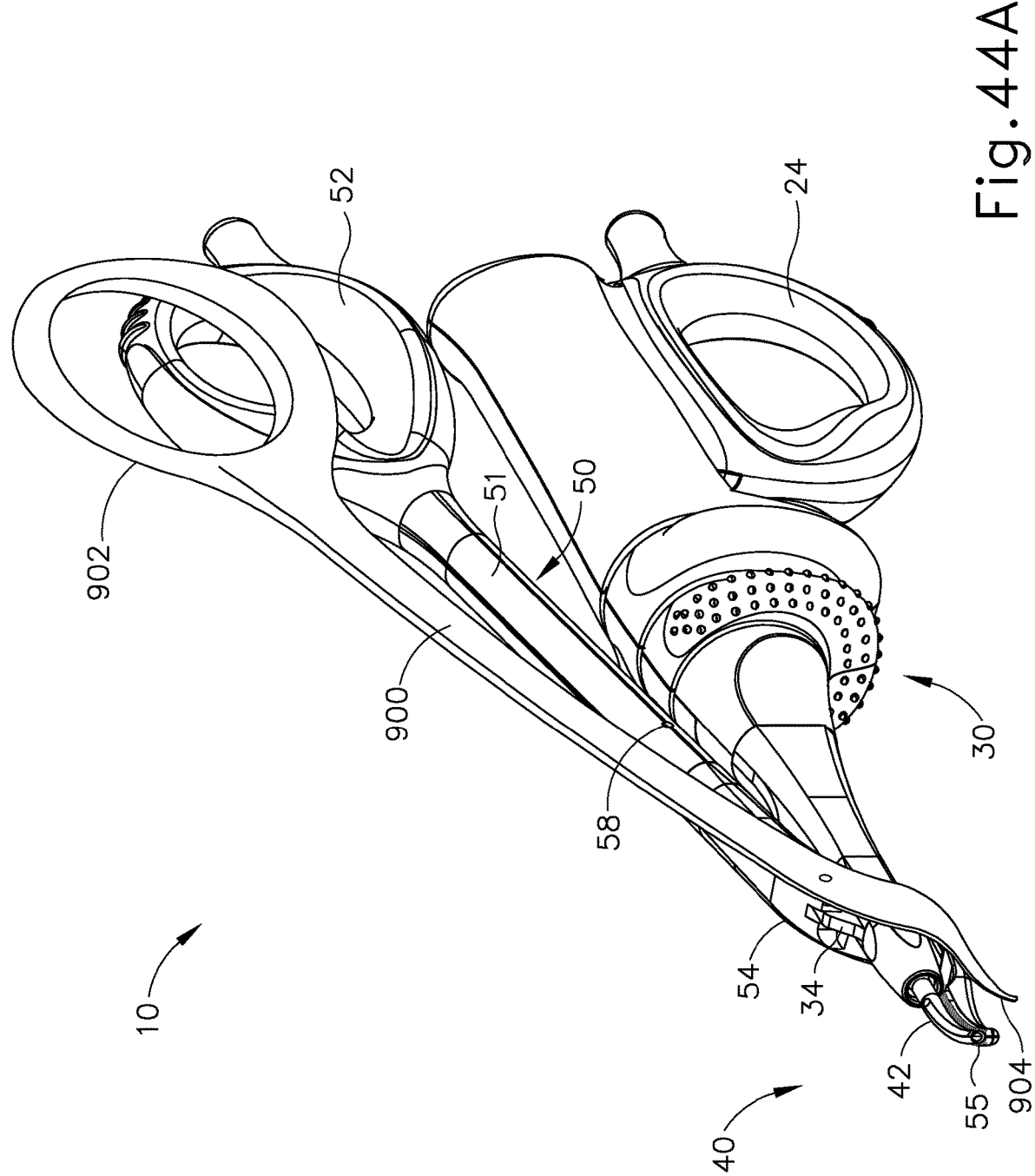

ALIGNMENT FEATURES FOR ULTRASONIC SURGICAL INSTRUMENT

This application is a division of U.S. application Ser. No. 14/031,665, filed Sep. 19, 2013, entitled "Alignment Features for Ultrasonic Surgical Instrument," published as U.S. Pub. No. 2015/0080925 on Mar. 19, 2015, now abandoned.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the surgeon's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,028 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, issued as U.S. Pat. No. 9,393,037 on Jul. 19, 2016, entitled "Surgical Instruments with Articulating Shafts," the disclosure of which is incorporated by reference herein; and U.S. patent application Ser. No. 13/657,553, filed Oct. 22, 2012, issued as U.S. Pat. No. 9,095,367 on Aug. 4, 2015, entitled "Flexible Harmonic Waveguides/Blades for Surgical Instruments," the disclosure of which is incorporated by reference herein.

Some ultrasonic surgical instruments may include a clamp feature to press tissue against the ultrasonic blade of the end effector. Examples of such an arrangement (sometimes referred to as a clamp coagulator shears or an ultrasonic transector) is disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; and U.S. Pat. No. 6,325,811, entitled "Blades with Functional Balance Asymmetries for use with Ultrasonic Surgical Instruments," issue Dec. 4, 2001, the disclosure of which is incorporated by reference herein. Some versions of clamp coagulator shears utilize handles that are either of a pistol or scissors grips design. The scissor grip designs may have one thumb or finger grip that is immovable and fixed to the housing; and one movable thumb or finger grip. Some designs have scissor arms that extend from the grips, with one of the arms rotating around a fixed pivot or rotation point that is perpendicular to the longitudinal axis of the working element. The operator may thus squeeze a handgrip or other feature to drive a clamp arm, to thereby press the clamp pad toward the blade.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6 depicts a cross-sectional view of the end effector of FIG. 4 taken along line 6-6 of FIG. 5;

FIG. 35 depicts a side elevational view of a portion of an exemplary waveguide for use in the instrument of FIG. 1;

FIG. 36 depicts a cross-sectional view of the waveguide of FIG. 35 taken along line 36-36 of FIG. 35;

FIG. 37 depicts a cross-sectional view of an exemplary alternative configuration for the waveguide of FIG. 35 taken along line 36-36 of FIG. 35;

FIG. 44A depicts a perspective view of an exemplary alternative ultrasonic surgical instrument with a cutting member in an open position;

Figure 1:
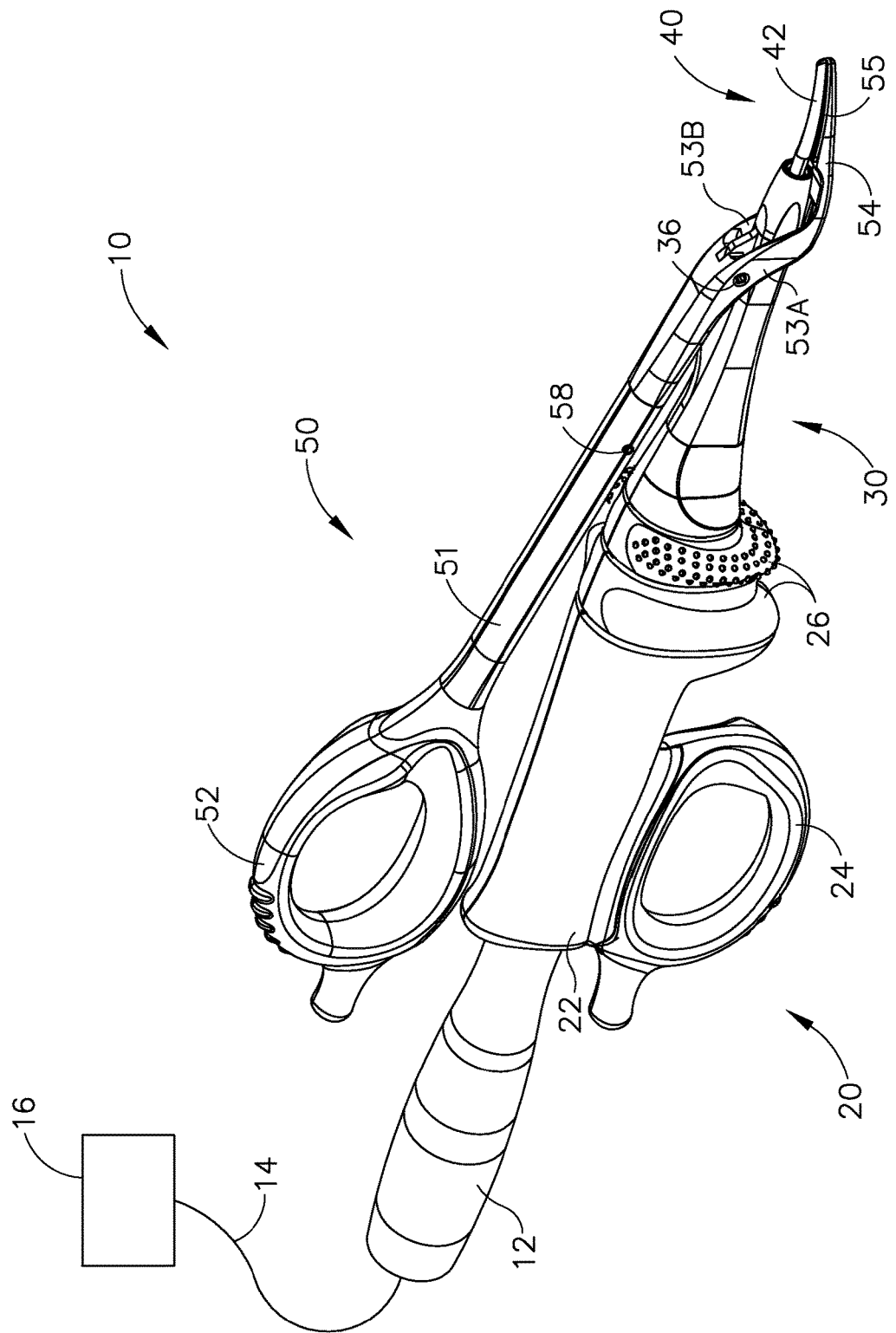
FIG. 1 depicts a perspective view of an ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Ultrasonic Surgical Instrument

FIG. 1 illustrates an exemplary ultrasonic surgical instrument (10). At least part of instrument (10) may be constructed and operable in accordance with at least some of the teachings of U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. patent application Ser. No. 13/538,588, issued as U.S. Pat. No. 9,393,037 on Jul. 19, 2016; U.S. patent application Ser. No. 13/657,553, issued as U.S. Pat. No. 9,095,367 on Aug. 4, 2015; and/or U.S. Pat. App. No. 61/410,603. The disclosures of each of the foregoing patents, publications, and applications are incorporated by reference herein. As described therein and as will be described in greater detail below, instrument (10) is operable to cut tissue and seal or weld tissue (e.g., a blood vessel, etc.) substantially simultaneously, using a combination of compression and ultrasonic vibrational energy. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Figure 3:
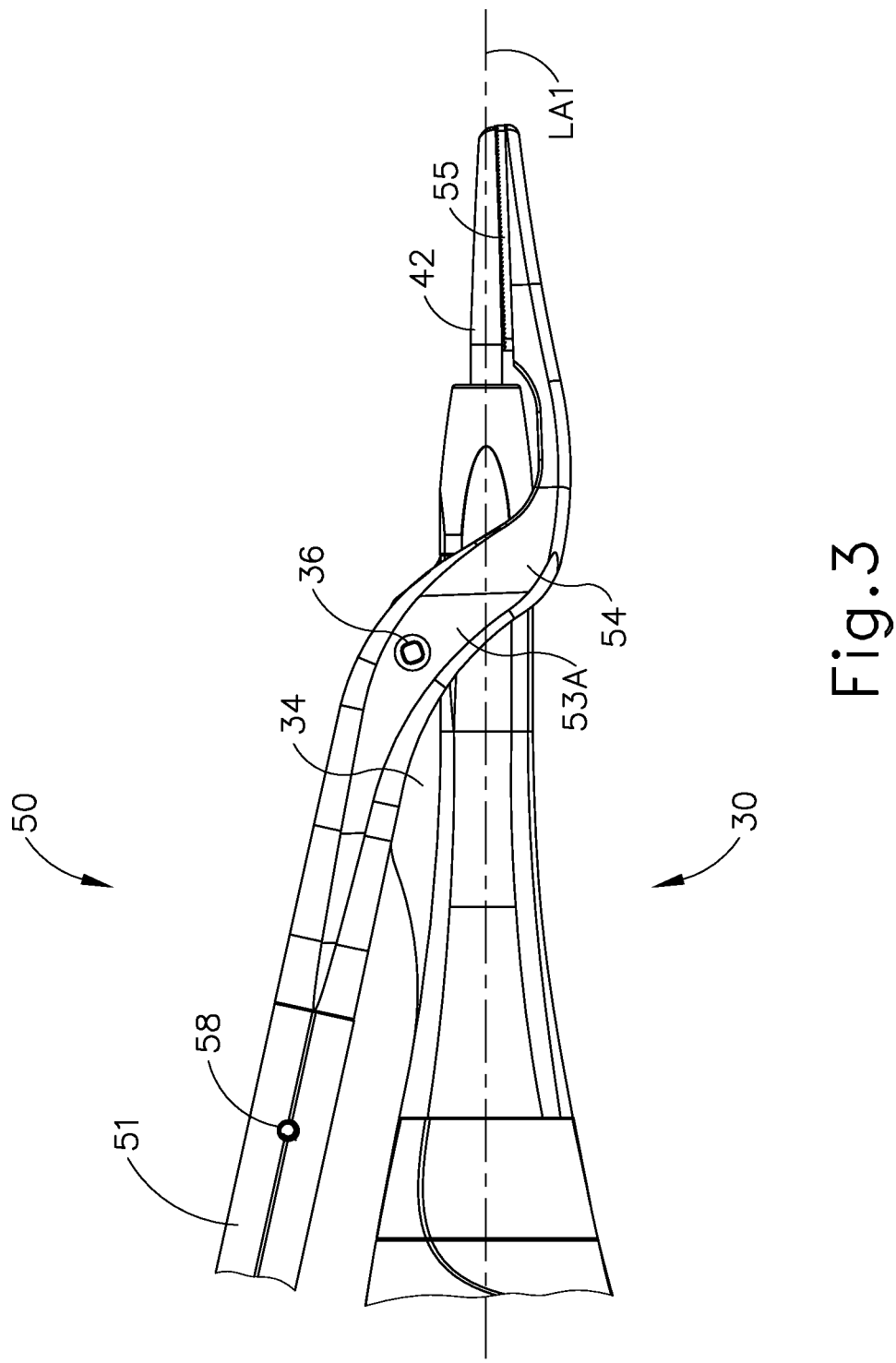
FIG. 3 depicts a side elevational view of the distal end of the instrument of FIG. 1.

Instrument (10) of the present example comprises a handpiece (20), a shaft assembly (30), and an end effector (40). Handpiece (20) comprises a body (22) including a finger grip (24) and a pair of buttons (26). Instrument (10) also includes a clamp arm assembly (50) that is pivotable toward and away from body (22). A proximal portion of clamp arm assembly (50) comprises a thumb grip (52). Thumb grip (52) and finger grip (24) together provide a scissor grip type of configuration. It should be understood, however, that various other suitable configurations may be used, including but not limited to a pistol grip configuration. End effector (40) includes an ultrasonic blade (42) extending distally from shaft assembly (30); and a pivoting clamp arm (54), which is an integral feature of clamp arm assembly (50). Clamp arm assembly (50) is pivotably coupled to a projection (34) extending laterally from shaft assembly (30) via a pivot member (36) (e.g., a pin, bearing, shaft, etc.)=such that clamp arm (54) is pivotable toward and away from ultrasonic blade (42) to thereby clamp tissue between a clamp pad (55) of clamp arm (54) and ultrasonic blade (42). As best seen in FIG. 3, clamp arm assembly (50) is pivotably coupled to projection (34) such that clamp arm assembly (50) pivots about an axis offset from a longitudinal axis (LA1). It should be understood that such rotation about an offset axis may allow for a narrower shaft assembly (30) profile. It should be understood that shaft assembly (30) passes through a portion of clamp arm assembly (50) such that as clamp arm assembly (50) rotates, clamp arm (54) rotates about a portion of shaft assembly (30). In particular, a first member (53A) and a second member (53B) of clamp arm assembly (50) are disposed about a distal portion of shaft assembly (30).

Figure 2:
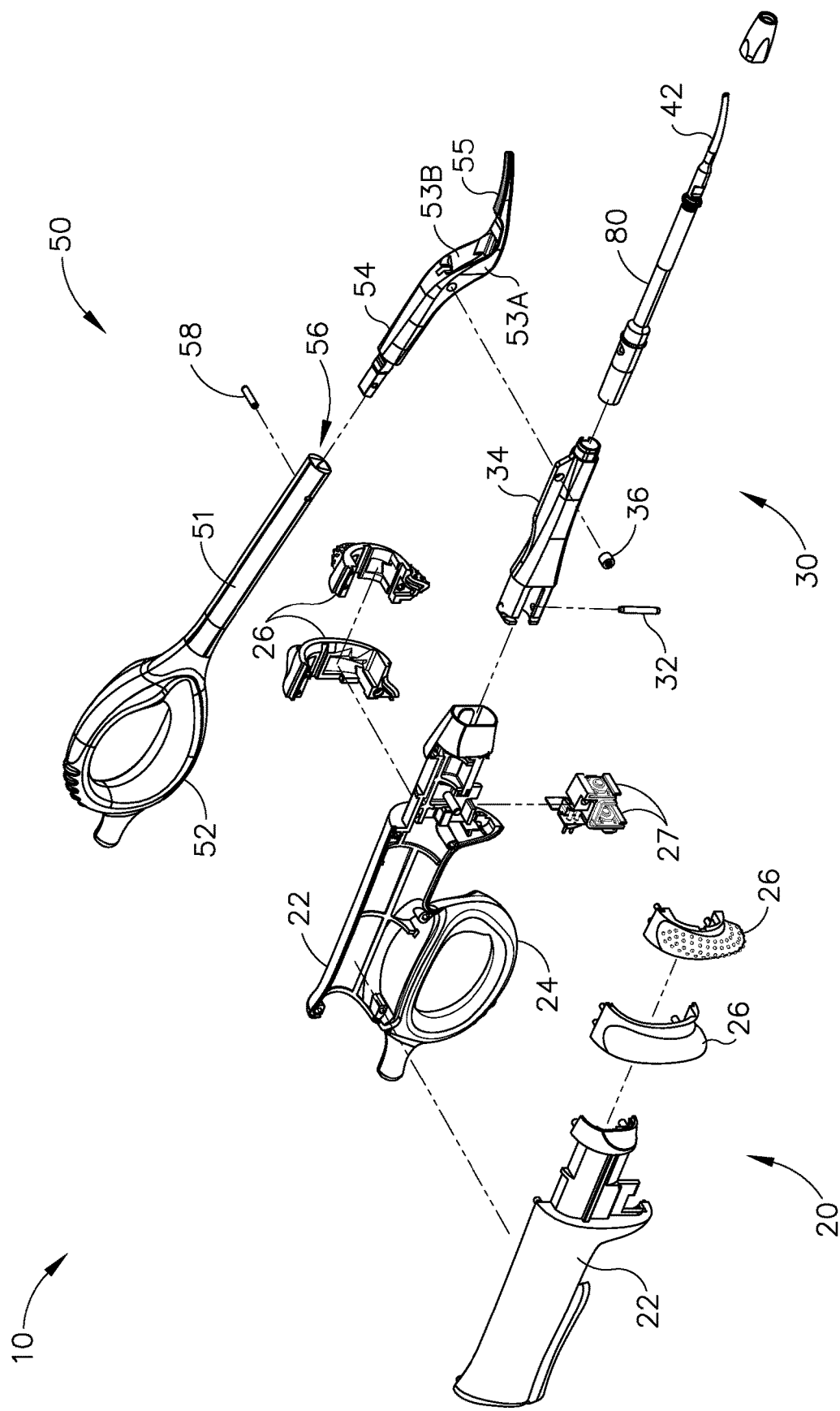
FIG. 2 depicts an exploded perspective view of the instrument FIG. 1.

Clamp arm assembly (50) is configured such that clamp arm (54) is pivotable toward ultrasonic blade (42) in response to pivoting of thumb grip (52) of clamp arm assembly (50) toward body (22); and such that clamp arm (54) is pivotable away from ultrasonic blade (42) in response to pivoting of thumb grip (52) of clamp arm assembly (50) away from body (22). As best seen in FIG. 2, a proximal end of clamp arm (54) is disposed within a distal recess (56) of a shank portion (51) of clamp arm assembly (50); and is secured therein by a pin (58). Various other suitable ways in which clamp arm (54) may be integrated into clamp arm assembly (50) will be apparent to those of ordinary skill in the art in view of the teachings herein. In some versions, one or more resilient members are used to bias clamp arm (54) and/or trigger (28) to the open position shown in FIG. 1. By way of example only, such a resilient member may comprise a leaf spring, a torsion spring, and/or any other suitable kind of resilient member.

Figure 4:
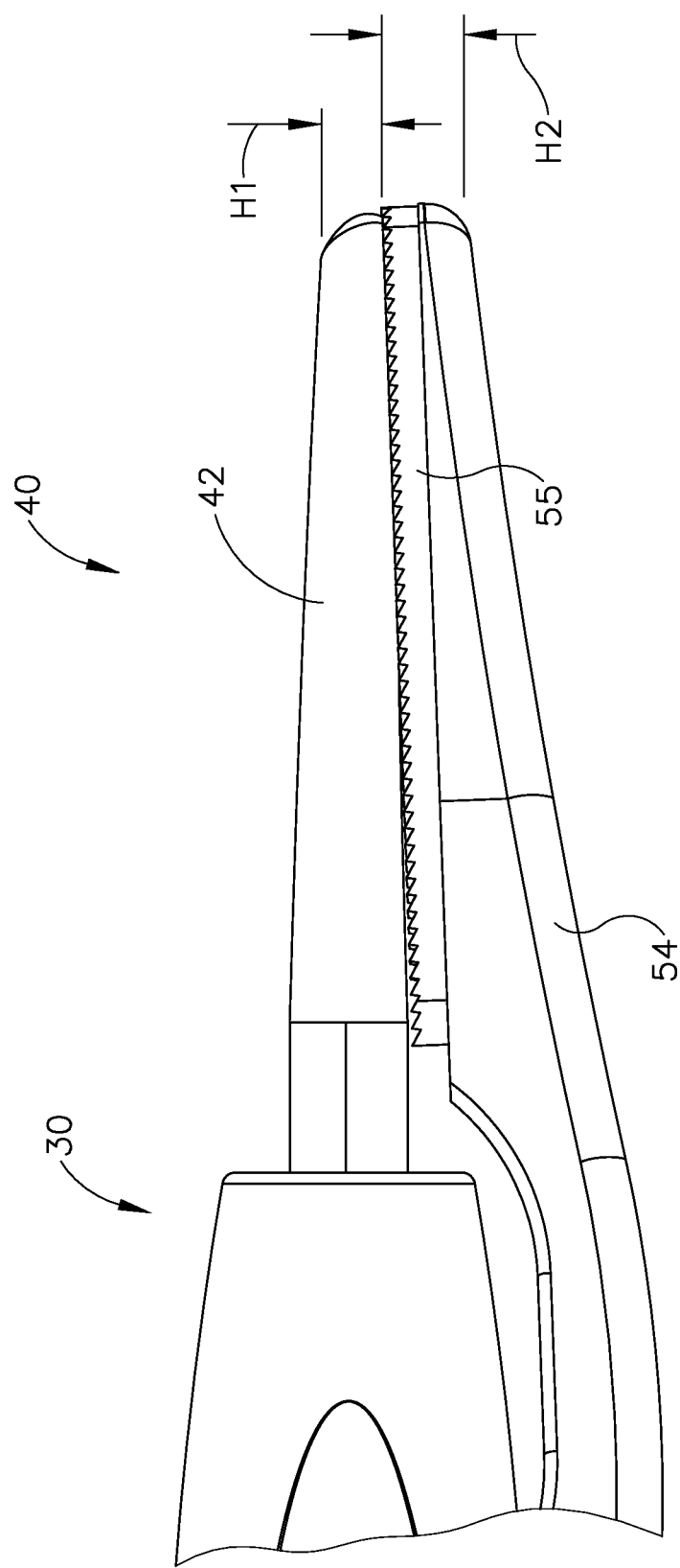
FIG. 4 depicts a side elevational view of an end effector of the instrument of FIG. 1.

FIG. 4 shows a side elevational view of end effector (40). A distal end of ultrasonic blade (42) has a height (H1). Height (H1) of the present example is approximately 0.057 inches. A distal end of clamp arm (54) has a height (H2). Height (H2) of the present example is approximately 0.067 inches. A ratio of height (H1) of ultrasonic blade (42) to height (H2) of clamp arm (54) in the present example is therefore approximately 0.85. Although height (H1) of ultrasonic blade (42) of the present example is approximately 0.057 inches, it should be understood that any other suitable value may be selected for height (H1). Furthermore, although height (H2) of clamp arm (54) of the present example is approximately 0.067 inches, it should be understood that any other suitable value may be selected for height (H2) (e.g., less than approximately 0.070 inches). Thus, it should be understood that the ratio of height (H1) of ultrasonic blade (42) to height (H2) of clamp arm (54) may be any other suitable ratio. By way of example only, the ratio of height (H1) of ultrasonic blade (42) to height (H2) of clamp arm (54) may be any ratio from approximately 0.50 to approximately 1.00, or more particularly between approximately 0.80 and approximately 1.00. It should also be understood that the distal tips of blade (42) and arm (54) are atraumatic in the present example. The dimensions, ratios, and/or atraumatic configurations of blade (42) and arm (54) may facilitate use of blade (42, 54) to together perform blunt dissections, move tissue structures without piercing those structures, etc.

Figure 5:
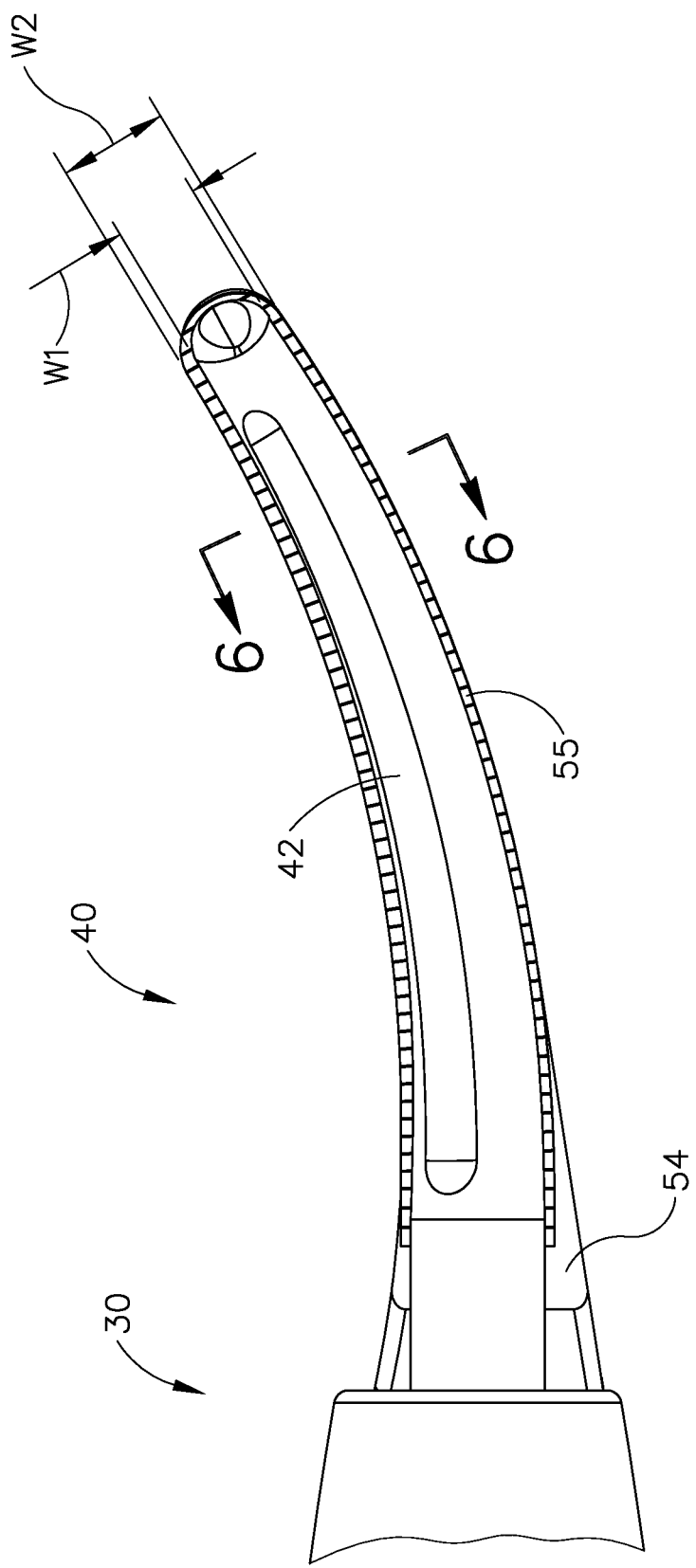
FIG. 5 depicts a top plan view of the end effector of FIG. 4.

FIG. 5 shows a top view of end effector (40). The distal end of ultrasonic blade (42) has a width (W1). Width (W1) of the present example is approximately 0.057 inches. The distal end of clamp arm (54) has a width (W2). Width (W2) of the present example is approximately 0.078 inches. A ratio of width (W1) of ultrasonic blade (42) to width (W2) of clamp arm (54) in the present example is therefore approximately 0.73. Although width (W1) of ultrasonic blade (42) of the present example is approximately 0.057 inches, it should be understood that any other suitable value may be selected for width (W1). Furthermore, although width (W2) of clamp arm (54) of the present example is approximately 0.078 inches, it should be understood that any other suitable value may be selected for width (W2) (e.g., less than approximately 0.065 inches). Thus, it should be understood that the ratio of width (W1) of ultrasonic blade (42) to width (W2) of clamp arm (54) may be any other suitable ratio. By way of example only, the ratio of width (W1) of ultrasonic blade (42) to width (W2) of clamp arm (54) may be any ratio from approximately 0.50 to approximately 1.00, or more particularly between approximately 0.65 and approximately 1.00. Such a ratio of widths (W1, W2) may promote alignment of blade (42) and arm (54) during sealing of vessels and tissue transection.

FIG. 6 shows a cross-sectional view of end effector (40). An interior face of clamp arm (54) presents a channel (57), which has a dovetail-shaped profile. Clamp pad (55) comprises a projection (59) that is shaped to complement the dovetail-shaped channel (57), such that channel (57) is configured to selectively receive and secure projection (59). It should therefore be understood that clamp pad (55) is configured to be selectively secured within channel (57) of clamp arm (54). It should also be understood that the dovetail-shaped retention feature of channel (57) may allow for a narrower clamp arm (54). Of course, any other suitable features or techniques may be used to secure clamp pad (55) to clamp arm (54).

As shown in FIG. 1, an ultrasonic transducer assembly (12) extends proximally from body (22) of handpiece (20). Transducer assembly (12) is coupled with a generator (16) via a cable (14). Transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (16) may be integrated into handpiece (20), and that handpiece (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

Ultrasonic vibrations that are generated by transducer assembly (12) are communicated along an acoustic waveguide (80), which extends through shaft assembly (30) to reach ultrasonic blade (42) as shown in FIG. 2. Waveguide (80) is secured within shaft assembly (30) via a pin (32), which passes through waveguide (80) and shaft assembly (30). Pin (32) is located at a position along the length of waveguide (80) corresponding to a node associated with resonant ultrasonic vibrations communicated through waveguide (80). As noted above, when ultrasonic blade (42) is in an activated state (i.e., vibrating ultrasonically), ultrasonic blade (42) is operable to effectively cut through and seal tissue, particularly when the tissue is being clamped between clamp arm (54) and ultrasonic blade (42). It should be understood that waveguide (80) may be configured to amplify mechanical vibrations transmitted through waveguide (80). Furthermore, waveguide (80) may include features operable to control the gain of the longitudinal vibrations along waveguide (80) and/or features to tune waveguide (80) to the resonant frequency of the system.

In the present example, the distal end of ultrasonic blade (42) is located at a position corresponding to an anti-node associated with resonant ultrasonic vibrations communicated through waveguide (80), in order to tune the acoustic assembly to a preferred resonant frequency $f_o$ when the acoustic assembly is not loaded by tissue. When transducer assembly (12) is energized, the distal end of ultrasonic blade (42) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through the waveguide to reach ultrasonic blade (42), thereby providing oscillation of ultrasonic blade (42) at the resonant ultrasonic frequency. Thus, when tissue is secured between ultrasonic blade (42) and clamp arm (54), the ultrasonic oscillation of ultrasonic blade (42) may simultaneously sever the tissue and denature the proteins in adjacent tissue cells, thereby providing a coagulative effect with relatively little thermal spread. In some versions, an electrical current may also be provided through ultrasonic blade (42) and clamp arm (54) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

An operator may activate buttons (26) to selectively close switches (27) (see FIG. 2), thereby selectively activating transducer assembly (12) to activate ultrasonic blade (42). In the present example, two buttons (26) are provided—one for activating ultrasonic blade (42) at a low power and another for activating ultrasonic blade (42) at a high power. However, it should be understood that any other suitable number of buttons and/or otherwise selectable power levels may be provided. For instance, a foot pedal may be provided to selectively activate transducer assembly (12). Buttons (26) of the present example are positioned such that an operator may readily fully operate instrument (10) with a single hand. For instance, the operator may position their thumb in the ring formed by thumb grip (52), position their middle or ring finger in the ring formed by finger grip (24), and manipulate buttons (26) using their index finger. Of course, any other suitable techniques may be used to grip and operate instrument (10); and buttons (26) may be located at any other suitable positions.

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, abandoned; U.S. Pub. No. 2008/0200940, now abandoned; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. patent application Ser. No. 13/538,588, issued as U.S. Pat. No. 9,393,037 on Jul. 19, 2016; and/or U.S. patent application Ser. No. 13/657,553, issued as U.S. Pat. No. 9,095,367 on Aug. 4, 2015. Additional merely illustrative variations for instrument (10) will be described in greater detail below. It should be understood that the below described variations may be readily applied to instrument (10) described above and any of the instruments referred to in any of the references that are cited herein, among others.

II. Exemplary Clamp Arm Alignment Features

It may be desirable to provide features that guide clamp arm (54) such that clamp arm (54) and/or clamp pad (55) adequately and appropriately engage ultrasonic blade (42) as clamp arm (54) is pivoted toward ultrasonic blade (42). In particular, it may be desirable to ensure that the center (width-wise) of clamp pad (55) is aligned with the center (width-wise) of ultrasonic blade (42) along a common vertical plane as clamp arm (54) is pivoted toward ultrasonic blade (42). An example of such alignment is shown in FIG. 5, where clamp pad (55) and ultrasonic blade (42) are laterally aligned/centered relative to each other. Such alignment may also include proper angular positioning of clamp pad (55) (e.g., about a longitudinal axis defined by clamp arm (54)) in relation to ultrasonic blade (42). The following examples include various features that may be used to guide clamp arm (54) into alignment with ultrasonic blade (42); or to otherwise maintain alignment between clamp arm (54) and ultrasonic blade (42). It should be understood that the following alignment/guide features may be readily incorporated into instrument (10) described above. It should also be understood that the following alignment/guide features are configured to guide clamp arm (54) into alignment along a lateral plane that is perpendicular to the plane along which clamp arm (54) pivots to close clamp pad (55) against ultrasonic blade (42). In some instances, this lateral plane along which clamp arm is guided (54) intersects the plane along which clamp arm pivots (54) at the longitudinal axis of shaft assembly (30).

A. First Exemplary Guide Feature

Figure 7A:
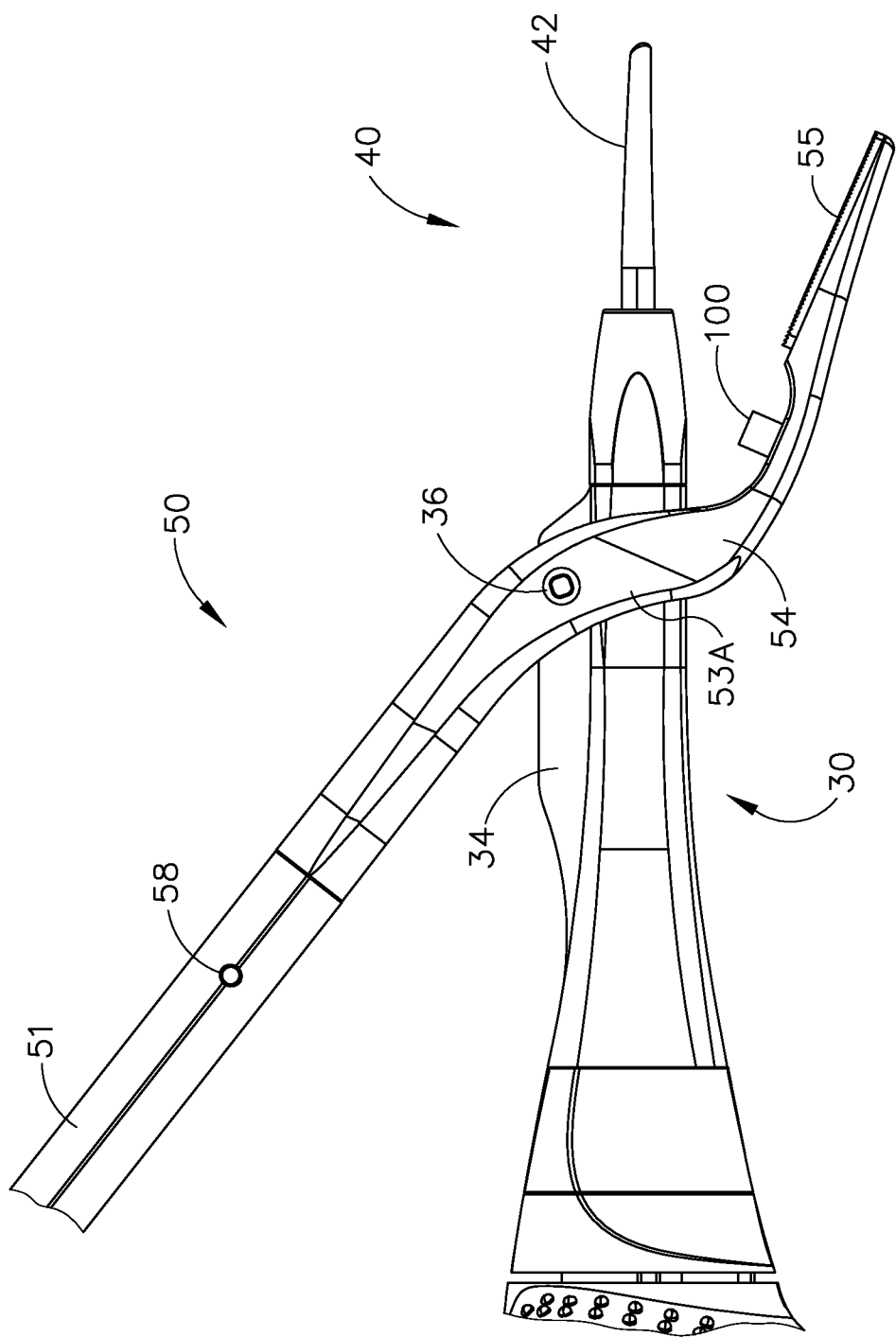
FIG. 7A depicts a side elevational view of a version of the distal end of the instrument of FIG. 1 with exemplary guide features, in an open position.
Figure 7B:
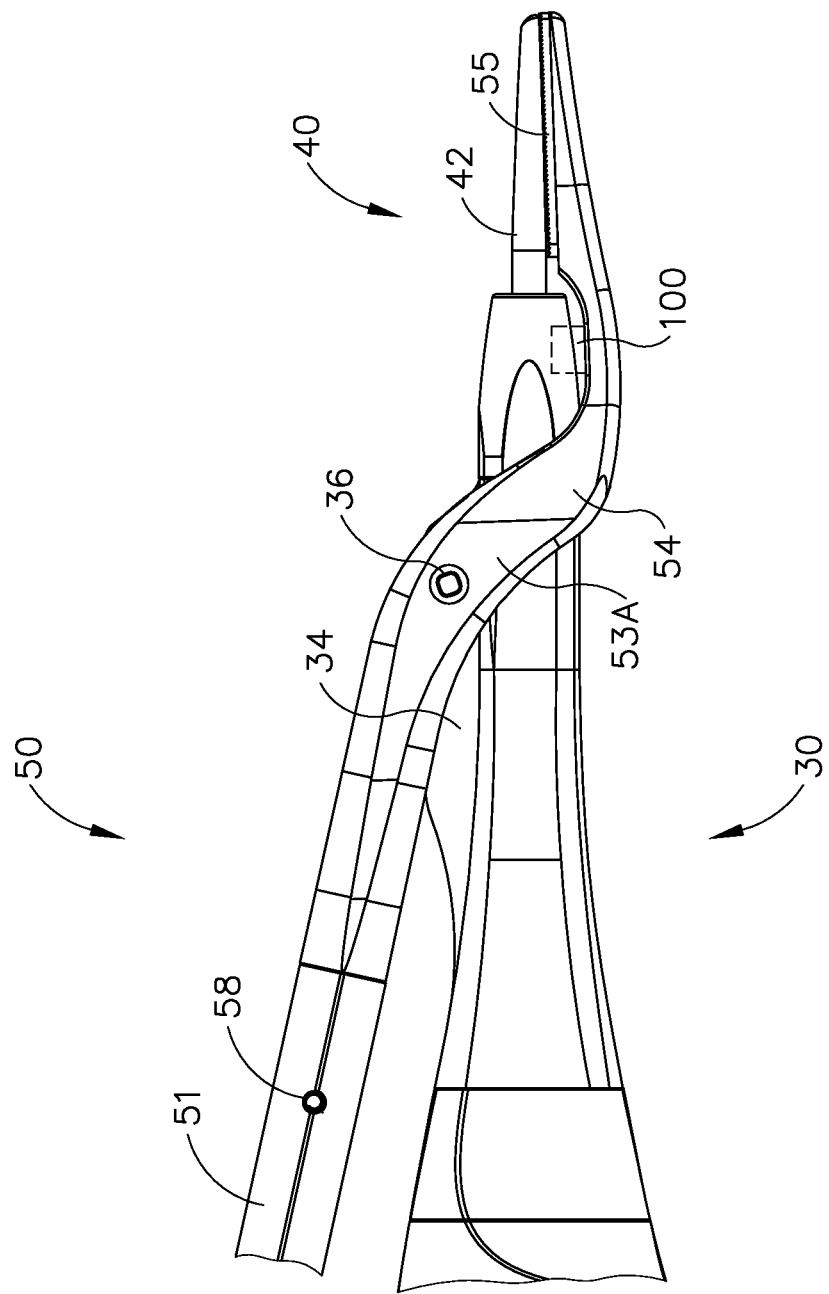
FIG. 7B depicts a side elevational view of the distal end configuration of FIG. 7A, in a closed position.
Figure 8A:
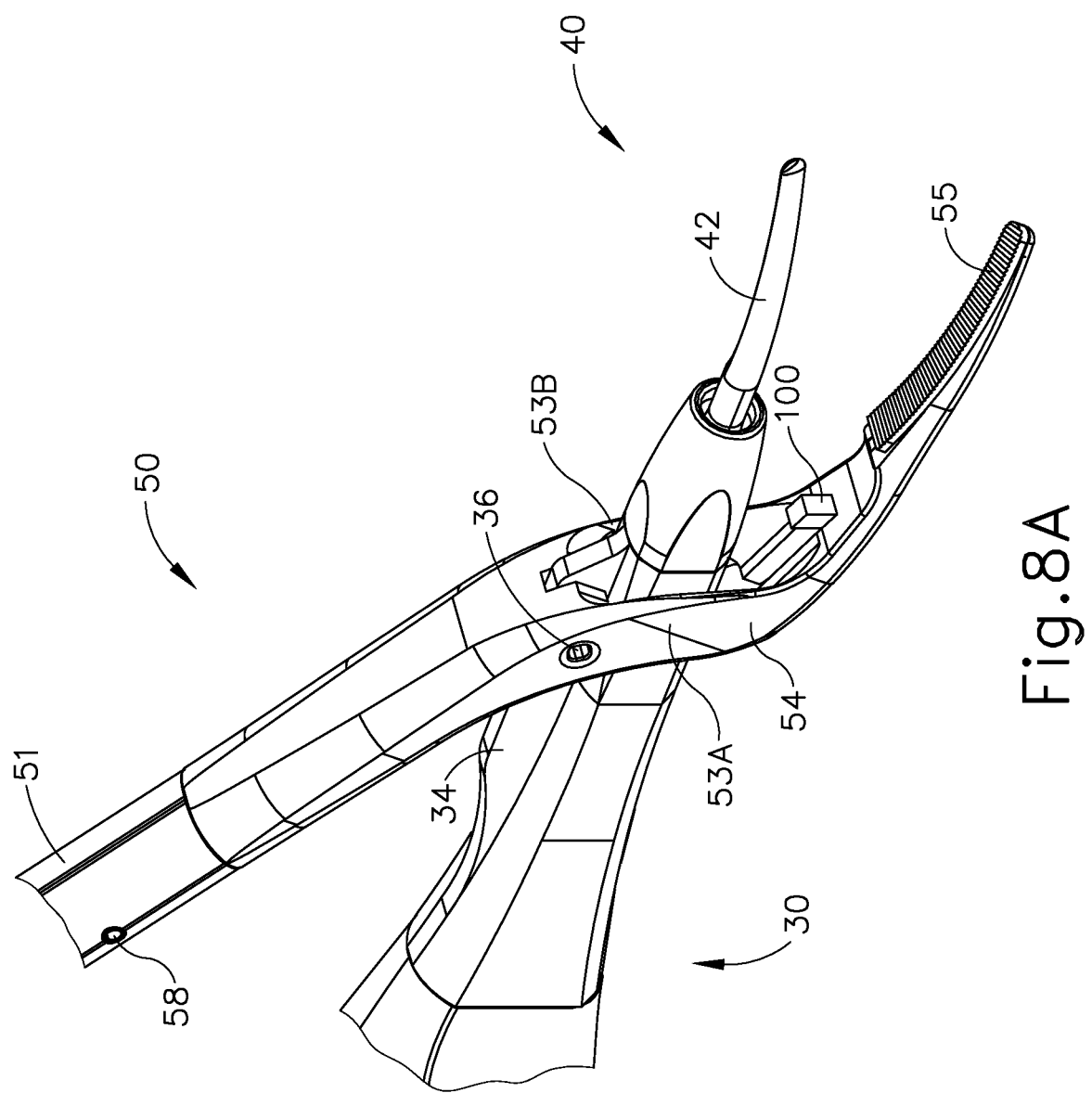
FIG. 8A depicts a perspective view of the distal end configuration of FIG. 7A, in the open position.
Figure 8B:
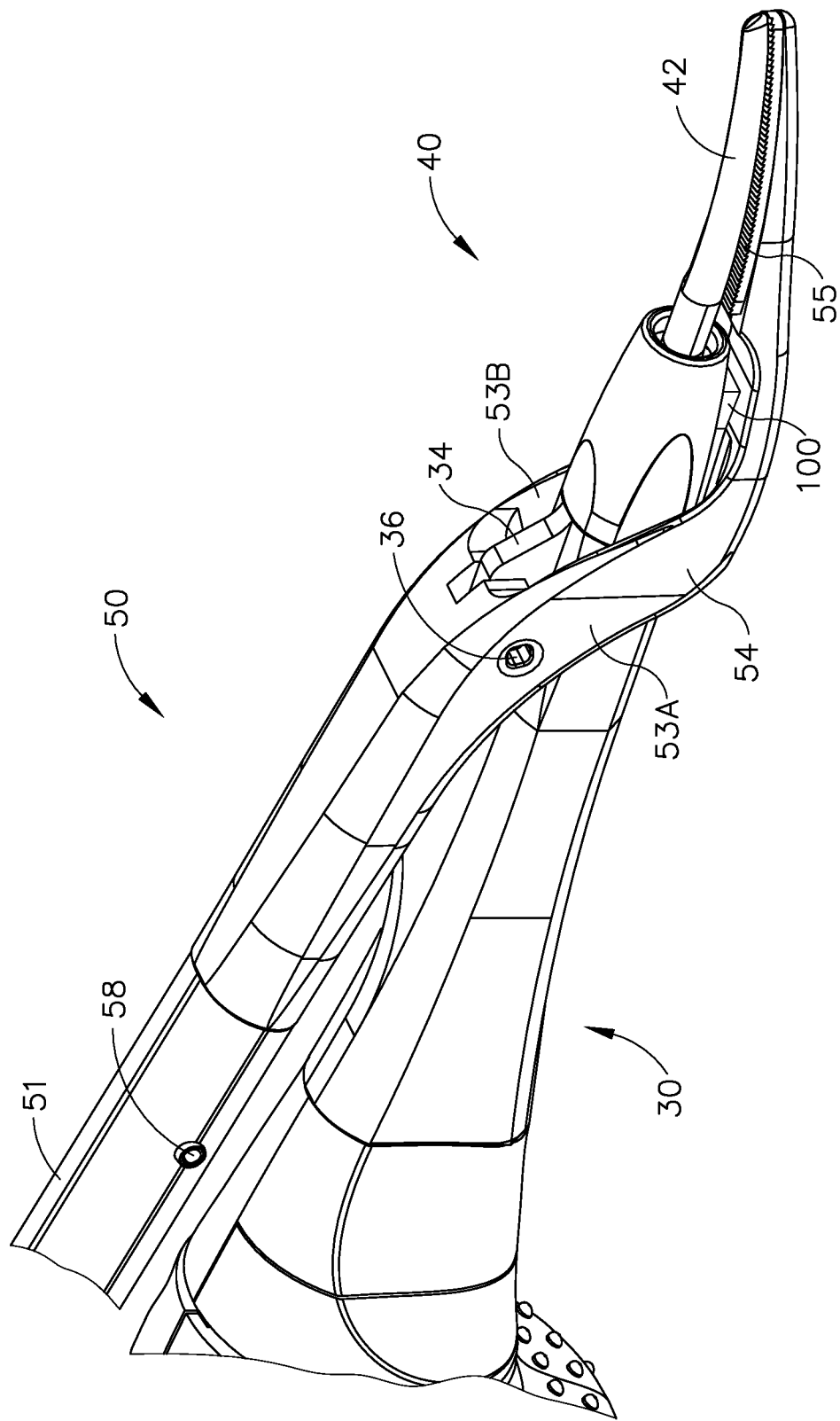
FIG. 8B depicts a perspective view of the distal end configuration of FIG. 7A, in the closed position.

FIGS. 7A-8B show an exemplary guide feature (100) that is configured to guide clamp arm (54) such that clamp arm (54) and/or clamp pad (55) adequately and appropriately engage ultrasonic blade (42) as clamp arm (54) is pivoted toward ultrasonic blade (42). Guide feature (100) of this example comprises a curved projection located proximally of channel (57) and clamp pad (55). As shown in FIGS. 7A and 8A, when clamp arm assembly (50) is in an open position, guide feature (100) extends from clamp arm (54) toward an opposing surface of shaft assembly (30). Guide feature (100) has a curved, generally rectangular shaped exterior. The opposing surface of shaft assembly (30) presents a recess (not shown) having a curved, generally rectangular interior shape such that the recess is configured to slidably receive guide feature (100), as shown in FIGS. 7B and 8B. It should therefore be understood that the interaction between guide feature (100) and the recess will guide clamp arm (54) into lateral and angular alignment with ultrasonic blade (42) as clamp arm (54) is pivoted toward ultrasonic blade (42).

The recess in shaft assembly (30) may be tapered (e.g., with tapered lateral walls) such that as clamp arm (54) is pivoted further toward ultrasonic blade (42), and as guide feature (100) is driven further into the recess, the interior shape of the recess more closely resembles that of guide feature (100) thus guiding clamp arm (54) into an intended position. Alternatively, guide feature (100) may be tapered such that as clamp arm (54) is pivoted further toward ultrasonic blade (42), and as guide feature (100) is driven further into the recess, the exterior shape of guide feature (100) more closely resembles that of the recess thus guiding clamp arm (54) into an intended position.

B. Second Exemplary Guide Feature

Figure 9A:
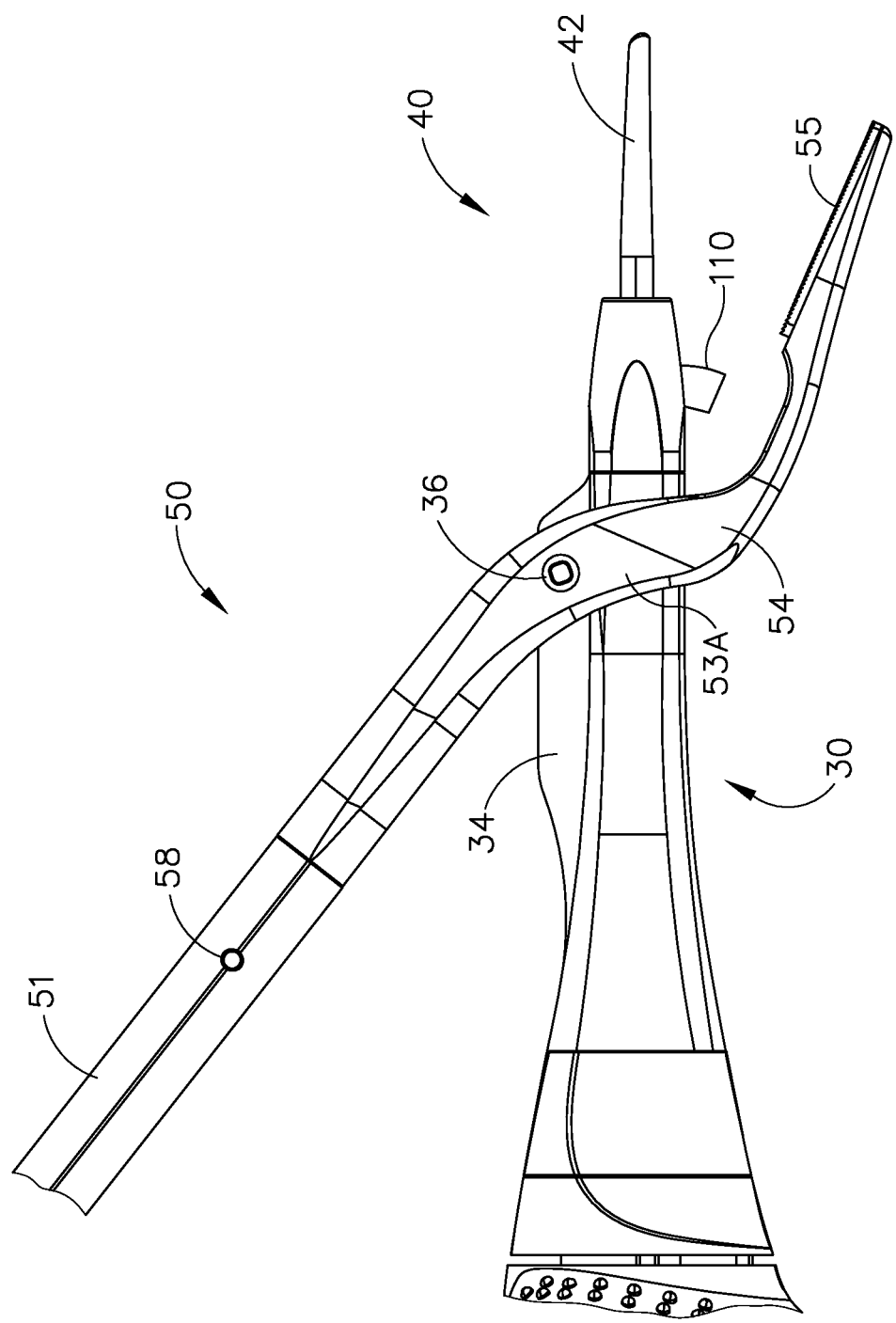
FIG. 9A depicts a side elevational view of a version of the distal end of the instrument of FIG. 1 with exemplary alternative guide features, in an open position.
Figure 9B:
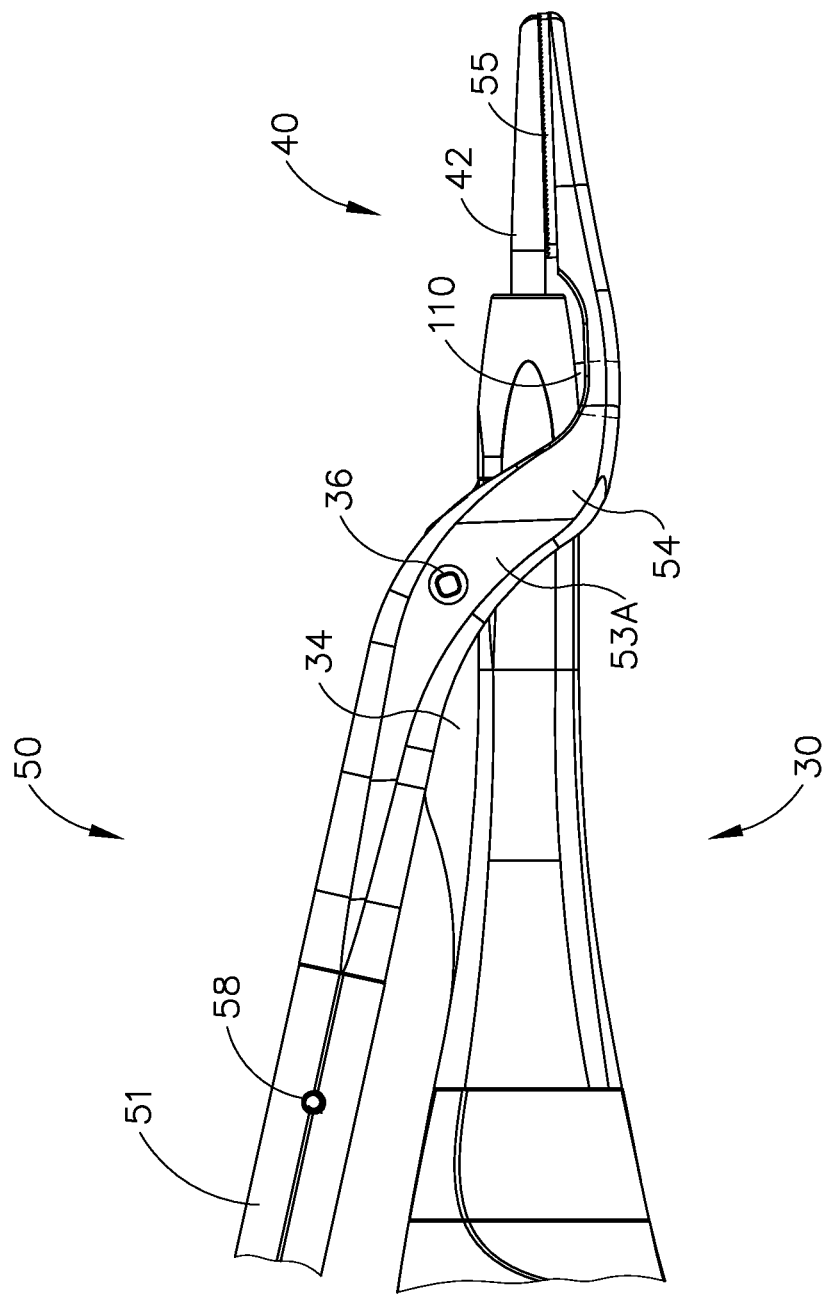
FIG. 9B depicts a side elevational view of the distal end configuration of FIG. 9A, in a closed position.
Figure 10A:
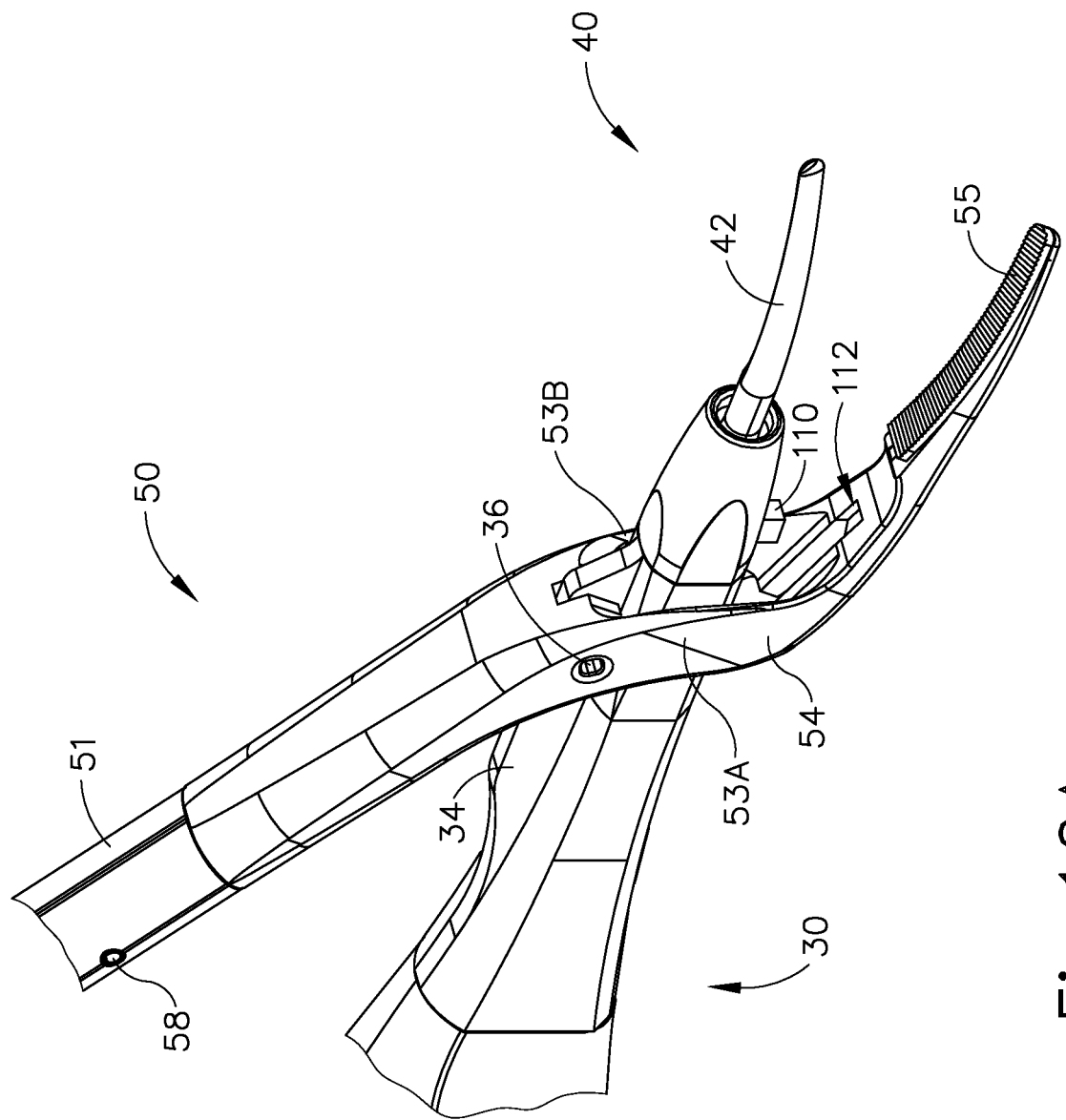
FIG. 10A depicts a perspective view of the distal end configuration of FIG. 9A, in the open position.
Figure 10B:
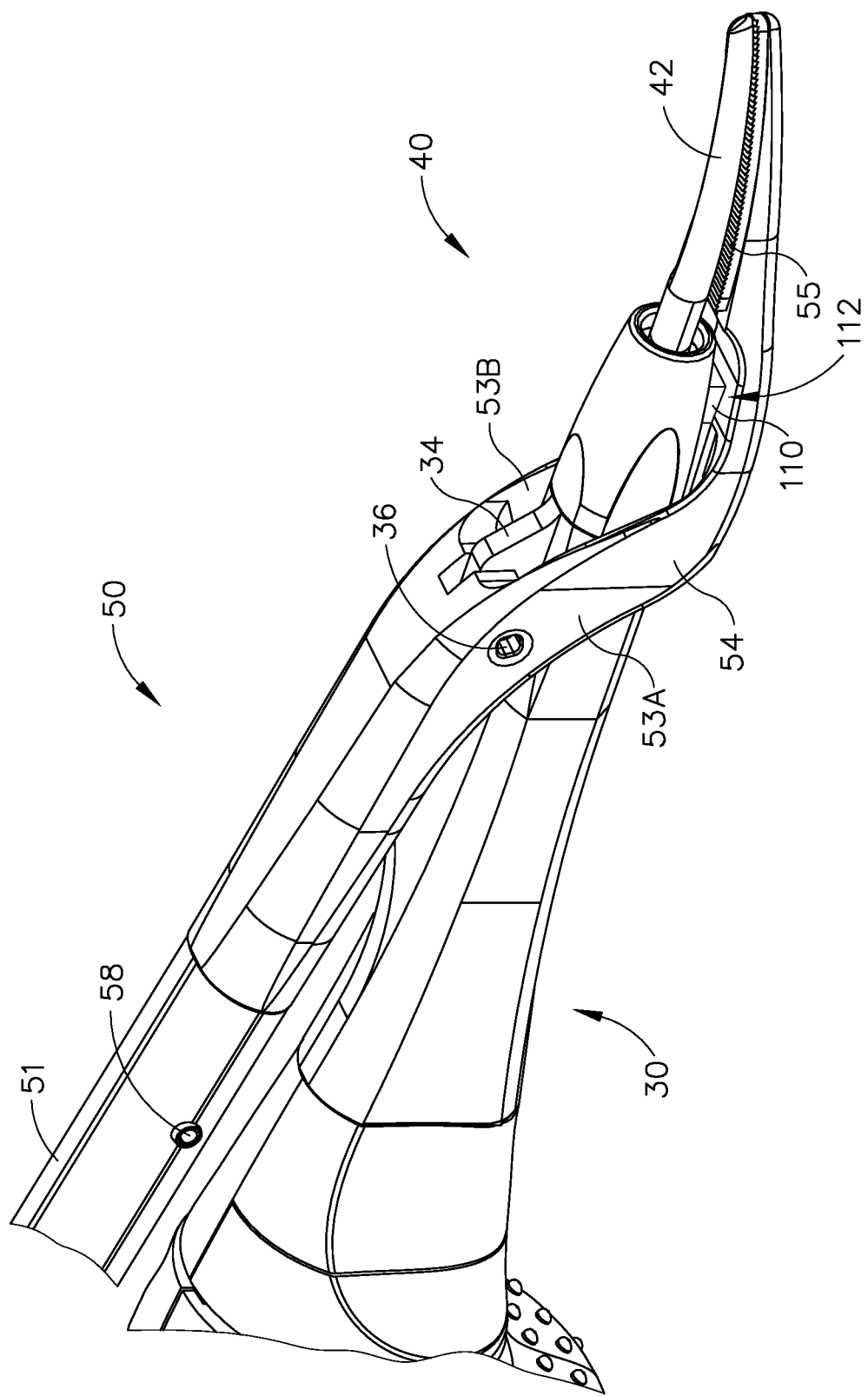
FIG. 10B depicts a perspective view of the distal end configuration of FIG. 9A, in the closed position.

FIGS. 9A-10B show an exemplary alternative guide feature (110) that is configured to guide clamp arm (54) such that clamp arm (54) and/or clamp pad (55) adequately and appropriately engage ultrasonic blade (42) as clamp arm (54) is pivoted toward ultrasonic blade (42). Guide feature (110) of this example comprises a curved projection extending transversely from a distal portion of shaft assembly (30), proximal to blade (40). As shown in FIGS. 9A and 10A, when clamp arm assembly (50) is in an open position, guide feature (110) extends from shaft assembly (30) toward an opposing surface of clamp arm (54). Guide feature (110) has a curved, generally rectangular shaped exterior. The opposing surface of clamp arm (54) presents a recess (112) having a curved, generally rectangular interior shape such that recess (112) is configured to slidably receive guide feature (110), as shown in FIGS. 9B and 10B. It should therefore be understood that the interaction between guide feature (110) and recess (112) will guide clamp arm (54) into lateral and angular alignment with ultrasonic blade (42) as clamp arm (54) is pivoted toward ultrasonic blade (42).

Recess (112) may be tapered (e.g., with tapered lateral walls) such that as clamp arm (54) is pivoted further toward ultrasonic blade (42), and as guide feature (110) is driven further into recess (112), the interior shape of recess (112) more closely resembles that of guide feature (110) thus guiding clamp arm (54) into an intended position. Alternatively, guide feature (110) may be tapered such that as clamp arm (54) is pivoted further toward ultrasonic blade (42), and as guide feature (110) is driven further into recess (112), the exterior shape of guide feature (100) more closely resembles that of recess (112) thus guiding clamp arm (54) into an intended position.

Figure 11:
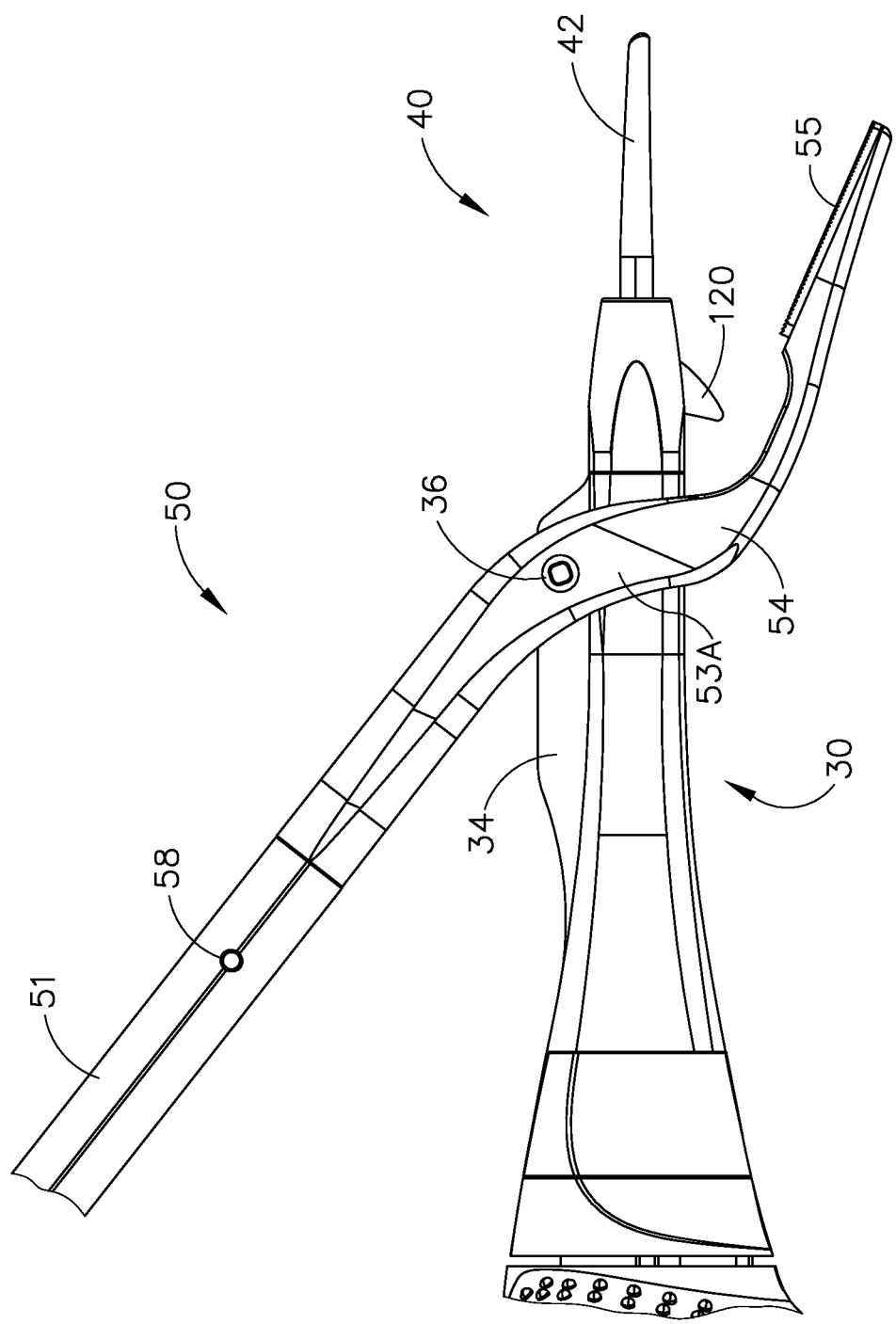
FIG. 11 depicts a side elevational view of a version of the distal end of the instrument of FIG. 1 with other exemplary alternative guide features, in an open position.
Figure 12:
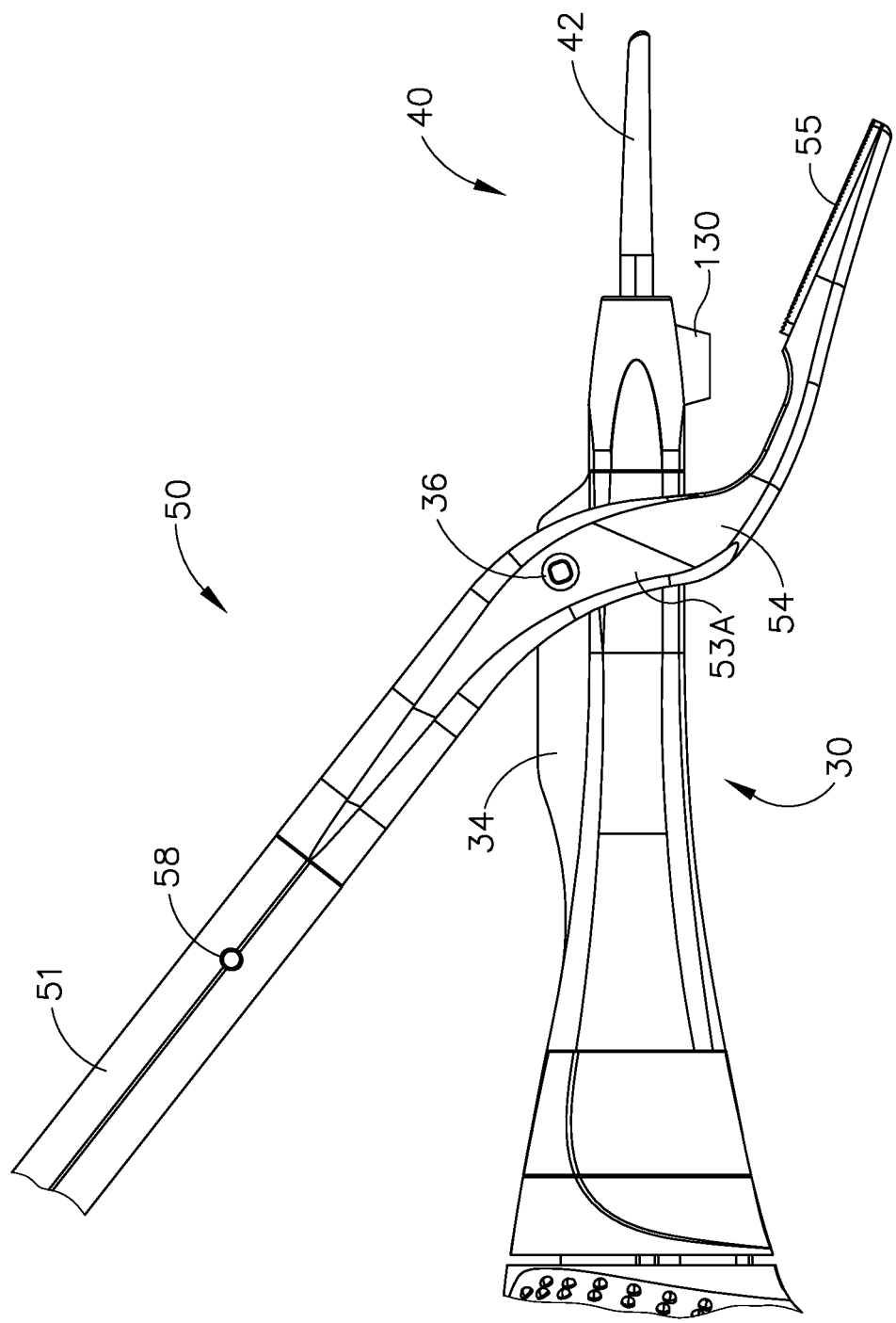
FIG. 12 depicts a side elevational view of a version of the distal end of the instrument of FIG. 1 with other exemplary alternative guide features, in an open position.
Figure 13:
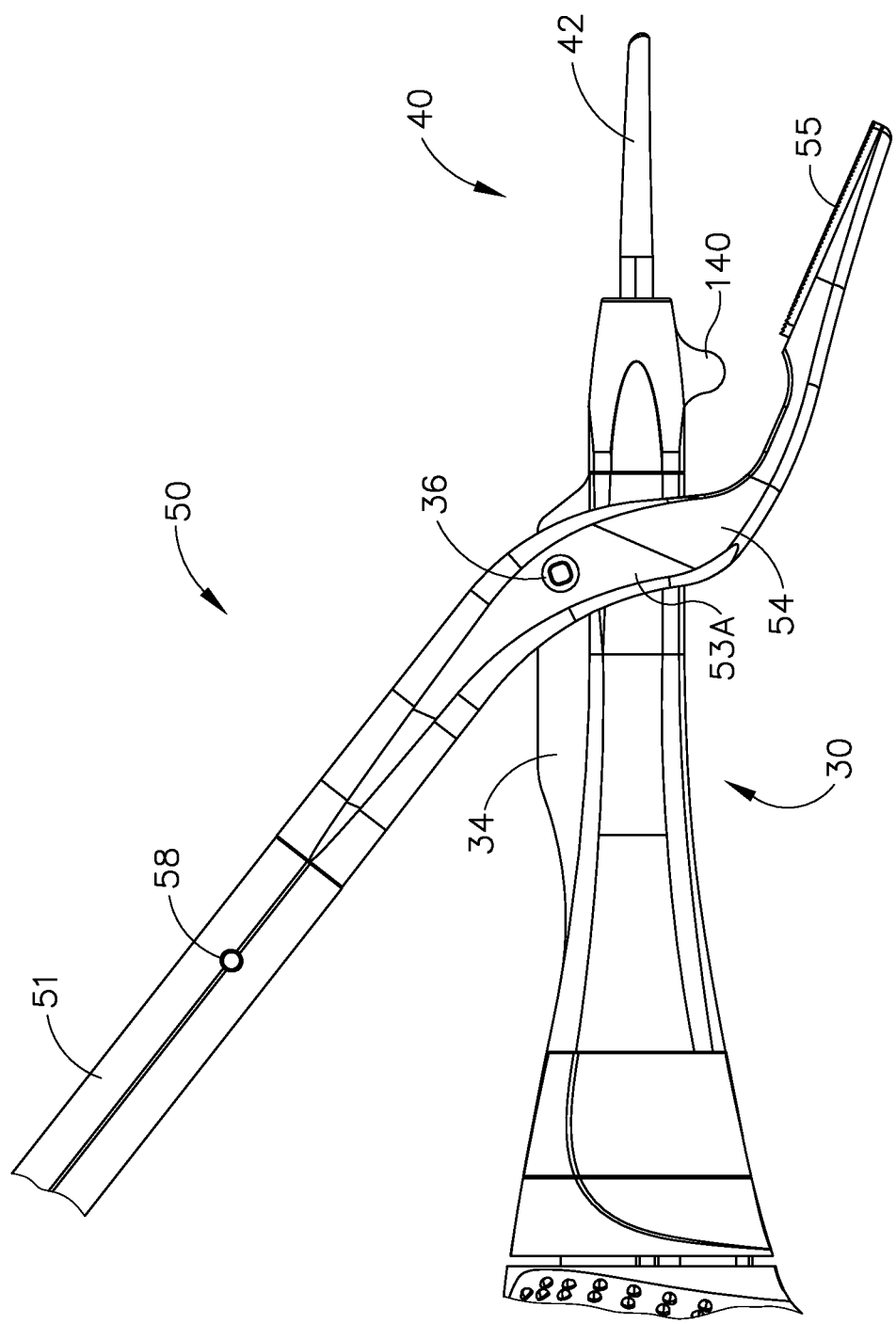
FIG. 13 depicts a side elevational view of a version of the distal end of the instrument of FIG. 1 with other exemplary alternative guide features, in an open position.

FIGS. 11-13 show exemplary alternative guide features (120, 130, 140) that are configured to operate substantially similar to guide feature (110) discussed above except for the differences discussed below. In particular, guide features (120, 130, 140) are configured to guide clamp arm (54) such that clamp arm (54) and/or clamp pad (55) adequately and appropriately engage ultrasonic blade (42) as clamp arm (54) is pivoted toward ultrasonic blade (42).

Guide feature (120) shown in FIG. 11 comprises a fin-like shaped projection extending transversely from shaft assembly (30). The opposing surface of clamp arm (54) presents a recess (not shown) configured to slidably receive guide feature (120) as clamp arm (54) is pivoted toward ultrasonic blade (42). An interior surface of the recess is configured to closely resemble that of guide feature (120). It should therefore be understood that the interaction between guide feature (120) and the recess will guide clamp arm (54) into lateral and angular alignment with ultrasonic blade (42) as clamp arm (54) is pivoted toward ultrasonic blade (42).

Guide feature (130) shown in FIG. 12 comprises a trapezoidal shaped projection extending transversely from shaft assembly (30). The opposing surface of clamp arm (54) presents a recess (not shown) configured to slidably receive guide feature (130) as clamp arm (54) is pivoted toward ultrasonic blade (42). An interior surface of the recess is configured to closely resemble that of guide feature (130). It should therefore be understood that the interaction between guide feature (130) and the recess will guide clamp arm (54) into lateral and angular alignment with ultrasonic blade (42) as clamp arm (54) is pivoted toward ultrasonic blade (42).

Guide feature (140) shown in FIG. 13 comprises a bell shaped projection extending transversely from shaft assembly (30). The opposing surface of clamp arm (54) presents a recess (not shown) configured to slidably receive guide feature (140) as clamp arm (54) is pivoted toward ultrasonic blade (42). An interior surface of the recess is configured to closely resemble that of guide feature (140). It should therefore be understood that the interaction between guide feature (140) and the recess will guide clamp arm (54) into lateral and angular alignment with ultrasonic blade (42) as clamp arm (54) is pivoted toward ultrasonic blade (42).

It should be understood that any of the guide features (120, 130, 140) discussed above may be extend from clamp arm (54) toward an opposing surface of shaft assembly (30), much like guide feature (100) discussed above. It should further be understood that any of the guide features (100, 110, 120, 130, 140) discussed above may be used in combination with one another and may extend from either clamp arm (54), shaft assembly (30), or both. While the guide features (100, 110, 120, 130, 140) discussed above extend into recesses formed in either clamp arm (54) or shaft assembly (30), alternative guide features may instead be configured to engage the lateral outer surfaces of clamp arm (54) or shaft assembly (30).

C. Third Exemplary Guide Feature

Figure 14:
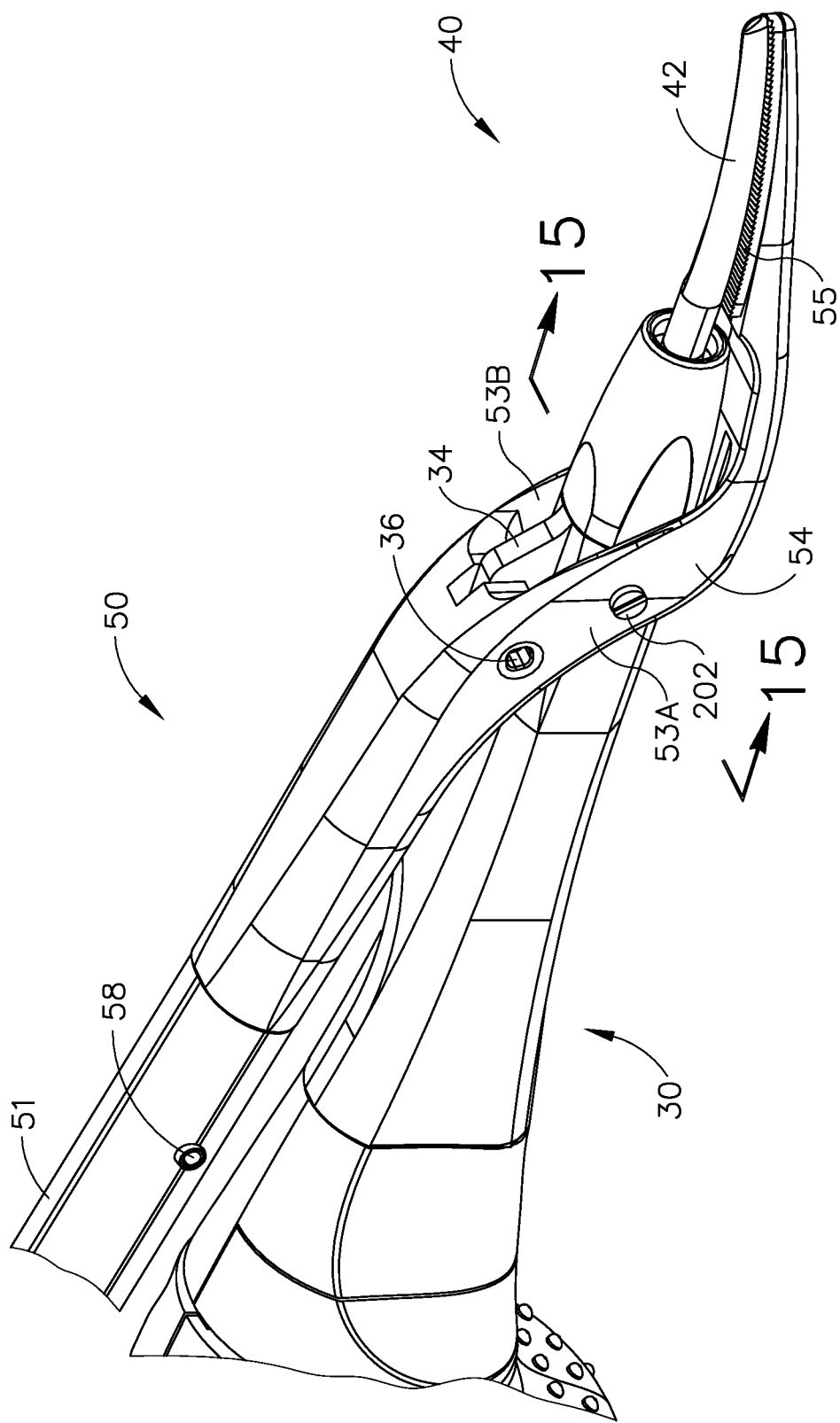
FIG. 14 depicts a perspective view of a version of the distal end of the instrument of FIG. 1 with other exemplary alternative guide features.
Figure 16:
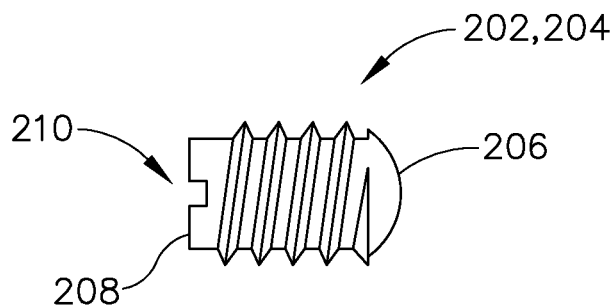
FIG. 16 depicts a side elevational view of an exemplary set screw of the distal end configuration of FIG. 14.
Figure 15:
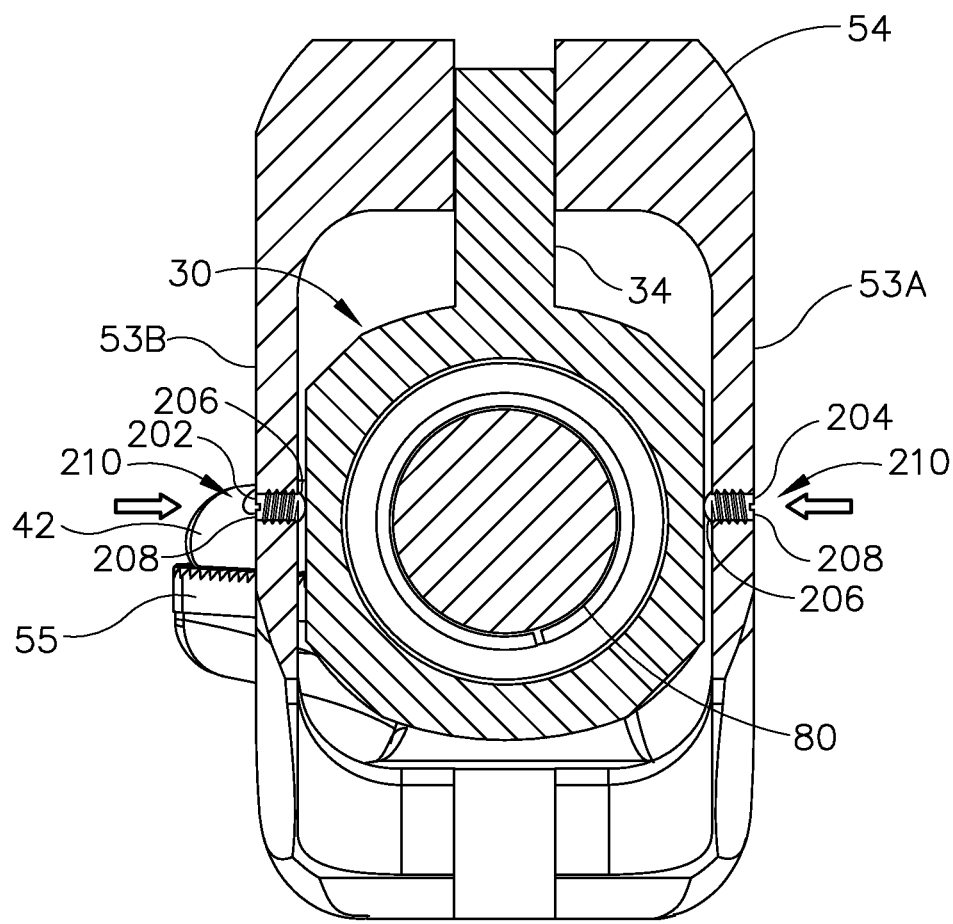
FIG. 15 depicts a cross-sectional view of the distal end configuration of FIG. 14 taken along line 15-15 of FIG. 14.

FIGS. 14-16 show a pair set screws (202, 204) that together form a guide feature. In this version of instrument (10), first member (53A) and second member (53B) of clamp arm (54) each present a transverse threaded bore that passes completely therethough. Each threaded bore is configured to receive a single set screw (202, 204). Each set screw (202, 204) comprises a rounded contact surface (206) that is configured to engage an exterior surface of shaft assembly (30). As shown in FIG. 15, set screws (202, 204) pass through first member (53A) and second member (53B) with set screws (202, 204) in coaxial alignment with each other such that spherical contact surfaces (206) of set screws (202, 204) contact exterior surfaces of shaft assembly (30) in an opposing fashion. Each set screw (202) further comprises a flat surface (208). Flat surface (208) presents an engagement slot (210) configured to allow an operator to rotate each set screw (202, 204) within a respective threaded bore. For instance, engagement feature (210) formed in flat surface (208) may comprise a slot for a flathead screwdriver, a Phillips-head feature, or a hex key feature. Engagement features (210) of set screws (202, 204) thereby allow an operator to adjust a depth of each set screw (202, 204)—inwardly and outwardly—to thereby control the amount of force exerted upon the exterior surface of shaft assembly (30) and further center clamp arm (54) relative to blade (42). It should be understood that set screws (202, 204) may be adjusted independently to thereby manipulate the alignment of clamp arm (54) and clamp pad (55) relative to ultrasonic blade (42). As clamp arm (54) is pivoted toward and away from ultrasonic blade (42), set screws (202, 204) will opposingly bear against the exterior surface of shaft assembly (30) along an arcuate path.

It should be understood that with set screws (202, 204) positioned within the threaded bores of first member (53A) and second member (53B), each flat surface (208) of set screws (202, 204) may be substantially flush with or recessed relative to the exterior surfaces of first member (53A) and second member (53B), to avoid inadvertent snagging, tearing, or ripping of tissue during operation.

D. Fourth Exemplary Guide Feature

Figure 17:
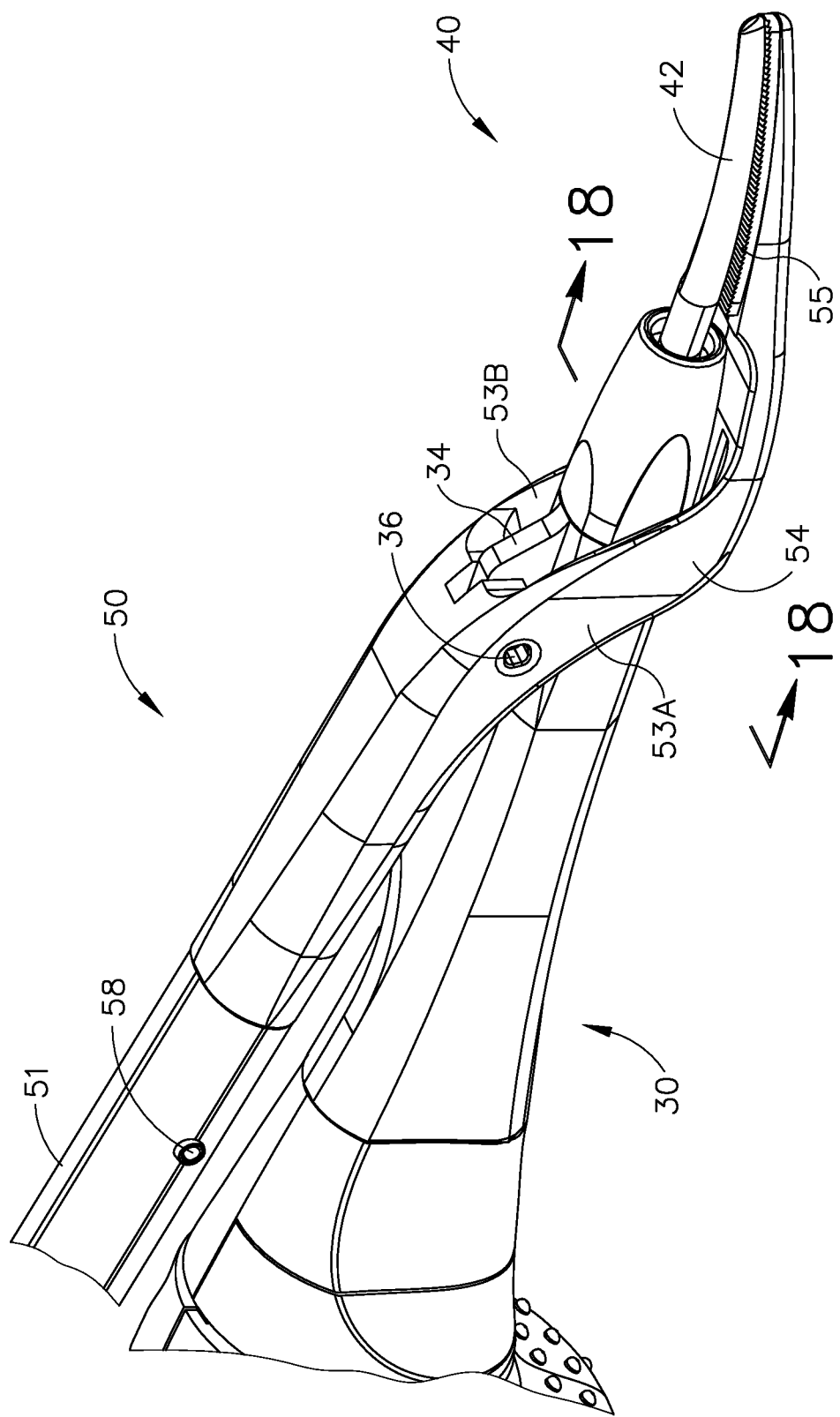
FIG. 17 depicts a perspective view of a version of the distal end of the instrument of FIG. 1 with other exemplary alternative guide features.
Figure 18:
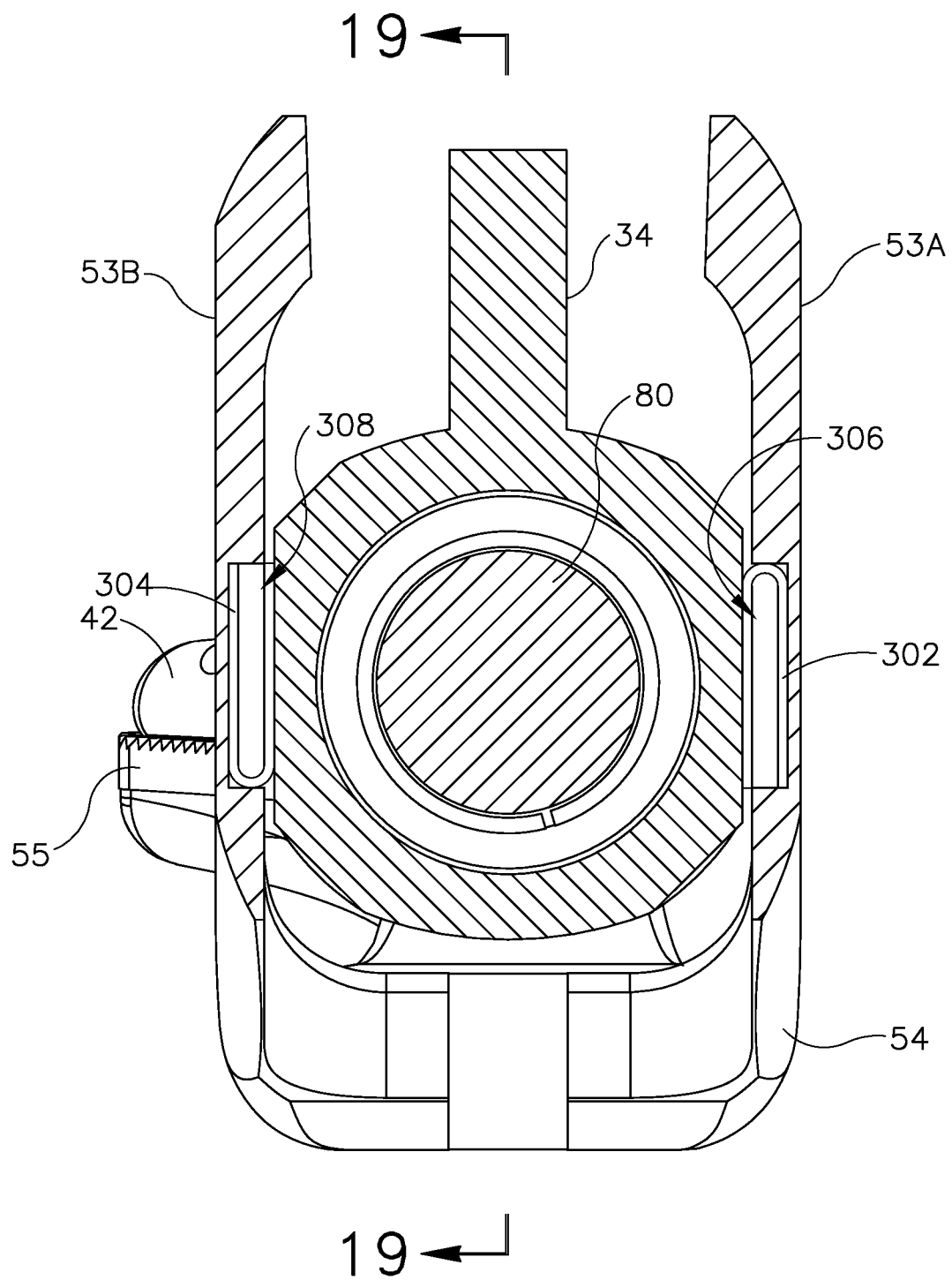
FIG. 18 depicts a cross-sectional view of the distal end configuration of FIG. 17 taken along line 18-18 of FIG. 17.
Figure 19:
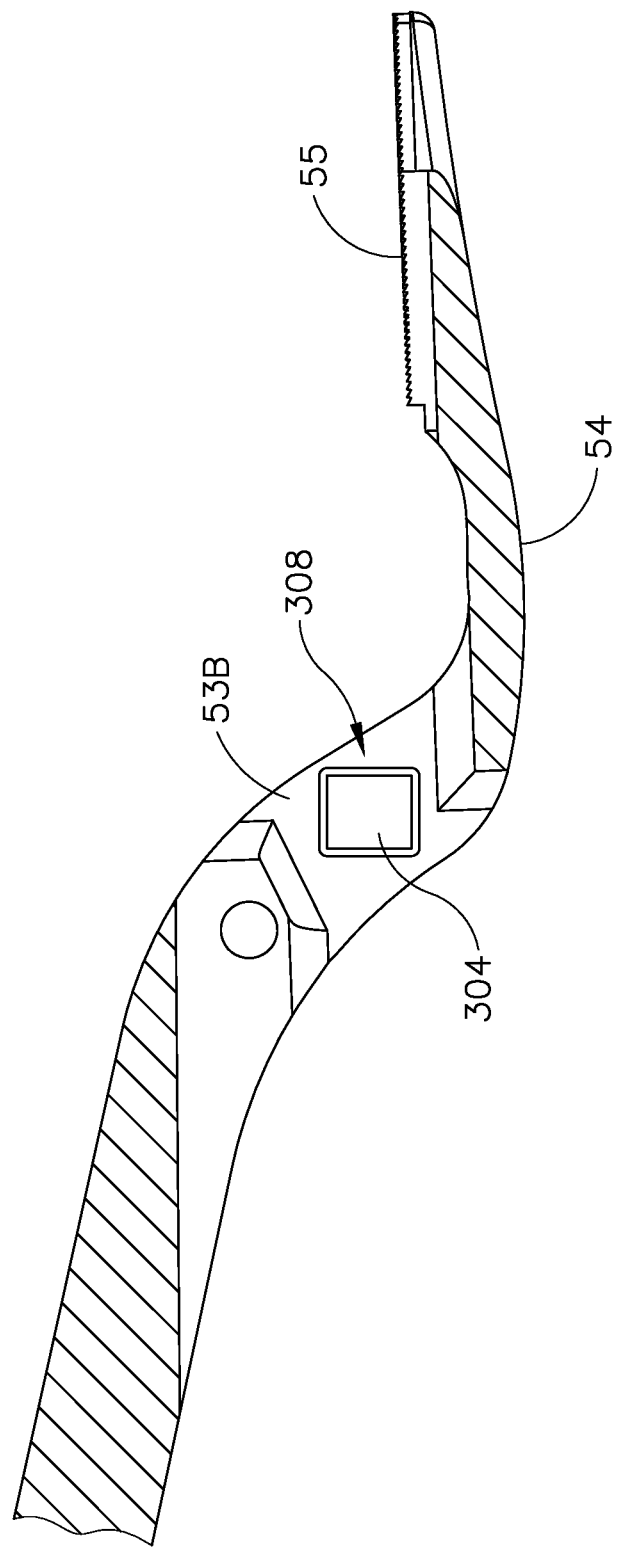
FIG. 19 depicts a cross-sectional view of a clamp arm of the distal end configuration of FIG. 17 taken along line 19-19 of FIG. 18.

FIGS. 17-19 show a pair of leaf springs (302, 304) that together form yet another exemplary alternative guide feature that is configured to guide clamp arm (54) such that clamp arm (54) and/or clamp pad (55) adequately and appropriately engage ultrasonic blade (42) as clamp arm (54) is pivoted toward ultrasonic blade (42). In this version of instrument (10), an interior surface of first member (53A) and second member (53B) of clamp arm (54) each present a rectangular recess (306, 608). As shown in FIGS. 18 and 19, each rectangular recess (306, 308) is configured to receive a single respective leaf spring (302, 304). With first member (53A) and second member (53B) of clamp arm (54) assembled together about shaft assembly (30), leaf springs (302, 304) bear inwardly against corresponding exterior surfaces of shaft assembly (30) in an opposing fashion. Leaf springs (302, 304) also bear outwardly on a corresponding interior surface of each rectangular recess (306, 308). Leaf springs (302, 304) thus cooperate to resiliently guide clamp arm (54) and clamp pad (55) into alignment with ultrasonic blade (42). It should be understood that leaf springs (302, 304) may have any stiffness to thereby exert more or less pressure on the exterior surface of shaft assembly (30) as desired. Furthermore, it should be understood that leaf springs (302, 304) may each have a different stiffness to thereby manipulate the alignment of clamp arm (54) and clamp pad (55) relative to ultrasonic blade (42). As clamp arm (54) is pivoted toward and away from ultrasonic blade (42), leaf springs (302, 304) will opposingly bear against the exterior surface of shaft assembly (30) along an arcuate path. In some variations, leaf springs (302, 304) are formed as integral components of clamp arm (54) through well known manufacturing processes (e.g., machining, molding, etc.).

Figure 20:
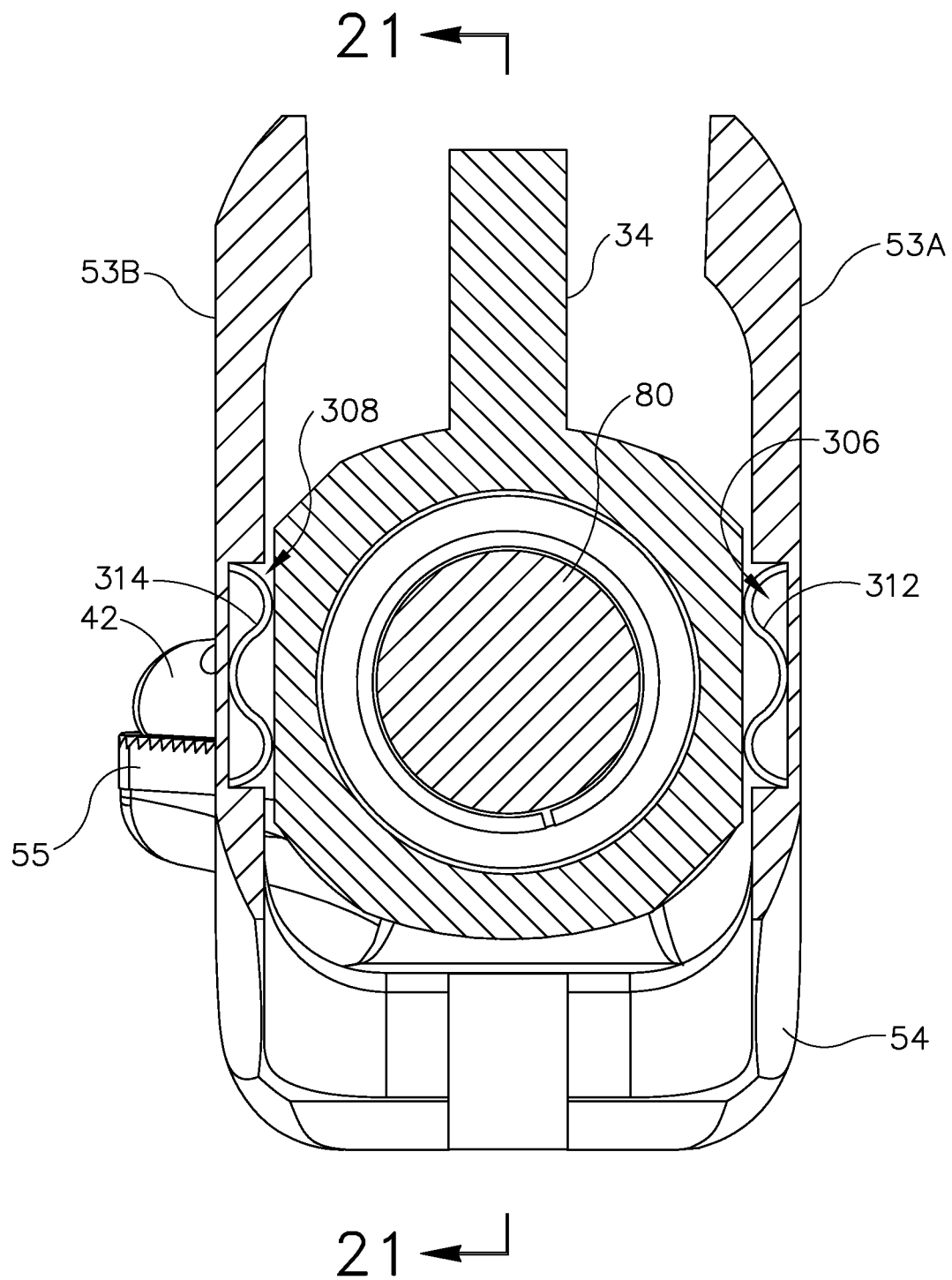
FIG. 20 depicts a cross-sectional end view of another exemplary alternative distal end configuration for the instrument of FIG. 1.
Figure 21:
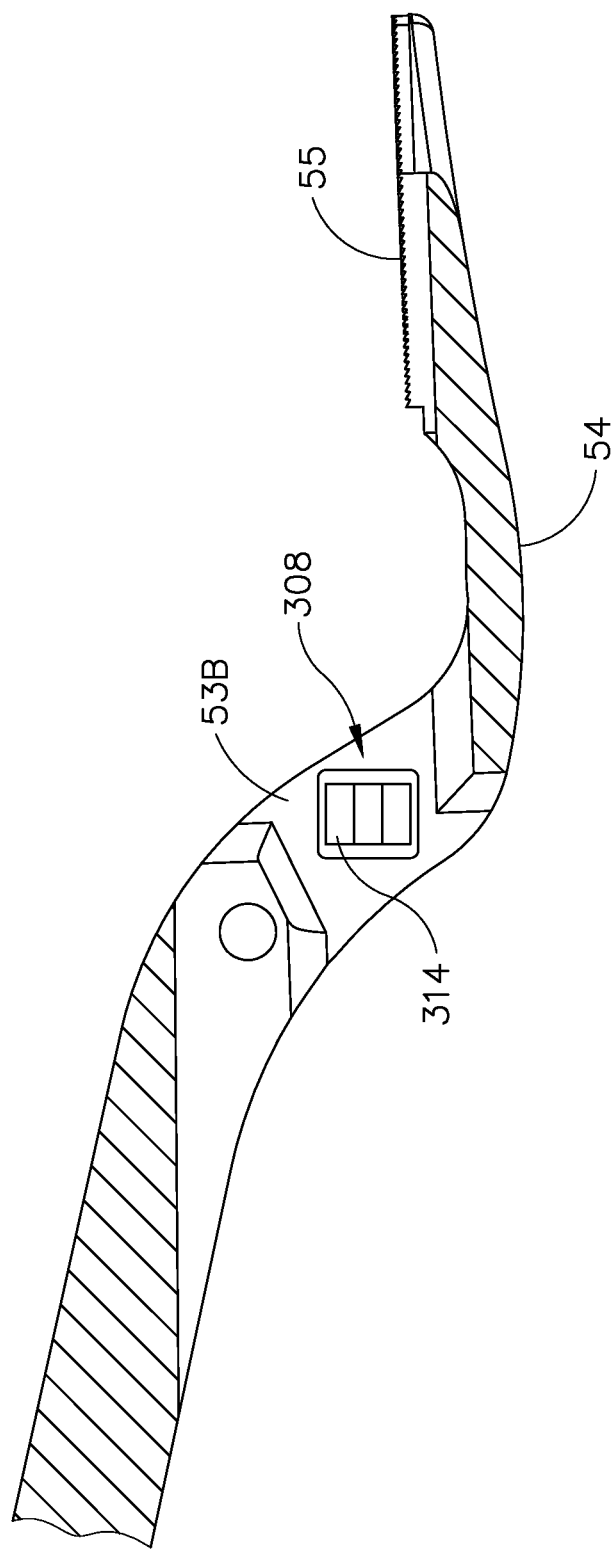
FIG. 21 depicts a cross-sectional view of a clamp arm of the distal end configuration of FIG. 20 taken along line 21-21 of FIG. 20.

FIGS. 20-23 show exemplary alternative components that serve as guide features operating substantially similar to leaf springs (302, 304) discussed above except for the differences discussed below. In particular, FIGS. 20-21 show a pair of wave springs (312, 314) that together act as a guide feature. Wave springs (312, 314) are configured to operate substantially similar to leaf springs (302, 304) discussed above except for the differences discussed below. In particular, wave springs (312, 314) are configured to fit within respective recesses (306, 308) of first member (53A) and second member (53B) of clamp arm (54), and are configured to bear against corresponding exterior surfaces of shaft assembly (30) as well as corresponding interior surfaces of rectangular recesses (306, 308) to thereby guide clamp arm (54) and clamp pad (55) into alignment with ultrasonic blade (42) as clamp arm (54) is pivoted toward ultrasonic blade (42). In other words, wave springs (312, 314) cooperate to resiliently guide clamp arm (54) and clamp pad (55) into alignment with ultrasonic blade (42).

It should be understood that wave springs (312, 314) may have any stiffness to thereby exert more or less pressure on the exterior surface of shaft assembly (30). Furthermore, it should be understood that wave springs (312, 314) may each have a different stiffness to thereby manipulate the alignment of clamp arm (54) and clamp pad (55) relative to ultrasonic blade (42). As clamp arm (54) is pivoted toward and away from ultrasonic blade (42), wave springs (312, 314) will bear against the exterior surface of shaft assembly (30) in an arcuate pattern.

Figure 22:
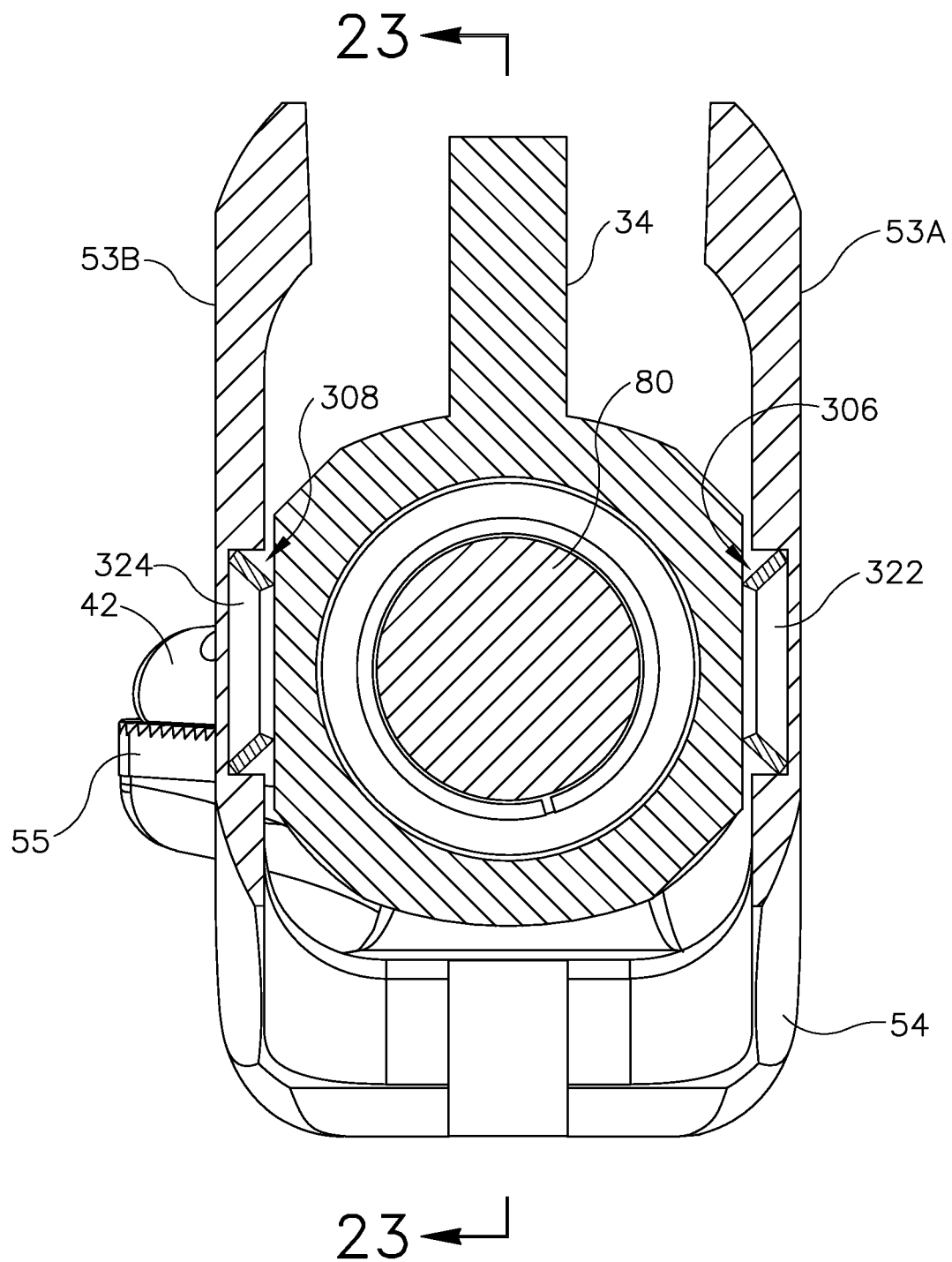
FIG. 22 depicts a cross-sectional end view of another exemplary alternative distal end configuration for the instrument of FIG. 1.
Figure 23:
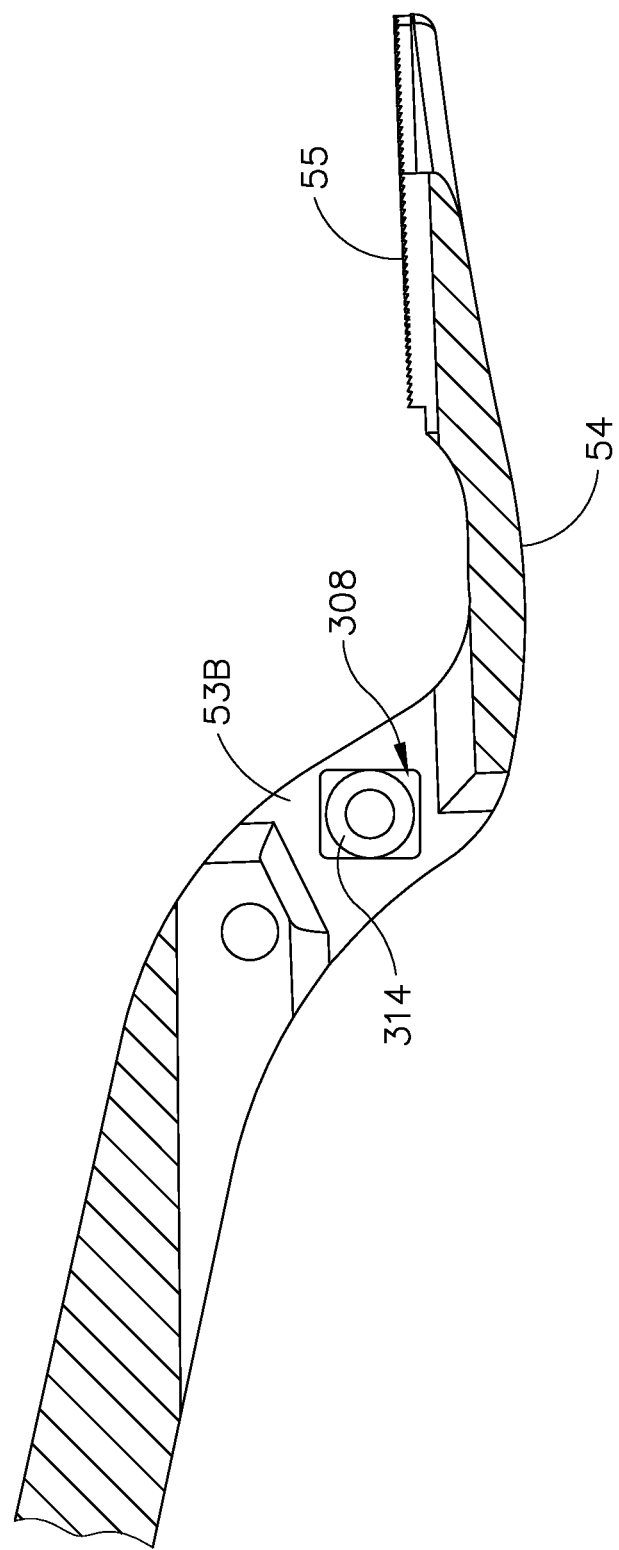
FIG. 23 depicts a cross-sectional view of a clamp arm of the distal end configuration of FIG. 22 taken along line 23-23 of FIG. 22.
Figure 24:
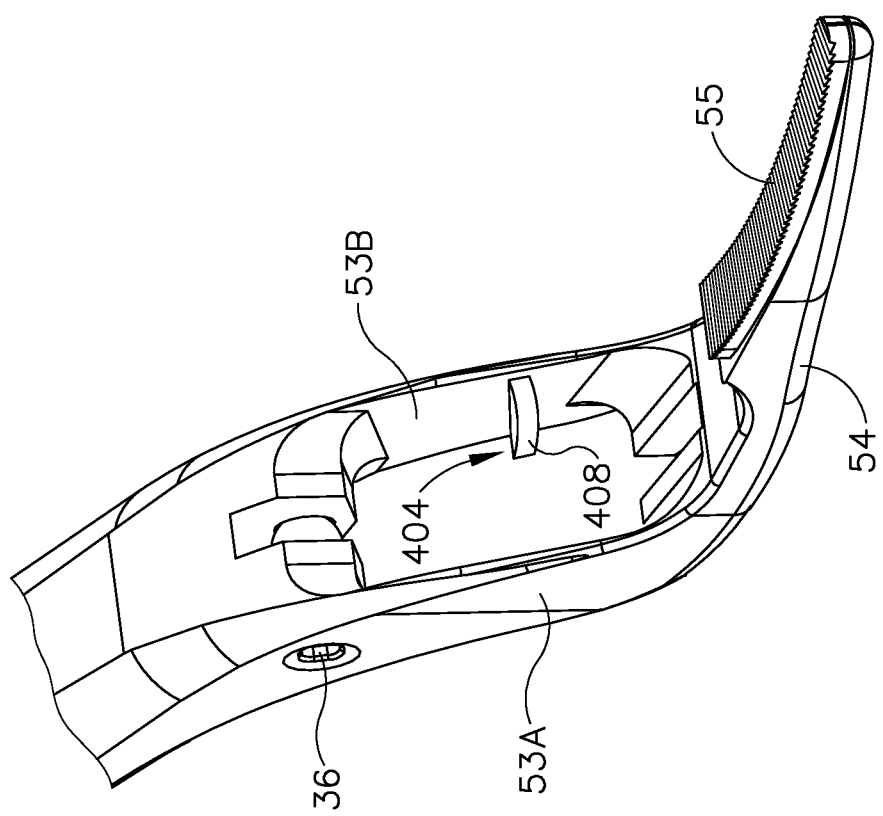
FIG. 24 depicts a perspective view of the distal end of an exemplary alternative clamp arm for the instrument of FIG. 1.
Figure 25:
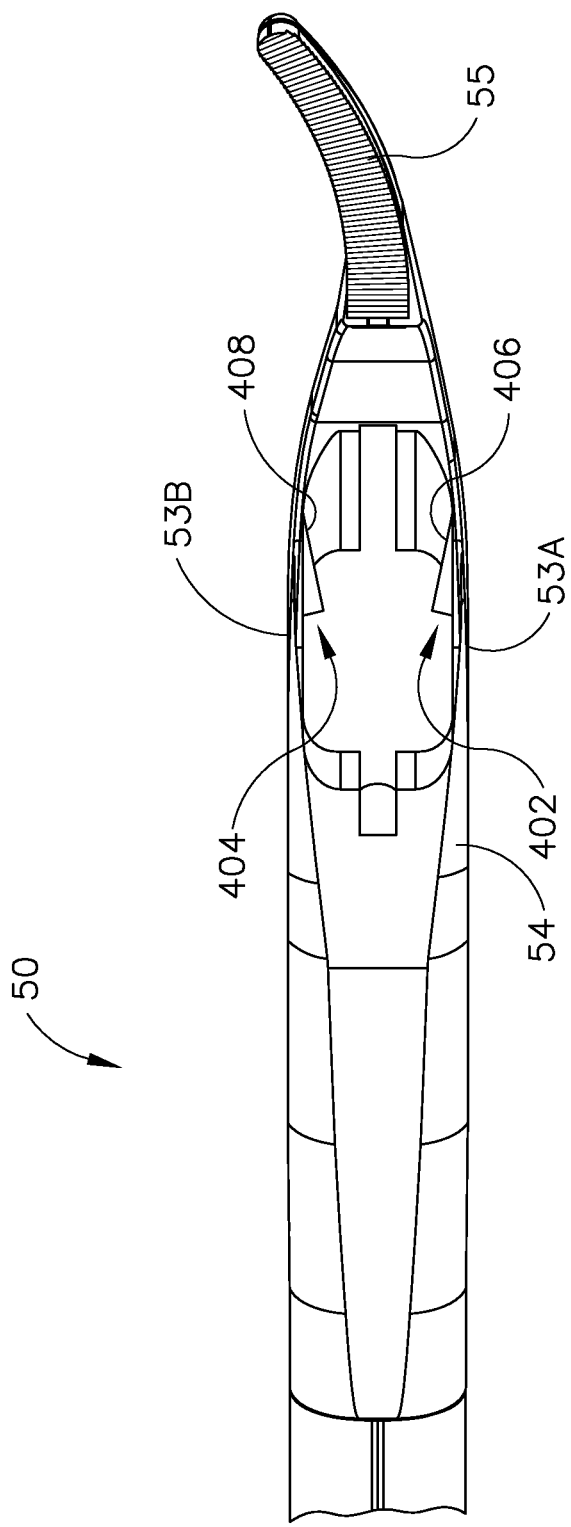
FIG. 25 depicts a top plan view of the clamp arm of FIG. 24.

FIGS. 22-23 show a pair of Belleville washers (322, 324) that together act as a guide feature. Belleville washers (322, 324) are configured to operate substantially similar to leaf springs (302, 304) discussed above except for the differences discussed below. In particular, Belleville washers (322, 324) are configured to fit within recesses (306, 308) of first member (53A) and second member (53B) of clamp arm (54), and are configured to bear against corresponding exterior surfaces of shaft assembly (30) as well as corresponding interior surfaces rectangular recesses (306, 308) to thereby guide clamp arm (54) and clamp pad (55) into alignment with ultrasonic blade (42) as clamp arm (54) is pivoted toward ultrasonic blade (42). In other words, Belleville washers (322, 324) cooperate to resiliently guide clamp arm (54) and clamp pad (55) into alignment with ultrasonic blade (42).

It should be understood that Belleville washers (322, 324) may have any stiffness to thereby exert more or less pressure on the exterior surface of shaft assembly (30). Furthermore, it should be understood that Belleville washers (322, 324) may each have a different stiffness to thereby manipulate the alignment of clamp arm (54) and clamp pad (55) relative to ultrasonic blade (42). As clamp arm (54) is pivoted toward and away from ultrasonic blade (42), Belleville washers (322, 324) will bear against the exterior surface of shaft assembly (30) along an arcuate path. In some variations, a ball bearing is interposed between each Belleville washer (322, 324) and shaft assembly (30) to reduce friction. It should be understood that ball bearings may be used in a similar fashion with any of the other resilient members referred to herein as slidably bearing against shaft assembly (30).

E. Fifth Exemplary Guide Feature

FIGS. 24-26B show a pair of arcuate ramps (402, 404) that together serve as yet another exemplary alternative guide feature (400) that is configured to guide clamp arm (54) such that clamp arm (54) and/or clamp pad (55) adequately and appropriately engage ultrasonic blade (42) as clamp arm (54) is pivoted toward ultrasonic blade (42). Arcuate ramps (402, 404) project inwardly from respective interior surfaces of first member (53A) and second member (53B) of clamp arm (54). Arcuate ramps are configured such that an interior surface (406, 408) of each arcuate ramp (402, 404) engages a corresponding exterior surface of shaft assembly (30). Arcuate ramps (402, 404) are positioned relative to first member (53A) and second member (53B) such that they align with each other. Arcuate ramps (402, 404) are oriented such that the interior surface (406, 408) of each arcuate ramp (402, 404) transitions from a wider distal portion to a narrower proximal portion.

Figure 26A:
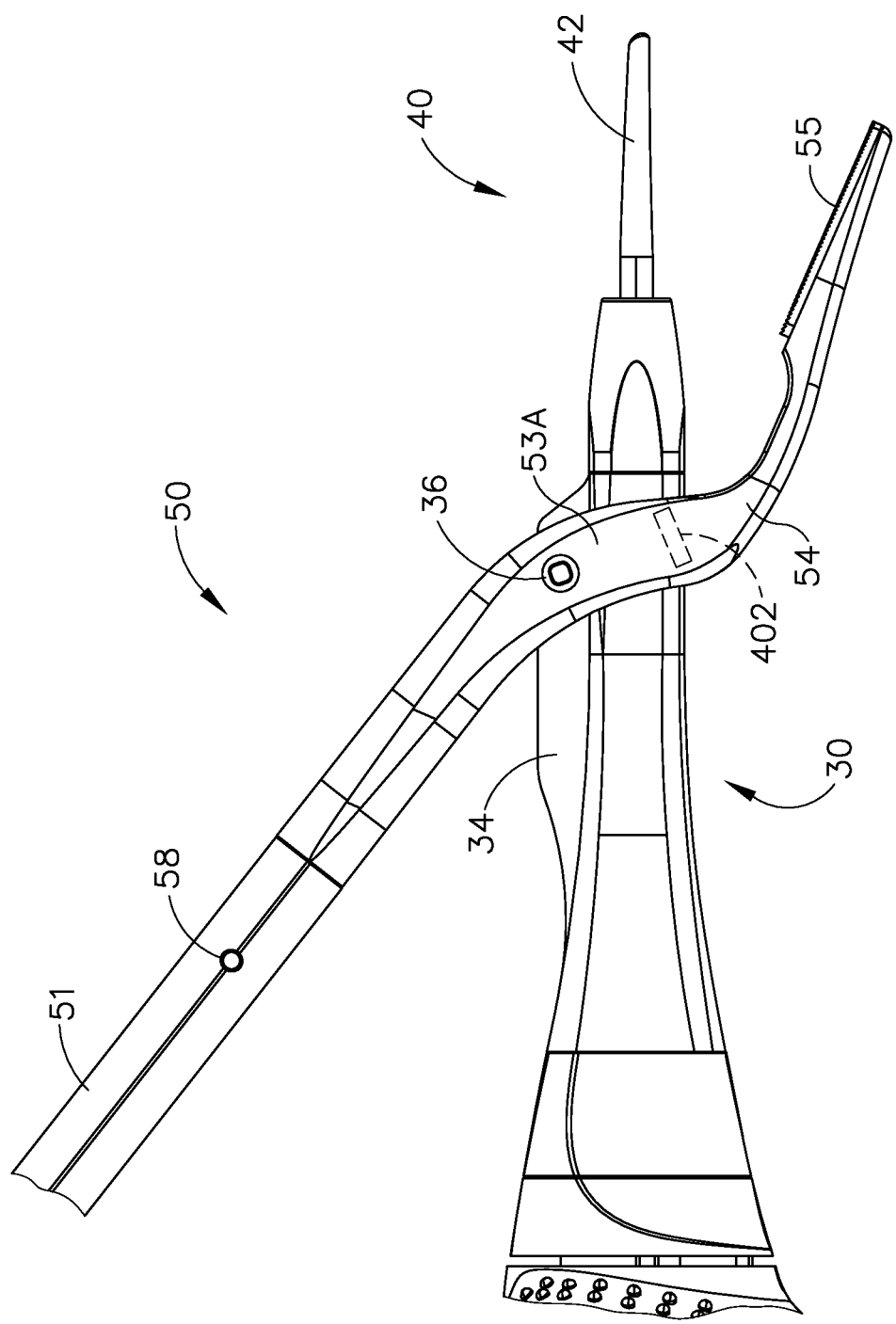
FIG. 26A depicts a side elevational view of the instrument of FIG. 1 with the clamp arm of FIG. 24, in an open position.
Figure 26B:
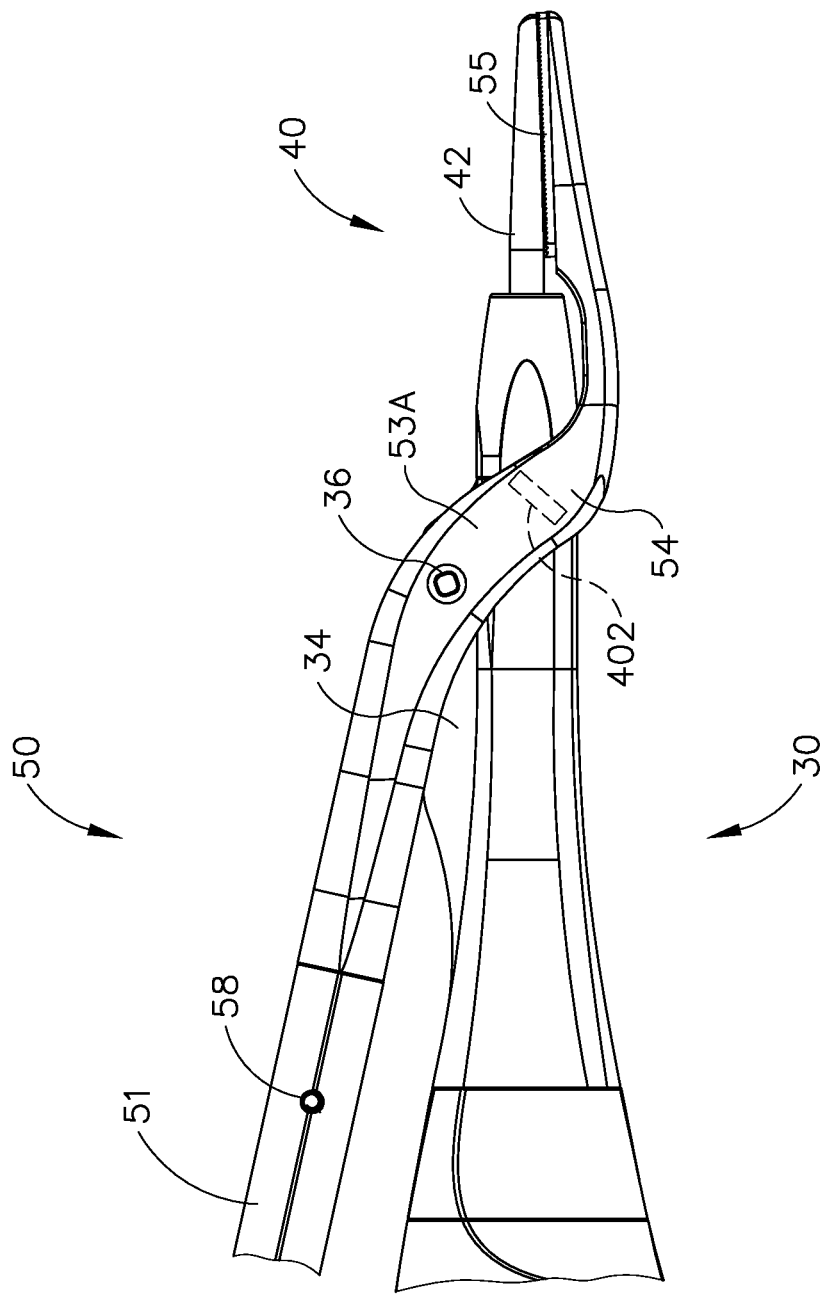
FIG. 26B depicts a side elevational view of the instrument of FIG. 1 with the clamp arm of FIG. 24, in a closed position.

With clamp arm (54) in the open position as shown in FIG. 26A, the wider distal portion of each arcuate ramp (402, 404) engages the exterior surface of shaft assembly (30). As clamp arm (54) is pivoted toward ultrasonic blade (42) as shown in FIG. 26B, arcuate ramps (402, 404) are also pivoted such that in the closed position, the narrow proximal portion of each arcuate ramp (402, 404) engages the exterior surface of shaft assembly (30) to thereby guide clamp arm (54) and clamp pad (55) into lateral and rotational alignment. In other words, ramps (402, 404) bear against the exterior surface of shaft assembly (30) with progressively increasing force as clamp arm (54) is pivoted toward ultrasonic blade (42), thereby further aligning clamp arm (54) with ultrasonic blade (42).

It should be understood that although interior surfaces (406, 408) of arcuate ramps (402, 404) of the present example have substantially similar angular inclines, interior surfaces (406, 408) of arcuate ramp (402, 404) may have different angular inclines to thereby manipulate the alignment of clamp arm (54) and clamp pad (55) relative to ultrasonic blade (42). Furthermore, it should be understood that although interior surfaces (406, 408) of arcuate ramps (402, 404) of the present example incline in a generally linear fashion, interior surfaces (406, 408) of arcuate ramps (402, 404) may incline at a variable rate. For instance, interior surfaces (406, 408) may be curved along a plane that extends through both surfaces (406, 408). It should also be understood that ramps (402, 404) may be rigid, semi-rigid, elastomeric, and/or have any other suitable properties.

F. Sixth Exemplary Guide Feature

Figure 27:
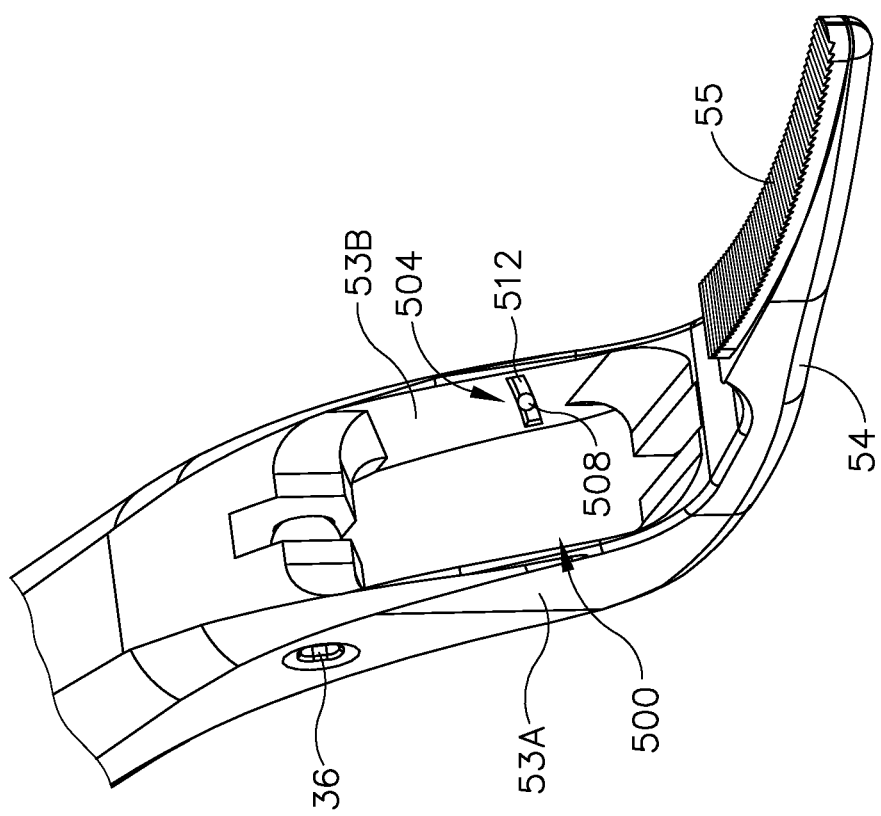
FIG. 27 depicts a perspective view of the distal end of another exemplary alternative clamp arm for the instrument of FIG. 1.
Figure 28A:
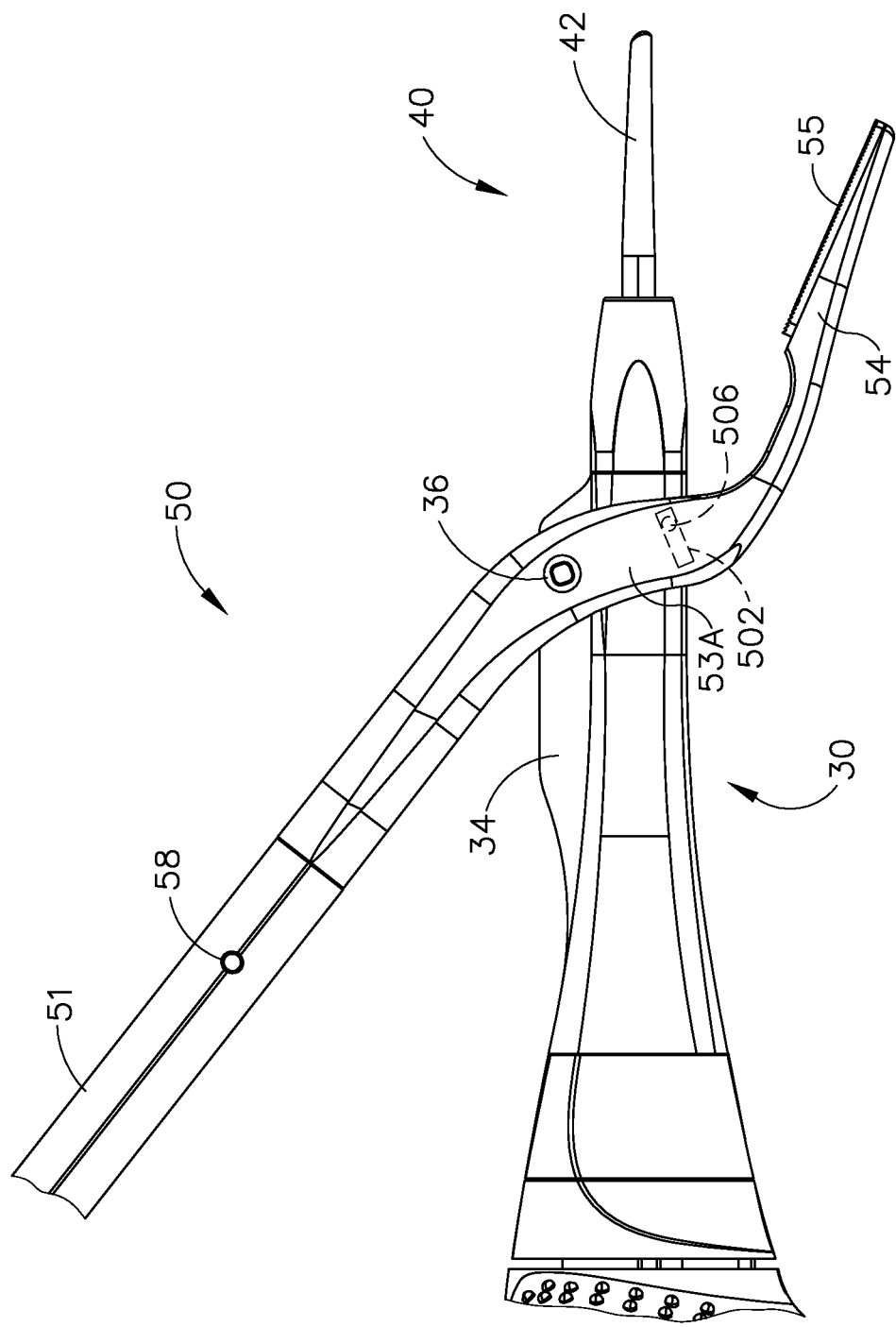
FIG. 28A depicts a side elevational view of the instrument of FIG. 1 with the clamp arm of FIG. 27, in an open position.
Figure 29:
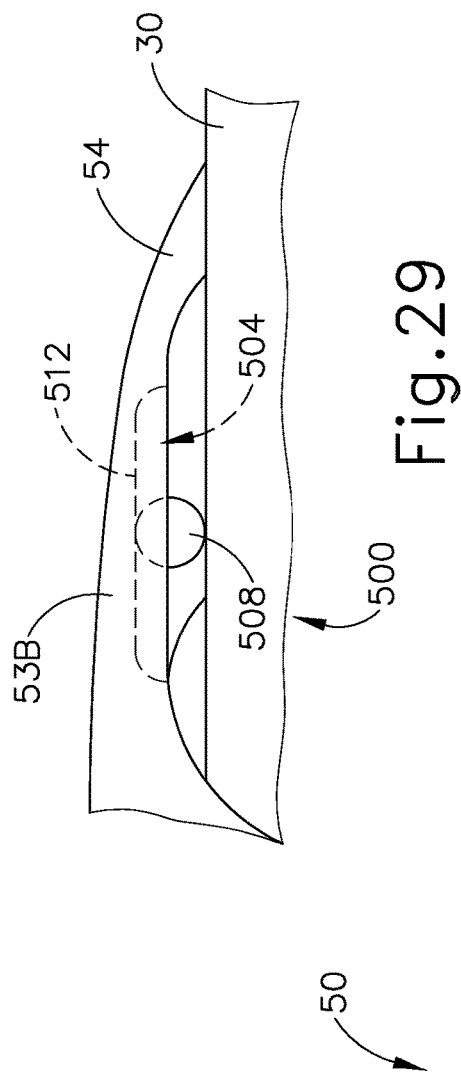
FIG. 29 depicts a partial top plan view of a guidance feature of the clamp arm of FIG. 27 engaging a fixed arm of the instrument of FIG. 1.
Figure 28B:
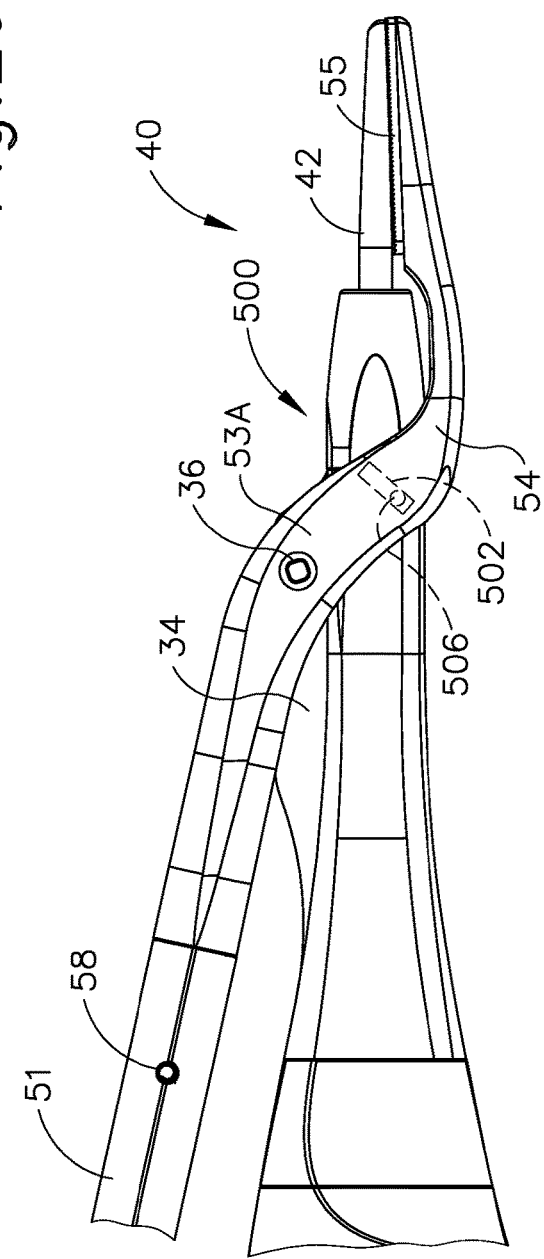
FIG. 28B depicts a side elevational view of the instrument of FIG. 1 with the clamp arm of FIG. 27, in a closed position.

FIGS. 27-29 show yet another exemplary alternative guide feature (500) that is configured to guide clamp arm (54) such that clamp arm (54) and/or clamp pad (55) adequately and appropriately engage ultrasonic blade (42) as clamp arm (54) is pivoted toward ultrasonic blade (42). Guide feature (500) of this example comprises a pair of arcuate recesses (502, 504) and a pair of ball bearings (506, 508). Arcuate recesses (502, 504) are defined in the interior surfaces of first member (53A) and second member (53B) of clamp arm (54). Each arcuate recess (502, 504) is configured to receive a single ball bearing (506, 508), though it should be understood that some other versions may include more than one ball bearing (506, 508) in each recess (502, 504). Ball bearings (506, 508) are configured to roll within and along each corresponding arcuate recesses (502, 504), as best seen in the transition from FIG. 28A to FIG. 28B. As best seen in FIG. 29, each ball bearing (506, 508) is configured to bear inwardly against a corresponding exterior surface of shaft assembly (30) and outwardly against a corresponding interior surface (510, 512) of rectangular recess (502, 504) to thereby guide clamp arm (54) and clamp pad (55) into alignment with ultrasonic blade (42) as clamp arm (54) is pivoted toward ultrasonic blade (42). Ball bearings (506, 508) may be formed of any suitable material. For instance, ball bearings (506, 508) may comprise an elastomeric material, a plastic material, a metallic material, etc.

Although not depicted in the present example of guide feature (500), shaft assembly (30) may comprise recesses or spherical indentations configured to receive ball bearings (506, 508). These recesses or indentations may be sized such that ball bearings (506, 508) will not slide within the recesses or indentations, but will instead only roll within these recesses or indentations such that as clamp arm (54) is pivoted toward and away from ultrasonic blade (42), these recesses or indentations will cause ball bearings (506, 508) to slide within arcuate recesses (502, 504).

It should be understood that the size of the ball bearings may be changed to thereby exert more or less pressure on the exterior surface of shaft assembly (30). It should also be understood that although ball bearings (506, 508) of the present example have substantially similar angular sizes, ball bearings (506, 508) may instead have different sizes to thereby manipulate the alignment of clamp arm (54) and clamp pad (55) relative to ultrasonic blade (42).

Furthermore, it should be understood that interior surfaces of arcuate recesses (502, 504) may be inclined such that the interior surface of each arcuate recess (502, 504) transitions from a wider or deeper distal portion to a narrower or shallower proximal portion. With clamp arm (54) in the open position, ball bearings (506, 508) would engage the wider/deeper distal portion of each arcuate recess (502, 504). As clamp arm (54) is pivoted toward ultrasonic blade (42), ball bearings (506, 508) would roll within arcuate recesses (502, 504) such that in the closed position, ball bearings (506, 508) engage the narrow/shallow proximal portion of each arcuate recess (502, 504) to thereby guide clamp arm (54) and clamp pad (55).

G. Seventh Exemplary Guide Feature

Figure 30:
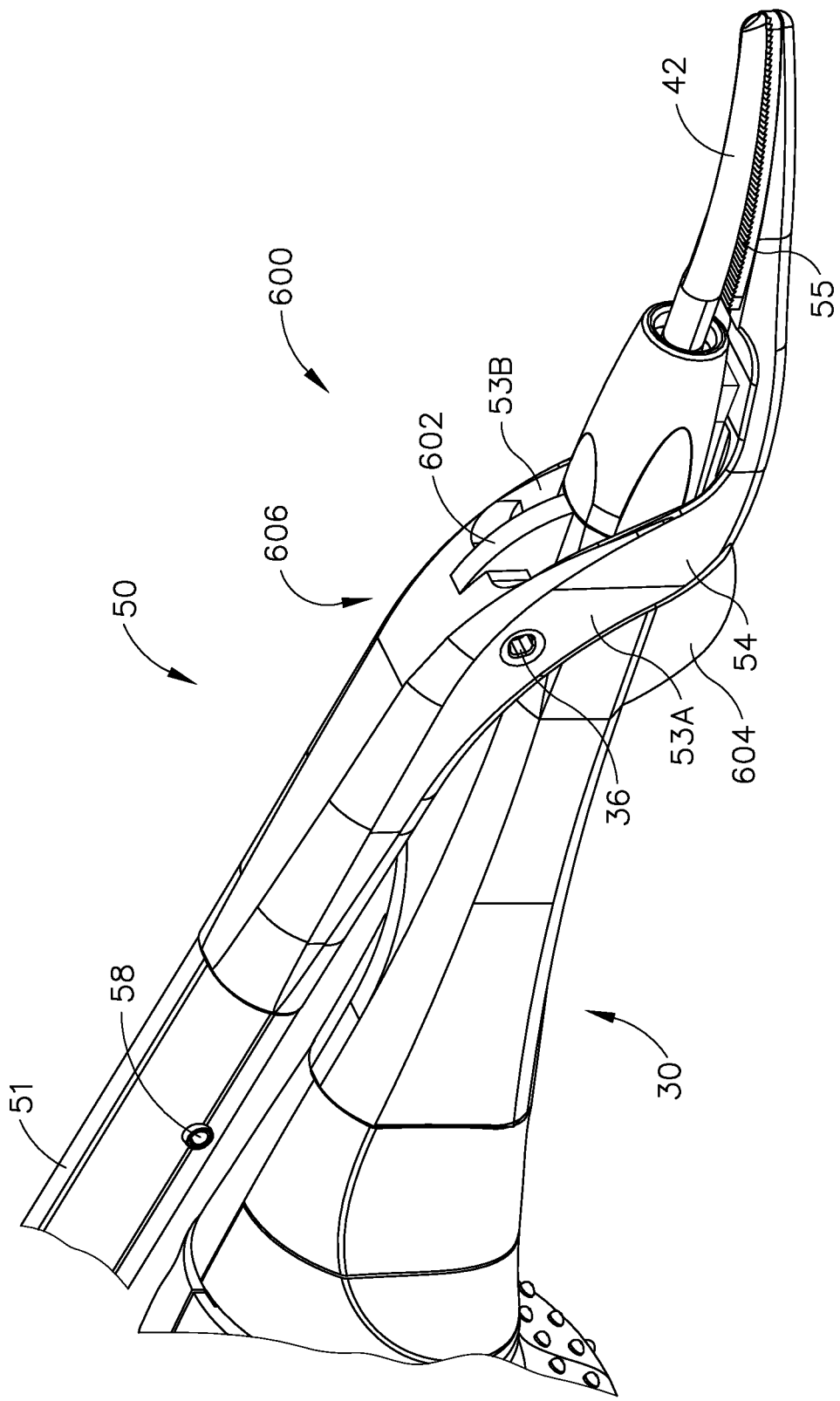
FIG. 30 depicts a perspective view of a version of the distal end of the instrument of FIG. 1 with other exemplary alternative guide features.
Figure 31A:
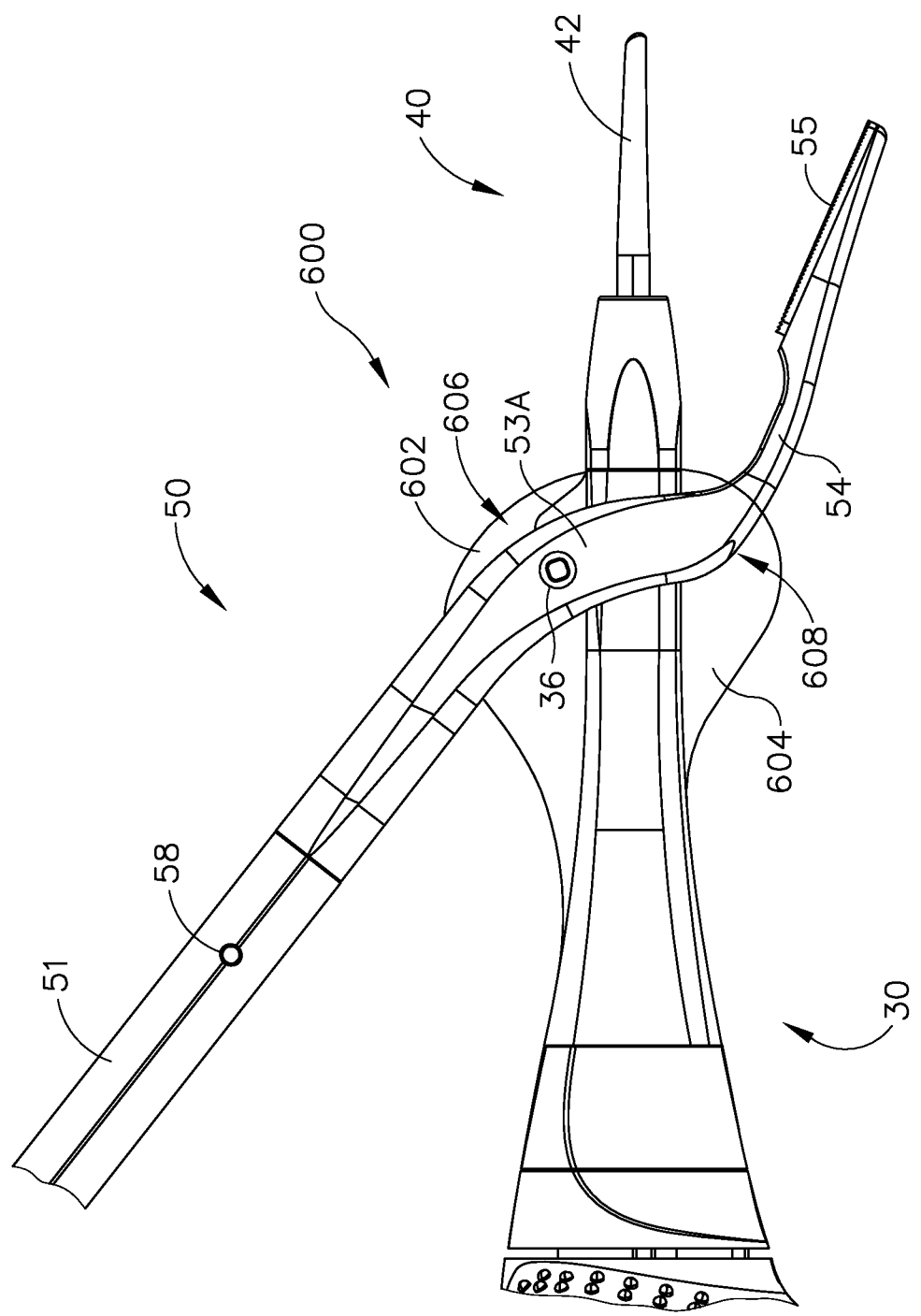
FIG. 31A depicts a side elevational view of the distal end configuration of FIG. 30, in an open position.
Figure 31B:
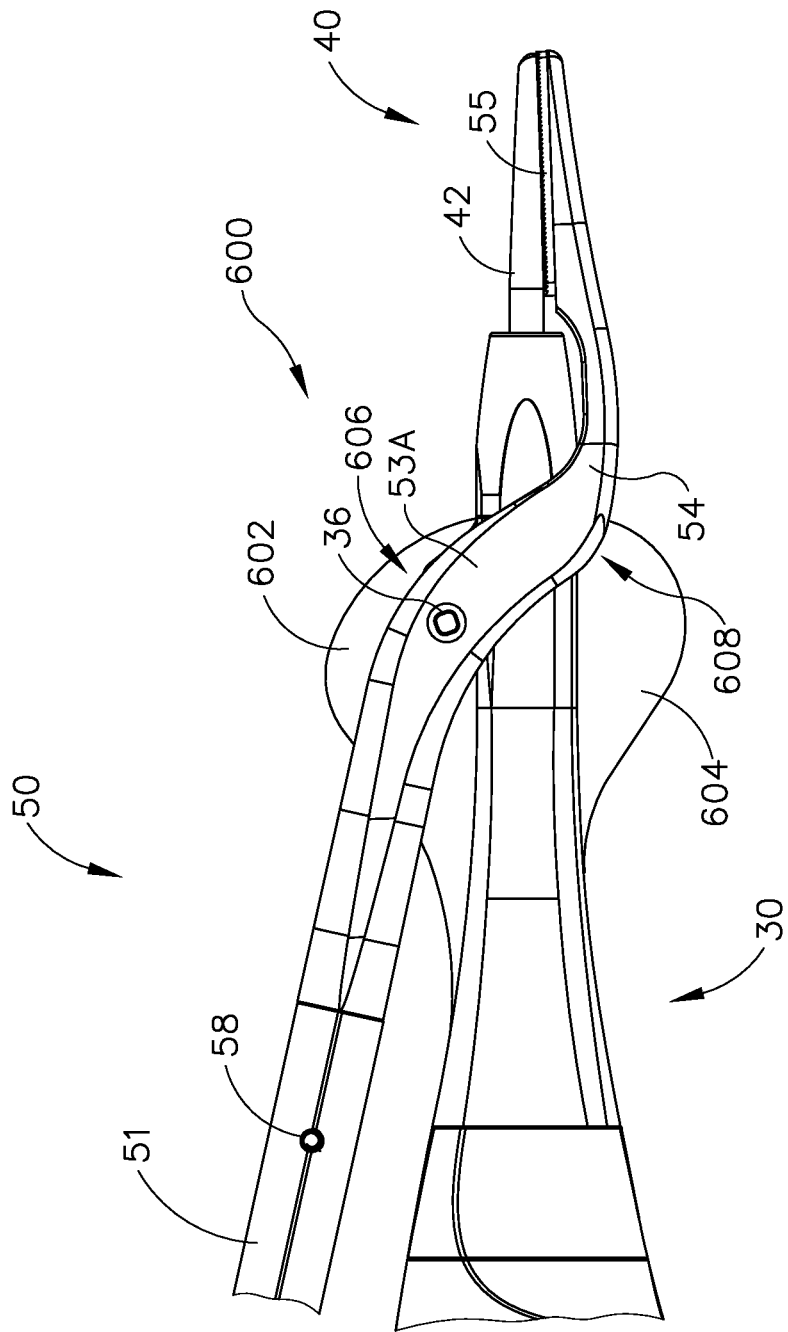
FIG. 31B depicts a side elevational view of the distal end configuration of FIG. 30, in a closed position.

FIGS. 30-31B show yet another exemplary alternative guide feature (600) that is configured to guide clamp arm (54) such that clamp arm (54) and/or clamp pad (55) adequately and appropriately engage ultrasonic blade (42) as clamp arm (54) is pivoted toward ultrasonic blade (42). Guide feature (600) of this example comprises a pair of projections (602, 604). First projection (602) extends laterally from a top surface of shaft assembly (30). Second projection (604) extends laterally from an underside of shaft assembly (30). Projections (602, 604) have rounded profiles in the present example, to avoid snagging/tearing/etc. tissue during operation. Clamp arm (54) of the present example defines a pair of slots (606, 608) configured to slidably receive projections (602, 604). First slot (606) is formed in a portion of clamp arm (54) above shaft assembly (30) adjacent to first member (53A) and second member (53B). Second slot (608) is formed in a portion of clamp arm (54) below shaft assembly (30) adjacent to first member (53A) and second member (53B). Thus, it should be understood that first slot (606) is configured to receive first projection (602) and second slot (608) is configured to receive second projection (604). It should also be understood that an interior width of slots (606, 608) may complement an exterior width of projections (602, 604) to thereby guide clamp arm (54) and clamp pad (55) into alignment with ultrasonic blade (42) as clamp arm (54) is pivoted toward ultrasonic blade (42).

In some versions, the interior width of slots (606, 608) and/or the exterior width of projections (602, 604) is inclined such that as clamp arm (54) is pivoted toward ultrasonic blade (42), projections (602, 604) more tightly fit within slots (606, 608) to thereby guide clamp arm (54) and clamp pad (55) as clamp arm (54) is pivoted toward ultrasonic blade (42). In other words, the walls of slots (606, 608) may bear against projections (602, 604) with progressively increasing force as clamp arm (54) is pivoted toward ultrasonic blade (42).

H. Eighth Exemplary Guide Feature

Figure 32:
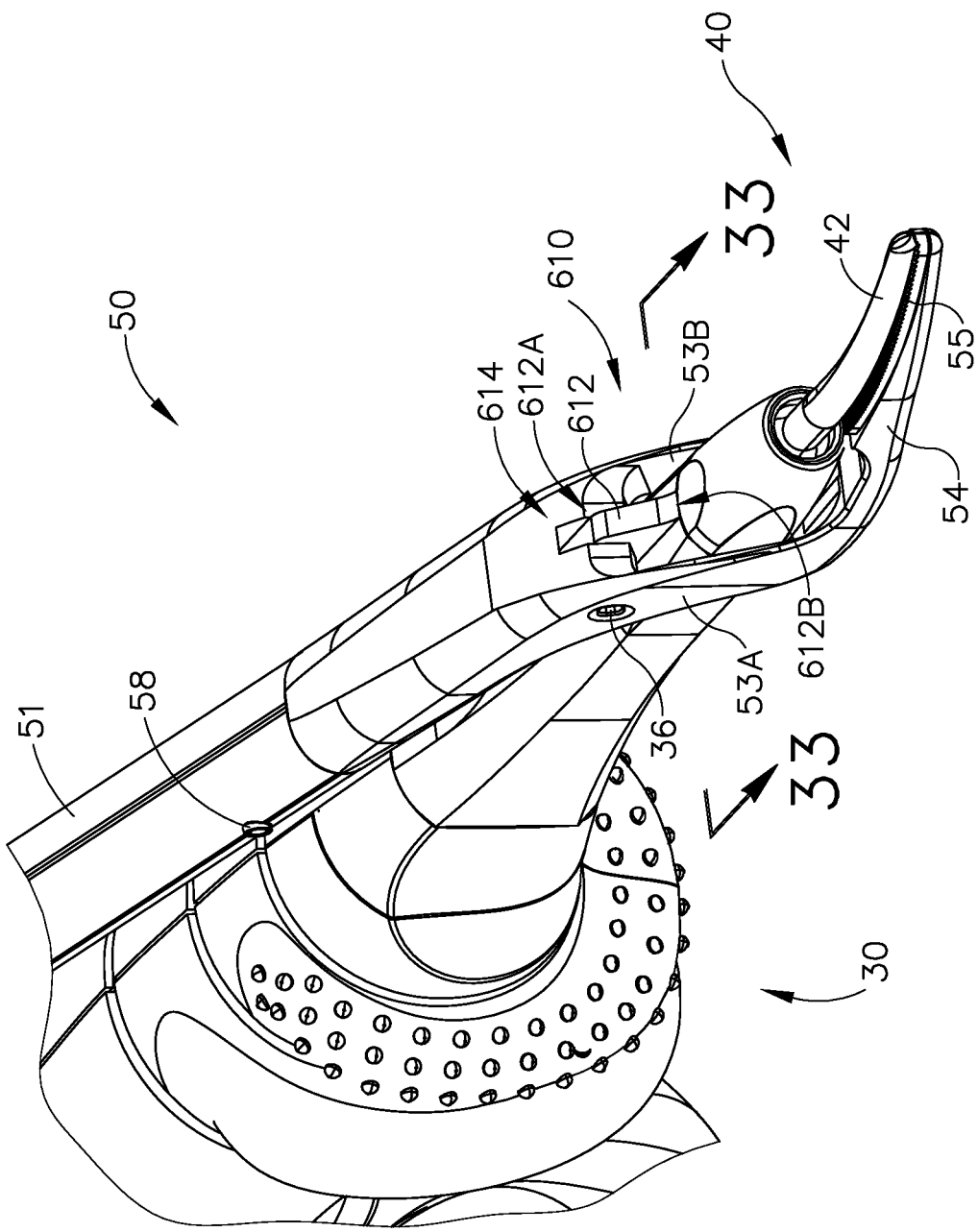
FIG. 32 depicts a perspective view of a version of the distal end of the instrument of FIG. 1 with other exemplary alternative guide features.
Figure 33:
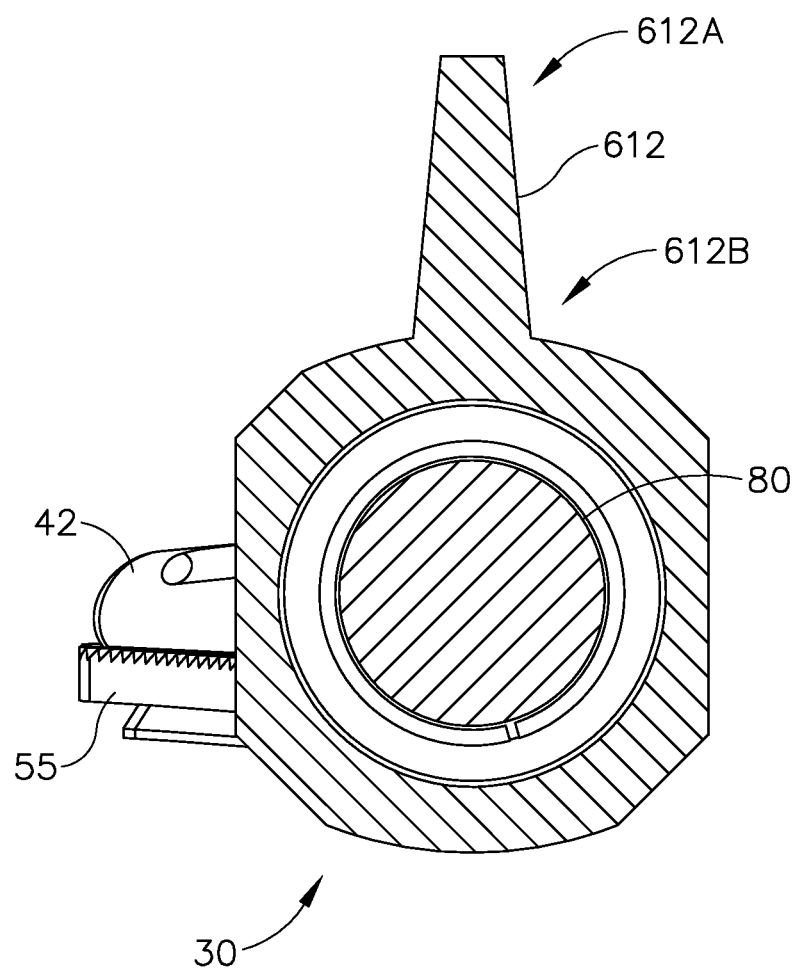
FIG. 33 depicts a cross-sectional view of the distal end configuration of FIG. 32 taken along line 33-33 of FIG. 32, with the clamp arm omitted.
Figure 34:
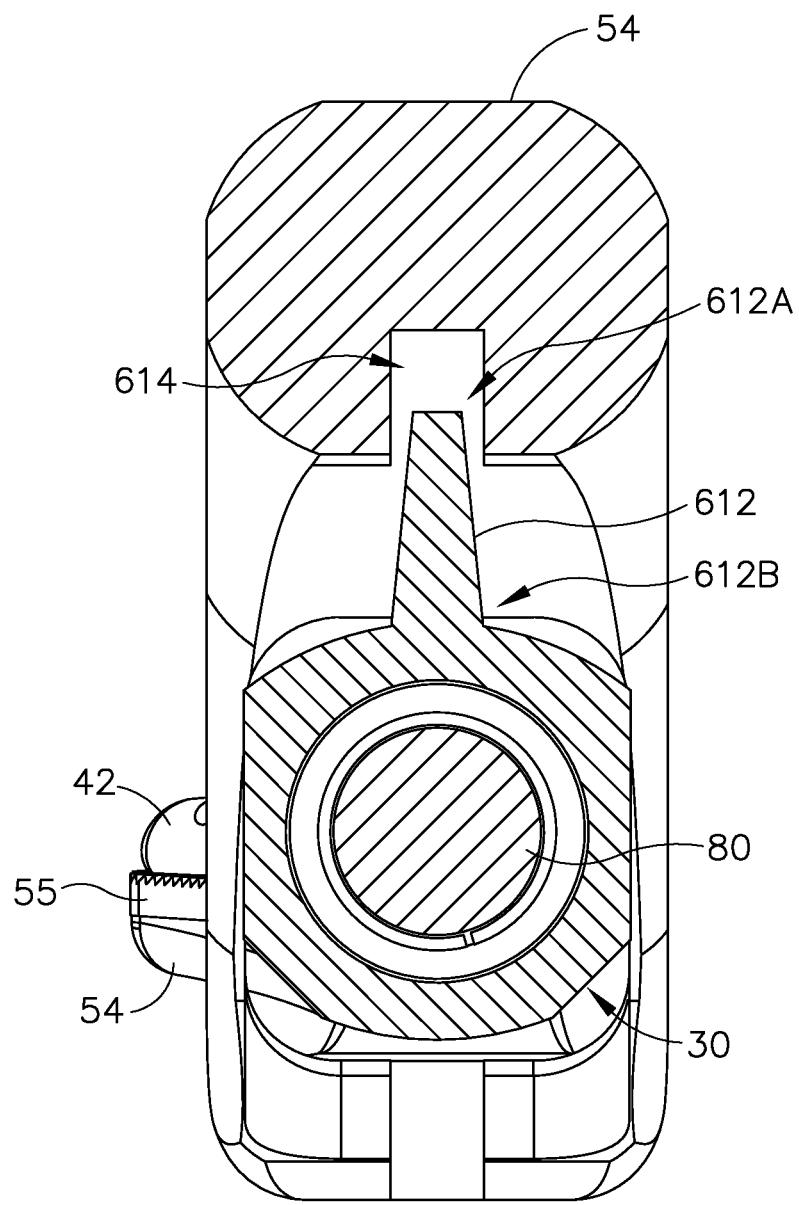
FIG. 34 depicts a cross-sectional view of the distal end configuration of FIG. 32 taken along line 33-33 of FIG. 32, with the clamp arm included.

FIGS. 32-34 show yet another exemplary alternative guide feature (610) that is configured to guide clamp arm (54) such that clamp arm (54) and/or clamp pad (55) adequately and appropriately engage ultrasonic blade (42) as clamp arm (54) is pivoted toward ultrasonic blade (42). Guide feature (610) of this example comprises a tapered projection (612) extending transversely from the top surface of shaft assembly (30). Clamp arm (54) of the present example defines a slot (614) configured to slidably receive tapered projection (612). Slot (614) has a substantially consistent lateral width throughout its entire depth. Slot (614) is formed in a portion of clamp arm (54) above shaft assembly (30) adjacent to first member (53A) and second member (53B). Thus, it should be understood that slot (614) is configured to receive tapered projection (612) as clamp arm (54) is pivoted toward ultrasonic blade (42).

As best seen in FIG. 34, an exterior surface of tapered projection (612) is shaped such that a top portion (612A) has an exterior width that is less that an interior width of slot (614); and such that a bottom portion (612B) has an exterior width substantially similar to or slightly greater than the interior width of slot (614). Thus, it should be understood that as clamp arm (54) is pivoted toward ultrasonic blade (42), the exterior width of tapered projection (612) more closely fits within slot (614) to thereby guide clamp arm (54) and clamp pad (55) as clamp arm (54) is pivoted toward ultrasonic blade (42). In other words, the outer surfaces of projection (612) bear against the walls of slot (614) with progressively increasing force as clamp arm (54) is pivoted toward ultrasonic blade (42).

III. Exemplary Waveguide Alignment Features

While the examples described above relate to providing adequate lateral and rotational alignment of clamp arm (54) relative to ultrasonic blade (42), it should be understood that it may be desirable to provide other forms of component alignment within instrument (10), to further address the relative positioning of blade (42) and clamp arm (54). For instance, it may be desirable to ensure that ultrasonic blade (42) is oriented at an appropriate angle about the longitudinal axis of ultrasonic blade (42), relative to clamp arm (54) and handpiece (20). This may be particularly so when ultrasonic blade (42) has an asymmetric cross-sectional profile. Referring back to FIG. 6, ultrasonic blade (42) of the present example has an elongate groove (43) running along one quadrant of ultrasonic blade (42), such that ultrasonic blade (42) of the present example has an asymmetric cross-sectional profile. Proper angular alignment of ultrasonic blade (42) may thus ensure proper positioning of groove (43) in relation to clamp pad (55) (e.g., to ensure that an upper edge (45) of groove (43) is diametrically opposed to clamp pad (55), to ensure that a particular surface (44) of ultrasonic blade (42) is parallel to an opposing surface of clamp pad (55), to ensure that the flat surface of clamp pad (55) is perpendicular to the curvature of a curved surface of ultrasonic blade (42) in order to reduce variability in the resultant tissue effects, etc.).

In view of the foregoing, it may be desirable to provide features that allow an operator or assembler to rotate and selectively "lock" blade (42) during assembly of instrument (10) such that ultrasonic blade (42) is oriented at an appropriate angle about the longitudinal axis of ultrasonic blade (42), relative to clamp arm (54) and handpiece (20). Several merely illustrative examples of such alignment features are described in detail below, while other examples will be apparent to those of ordinary skill in the art in view of the teachings herein.

A. First Exemplary Waveguide Alignment Feature

FIGS. 35-36 show an exemplary waveguide (702) having a plurality of teeth (704) disposed in a radial pattern about an exterior circumference of waveguide (702). In the example shown in FIGS. 35-36, teeth (704) are unitarily formed in the metallic material of waveguide (702). FIG. 37 shows an exemplary alternative waveguide (710) having teeth (712) that are configured similar to teeth (704) of waveguide (702) and operate similar to teeth (704) of waveguide (702). However, teeth (712) of waveguide (710) are formed by molding a second material (e.g., polycarbonate or other form of plastic, etc.) about a portion of waveguide (710). Waveguide (710) presents a through-hole (716) to provide for better adherence between waveguide (710) and molded material (714). Furthermore, an exterior circumference of waveguide (710) comprises a plurality of outwardly projecting features (718) to promote adherence between waveguide (710) and molded material (714). It should be understood that teeth (704, 712) may be centered at a position corresponding to a node associated with resonant ultrasonic vibrations communicated through waveguide (702, 710).

Figure 38A:
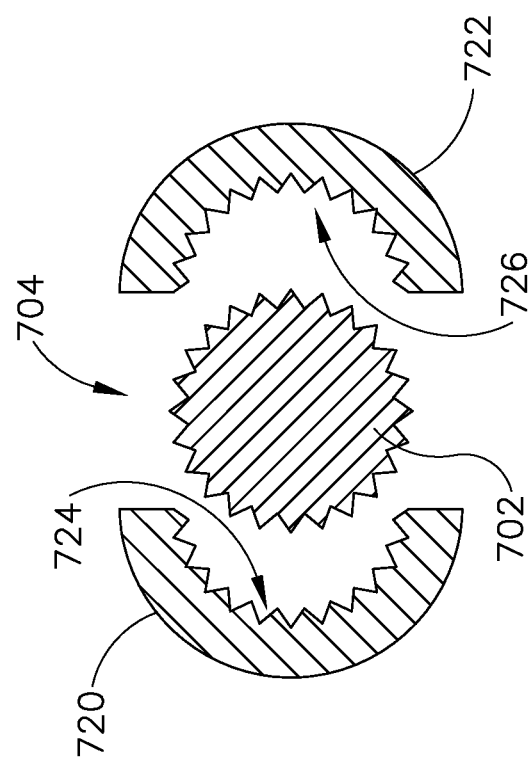
FIG. 38A depicts a cross-sectional view of the waveguide of FIG. 35 taken along line 36-36 of FIG. 35, with an exemplary locking feature in an open position.
Figure 38B:
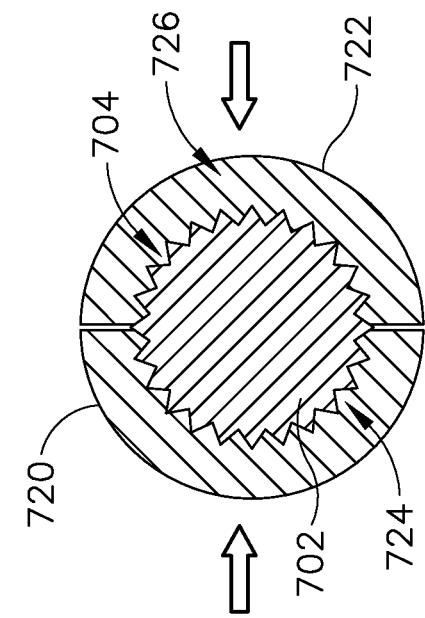
FIG. 38B depicts a cross-sectional view of the waveguide of FIG. 35 taken along line 36-36 of FIG. 35, with the locking feature of FIG. 38A in a closed position.

FIGS. 38A-39B show teeth (704) selectively engaging a plurality of locking members (720, 722, 730, 732, 734) to thereby prevent waveguide (702) from rotating about the longitudinal axis of waveguide (702) relative to clamp arm (54) and handpiece (20). While waveguide (702) is shown in FIGS. 38A-39B, it should be understood that waveguide (702) may be readily replaced with waveguide (710) and/or other alternatives. Referring specifically to FIGS. 38A-38B, locking members (720, 722) each comprise a semi-circular body having an exterior circumference and an interior circumference. Locking members (720, 722) may be formed as integral features of body (22) or may otherwise be mechanically grounded relative to body (22). Locking members (720, 722) comprise a plurality of teeth (724, 726) disposed in a radial pattern about the interior circumferences of locking members (720, 722). Teeth (724, 726) of locking members (720, 722) are configured to engage teeth (704) of waveguide (702) when locking members (720, 722) are in a closed position as shown in FIG. 38B. Teeth (724, 726) of locking members (720, 722) are configured to disengage teeth (704) of waveguide (702) when locking members (720, 722) are in an open position as shown in FIG. 38A.

During assembly of instrument (10), with locking members (720, 722) in the open position, an operator or assembler may rotate waveguide (702) such that a surface (44) that is perpendicular to the curvature of blade (42) is adequately aligned with the top surface of clamp pad (55), such that upper edge (45) of groove (43) is diametrically opposed to clamp pad (55), or such that any other suitable orientation of blade (42) is achieved. With blade (42) held at a desired angular orientation, locking members (720, 722) may be secured in the closed position to thereby "lock" waveguide (702), and thus blade (42), in position. By way of example only, locking members (720, 722) may be secured in place using welding, adhesive, snap fitting, clamps, clips, rings, and/or any other suitable components/techniques.

While locking members (720, 722) of the present example comprise a plurality of teeth (724, 726), it should be understood that any number of teeth may be used. For instance, teeth (724, 726) may comprise a single tooth. Furthermore, other suitable configurations may be used instead of teeth (724, 726), including but not limited to complementary hex features, etc. It should also be understood that although two locking members (720, 722) are used in the present example, any number of locking members (720, 722) may be used.

Figure 39A:
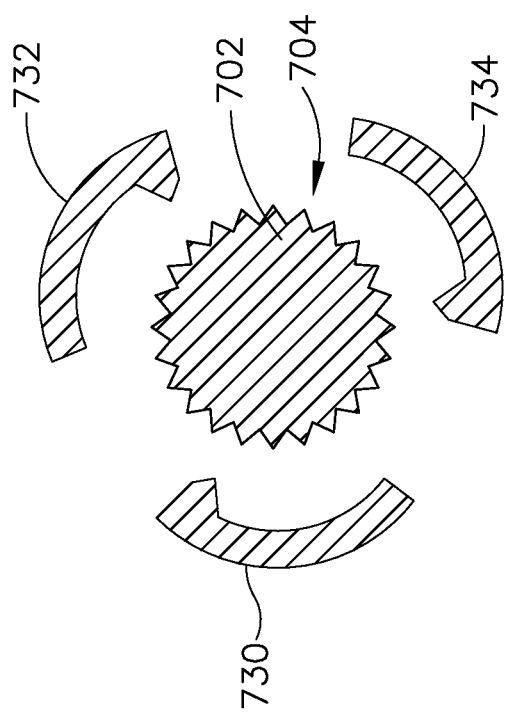
FIG. 39A depicts a cross-sectional view of the waveguide of FIG. 35 taken along line 36-36 of FIG. 35, with an exemplary alternative locking feature in an open position.
Figure 39B:
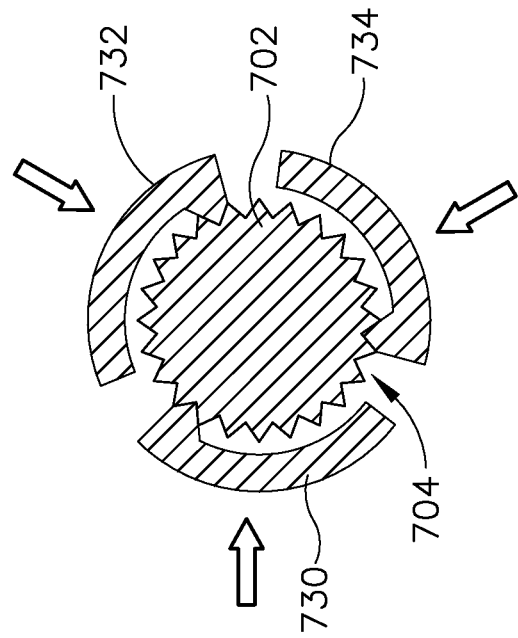
FIG. 39B depicts a cross-sectional view of the waveguide of FIG. 35 taken along line 36-36 of FIG. 35, with the locking feature of FIG. 39A in a closed position.

FIGS. 39A-39B show additional exemplary locking members (730, 732, 734). Locking members (730, 732, 734) of this example each comprise a partial-circle body having an exterior circumference and an interior circumference. Locking members ((730, 732, 734) may be formed as integral features of body (22) or may otherwise be mechanically grounded relative to body (22). Each locking member (730, 732, 734) has a single tooth (736, 738, 740) projecting inwardly from the interior circumference of locking members (730, 732, 734). Teeth (736, 738, 740) of locking members (730, 732, 734) are configured to engage plurality of teeth (704) of waveguide (702) when locking members (730, 732, 734) are in a closed position as shown in FIG. 39B. Teeth (736, 738, 740) of locking members (730, 732, 734) are configured to disengage plurality of teeth (704) of waveguide (702) when locking members (730, 732, 734) are in an open position as shown in FIG. 39A. During assembly of instrument (10), with locking members (730, 732, 734) in the open position, an operator or assembler may rotate waveguide (702) such that a surface (44) that is perpendicular to the curvature of blade (42) is adequately aligned with the top surface of clamp pad (55), such that upper edge (45) of groove (43) is diametrically opposed to clamp pad (55), or such that any other suitable orientation of blade (42) is achieved. With blade (42) held at a desired angular orientation, locking members (730, 732, 734) may be secured in the closed position to thereby "lock" waveguide (702) and thus blade (42) in position. By way of example only, locking members (730, 732, 734) may be secured in place using welding, adhesive, snap fitting, clamps, clips, rings, and/or any other suitable components/techniques.

B. Second Exemplary Waveguide Alignment Feature

Figure 40A:
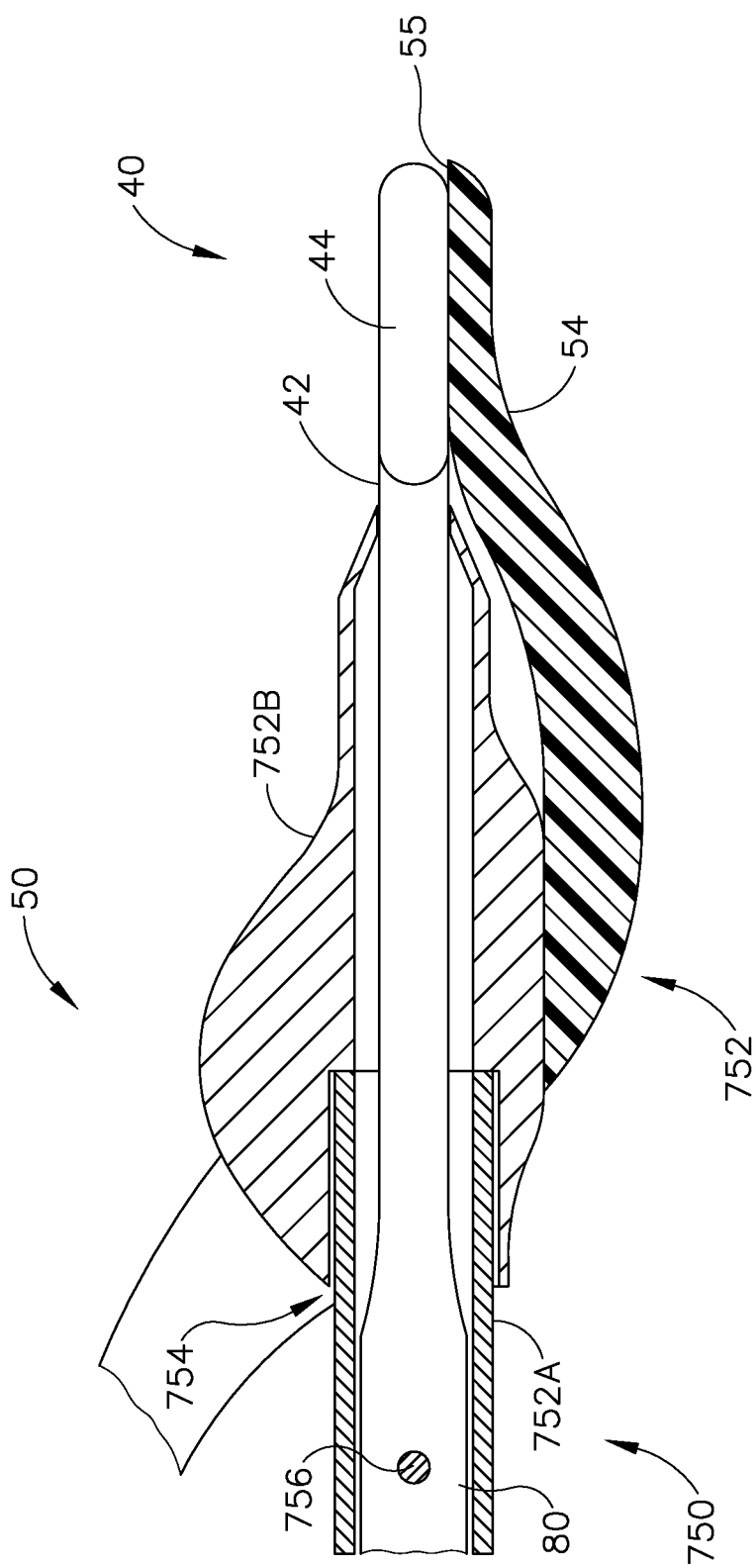
FIG. 40A depicts a cross-sectional view of an exemplary alternative version of the distal end of the instrument of FIG. 1, with an exemplary waveguide and exemplary rotation member in a first rotational position.
Figure 40B:
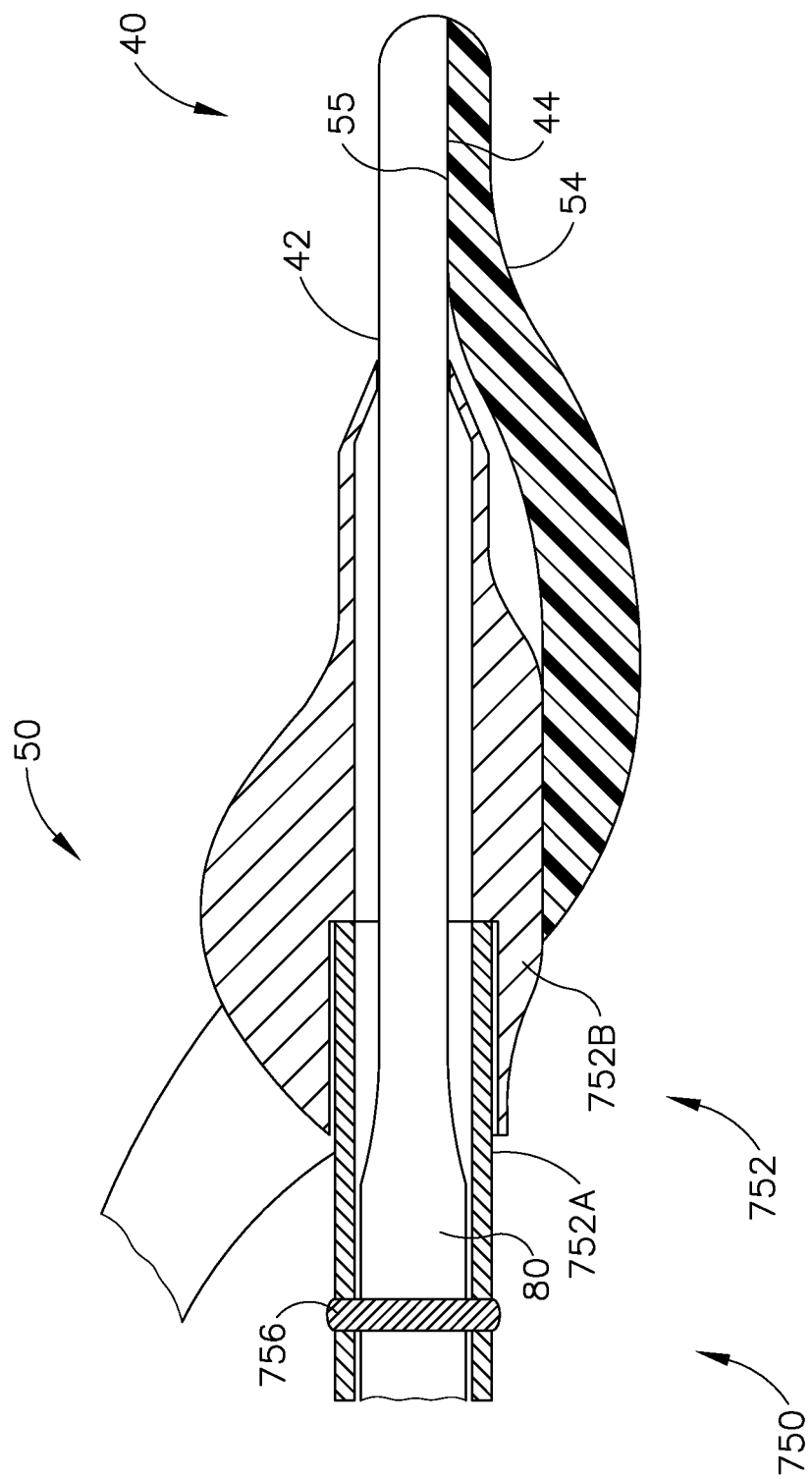
FIG. 40B depicts a cross-sectional view of the distal end configuration of FIG. 40A, with the waveguide and rotation member in a second rotational position.

FIGS. 40A-40B show an exemplary alternative alignment feature (750) that is configured to allow waveguide (80) to be rotated and then locked relative to handpiece (20) to ensure that ultrasonic blade (42) is oriented at an appropriate angle about the longitudinal axis of ultrasonic blade (42), relative to clamp arm (54) and handpiece (20). Alignment feature (750) of this example comprises an exemplary alternative shaft assembly (752). Shaft assembly (752) comprises a proximal member (752A) and a distal member (752B). A distal portion of proximal member (752A) is rotatably disposed within a proximal recess (754) of distal member (752B) such that proximal member (752A) may be rotated within distal member (752B). Proximal member (752A) and distal member (752B) each present an interior bore through which waveguide (80) is disposed. Waveguide (80) is secured to proximal member (752A) via a pin (756) that passes through waveguide (80) and into proximal member (752A). Waveguide (80) and proximal member (752A) are thus configured to rotate unitarily. Pin (756) is located at a position along the length of waveguide (80) corresponding to a node associated with resonant ultrasonic vibrations communicated through waveguide (80).

As shown in FIG. 40A, during assembly, flat surface (44) of blade (42) may initially be mis-aligned relative to the top surface of clamp pad (55). With proximal member (752A) positioned within distal recess (754) of distal member (752B), proximal member (752A) may be rotated to thereby rotate waveguide (80) and blade (42) such that flat surface (44) of blade (42) may be adequately aligned parallel with the top surface of clamp pad (55), as shown in FIG. 40B. With blade (42) properly aligned, proximal member (752A) and distal member (752B) may be secured together by welding, adhesives, and/or using any other suitable features or techniques. With proximal member (752A) and distal member (752B) secured together, they cooperate to "lock" waveguide (80), and thus blade (42), in the desired angular position relative to clamp pad (55) and handpiece (20). In some variations, the distal end of proximal member (752A) comprises outwardly projecting teeth (e.g., similar to teeth (704, 712), etc.) and the proximal end of distal member (752B) comprises complementary teeth (e.g., similar to teeth (724, 726, 736, 738, 740), etc.). Thus, proximal member (752A) may be initially spaced apart from distal member (752B) as waveguide (80) is rotated to achieve the desired angular alignment, and then proximal member (752A) may be advanced distally into distal member (752B) such that the complementary teeth mesh to secure the desired angular positioning.

C. Third Exemplary Alternative Waveguide Alignment Feature

Figure 41A:
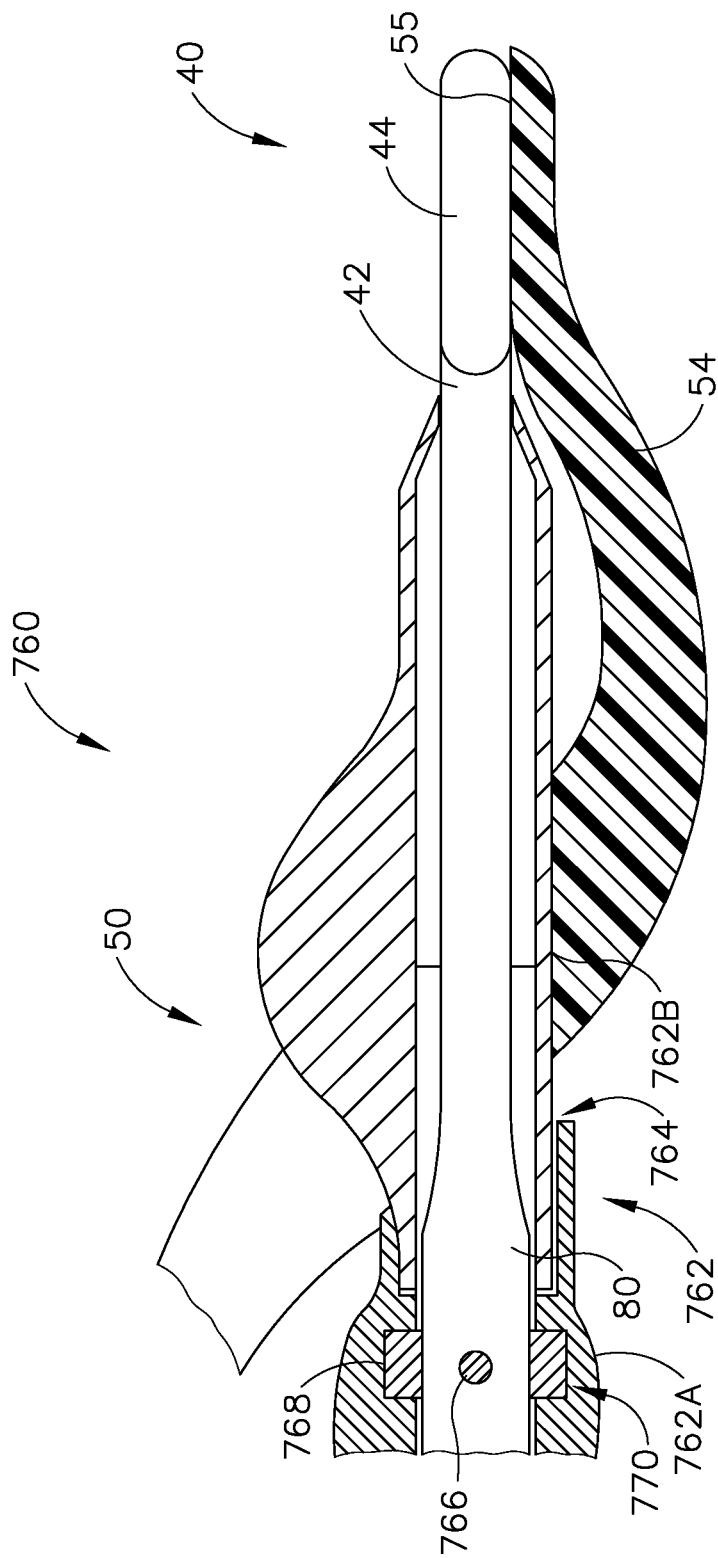
FIG. 41A depicts a cross-sectional view of another exemplary alternative version of the distal end of the instrument of FIG. 1, with an exemplary waveguide and exemplary rotation member in a first rotational position.
Figure 41B:
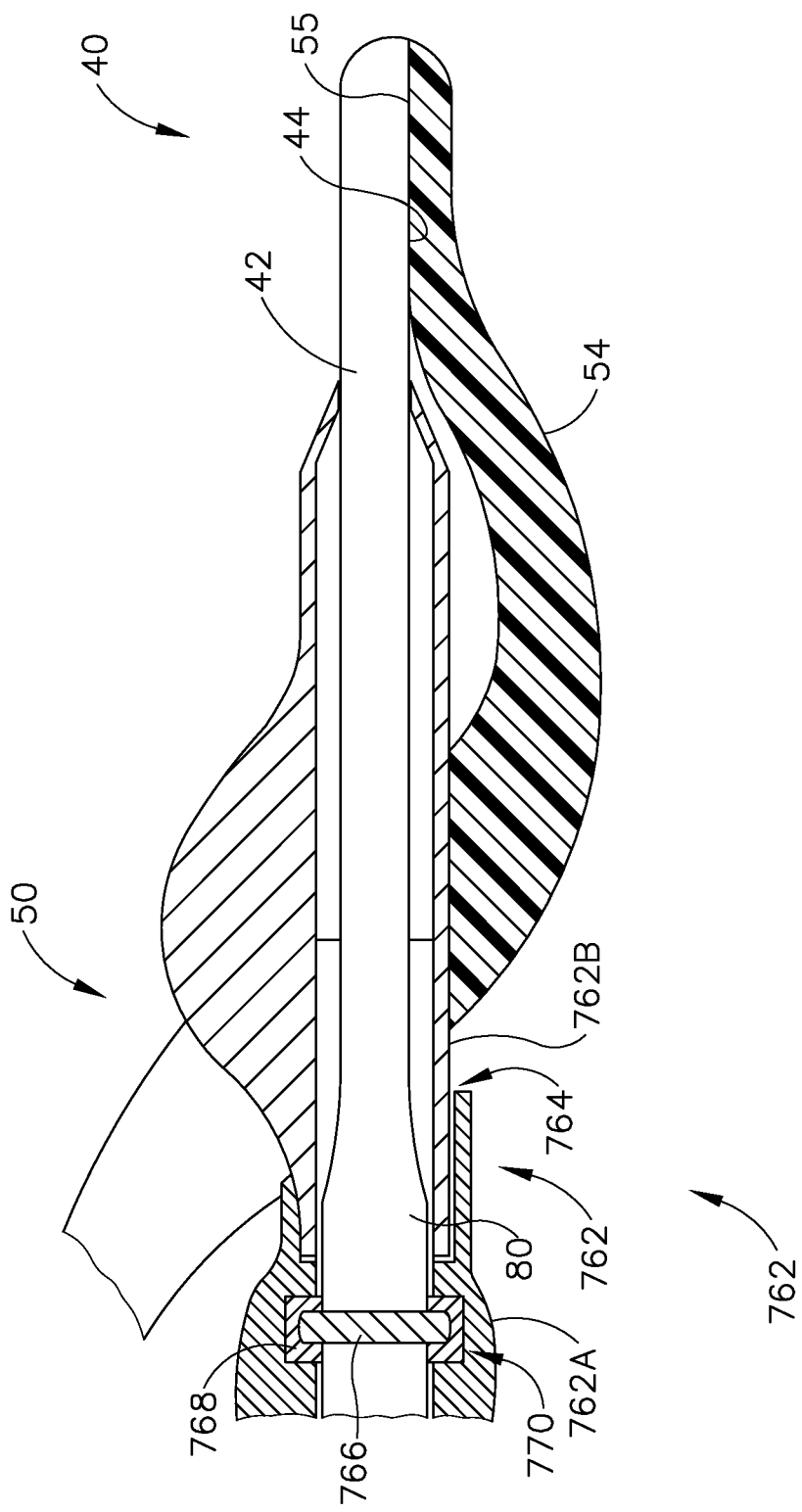
FIG. 41B depicts a cross-sectional view of the distal end configuration of FIG. 41A, with the waveguide and rotation member in a second rotational position.

FIGS. 41A-41B show another exemplary alternative alignment feature (760) that is configured to allow waveguide (80) to be rotated and then locked relative to handpiece (20) to ensure that ultrasonic blade (42) is oriented at an appropriate angle about the longitudinal axis of ultrasonic blade (42), relative to clamp arm (54) and handpiece (20). Alignment feature (750) of this example is configured to operate substantially similar to alignment features (700) discussed above except for the differences discussed below. In particular, alignment feature (760) is configured to allow an operator or assembler to rotate waveguide (80) relative to shaft assembly (30) during assembly of instrument (10) such that ultrasonic blade (42) is oriented at an appropriate angle about the longitudinal axis of ultrasonic blade (42), relative to clamp arm (54) and handpiece (20).

Alignment feature (760) of this example comprises an exemplary alternative shaft assembly (762). Shaft assembly (762) comprises a proximal member (762A) and a distal member (762B). A proximal portion of distal member (762B) is rotatably disposed within a distal recess (764) of proximal member (762A) such that distal member (762B) may be rotated within proximal member (762A). Proximal member (762A) and distal member (762B) each present an interior bore through which waveguide (80) is disposed. A rotatable ring (768) is disposed within an annular recess (770) formed within an interior surface of proximal member (762A) such that ring (768) is rotatable relative to proximal member (762A). Waveguide (80) is secured to ring (768) via a pin (766) that passes through waveguide (80) and into ring (768). Waveguide (80) and ring (768) are thus configured to rotate unitarily. Pin (766) is located at a position along the length of waveguide (80) corresponding to a node associated with resonant ultrasonic vibrations communicated through waveguide (80).

As shown in FIG. 41A, during assembly, flat surface (44) of blade (42) may initially be mis-aligned relative to the top surface of clamp pad (55). With distal member (762B) secured within proximal recess (764) of proximal member (762A), ring (768) may be rotated to thereby rotate waveguide (80) and blade (42) such that flat surface (44) of blade (42) may be adequately aligned parallel with the top surface of clamp pad (55) as shown in FIG. 41B. With blade (42) properly aligned, ring (768) may be secured to proximal member (762A) by welding, adhesives, and/or using any other suitable features or techniques. With ring (768) and proximal member (762A) secured together, they cooperate to "lock" waveguide (80), and thus blade (42), in the desired angular position relative to clamp pad (55) and handpiece (20).

IV. Exemplary Clamp Arm Stiffness Adjustment Feature

Figure 42:
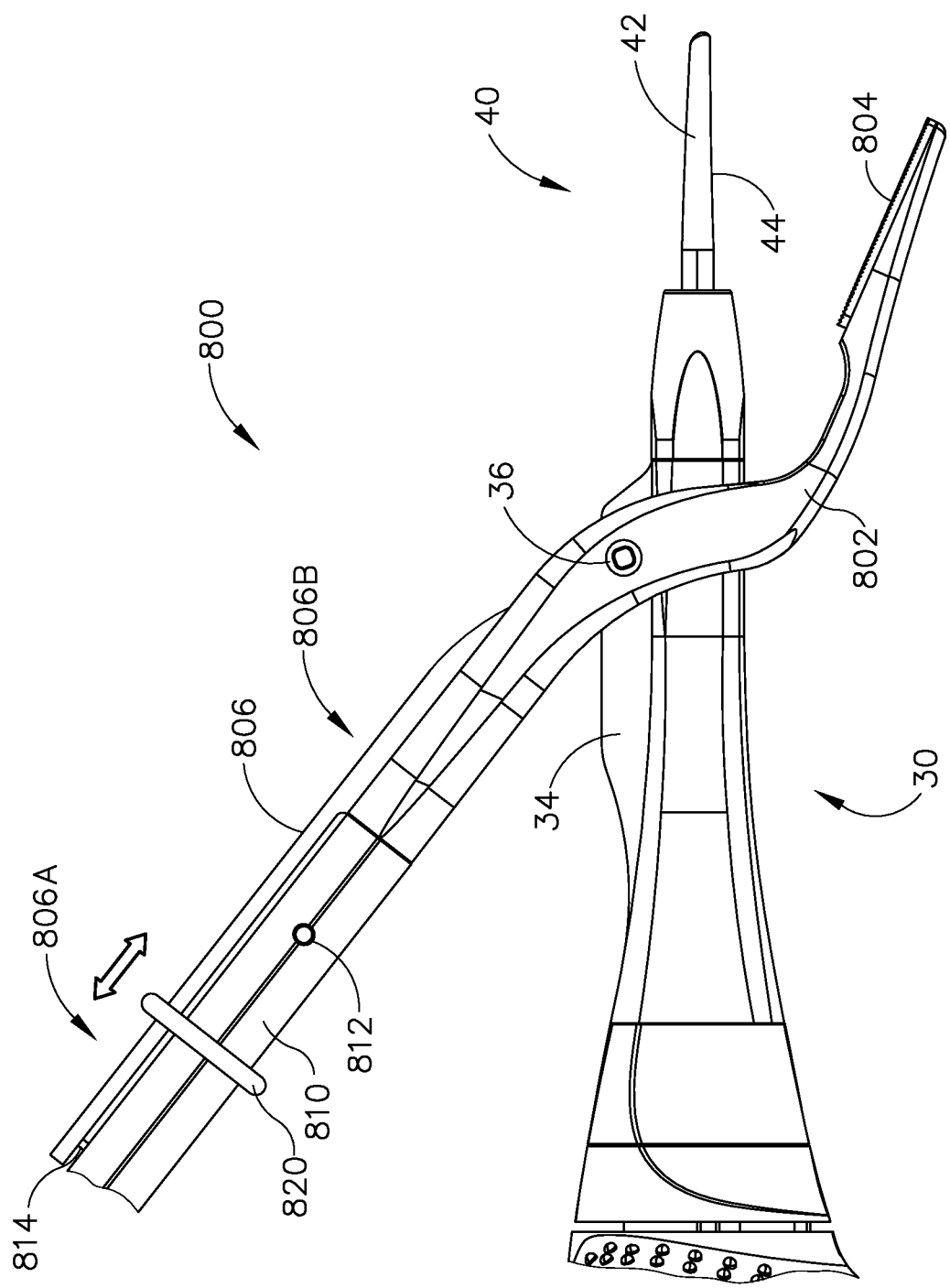
FIG. 42 depicts a side elevational view of another exemplary alternative version of the distal end of the instrument of FIG. 1, with an exemplary alternative clamp arm having a stiffening feature in an intermediate position.
Figure 43A:
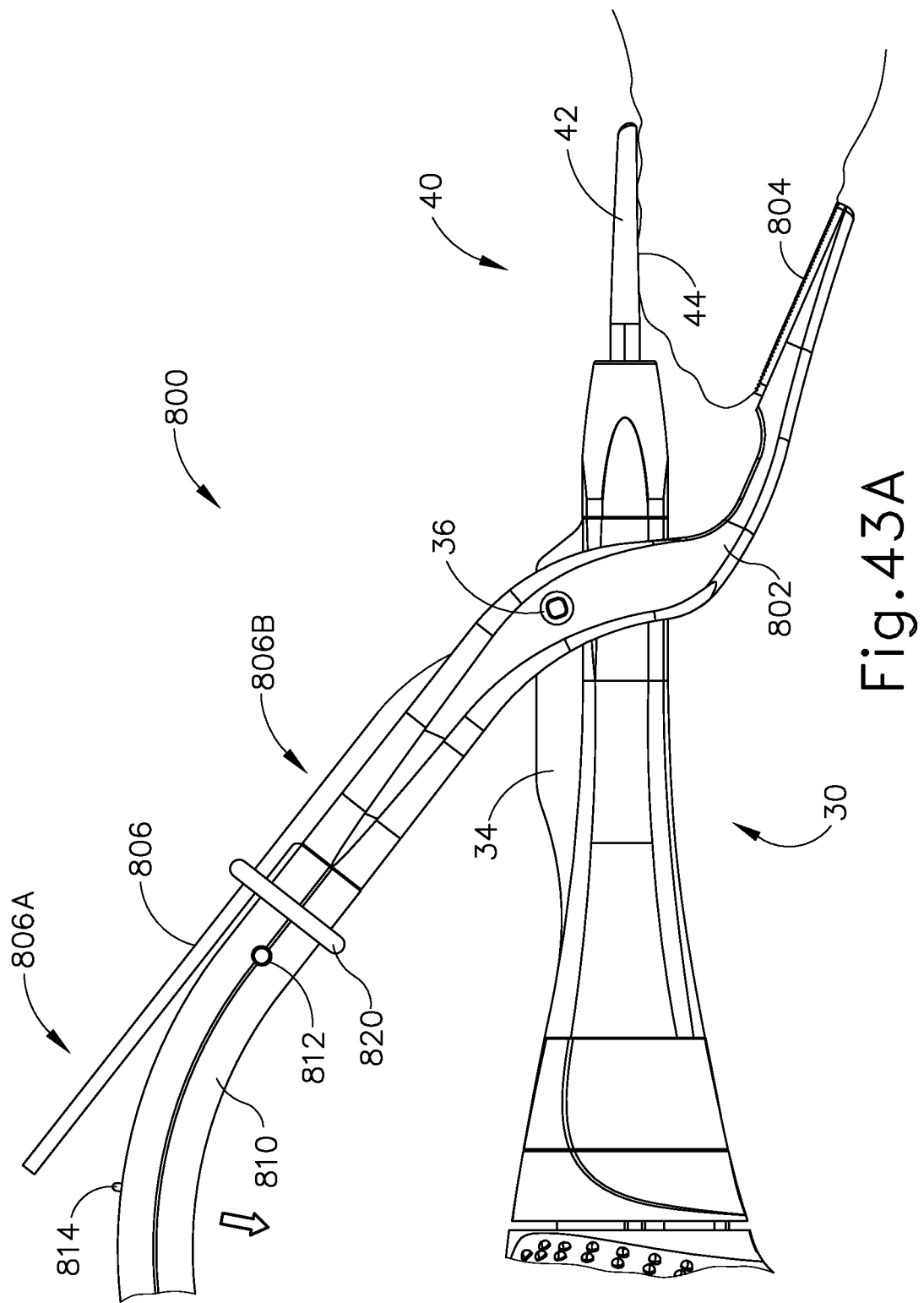
FIG. 43A depicts a side elevational view of distal end configuration of FIG. 42, with the stiffening feature in a distal position and the end effector positioned about tissue.
Figure 43B:
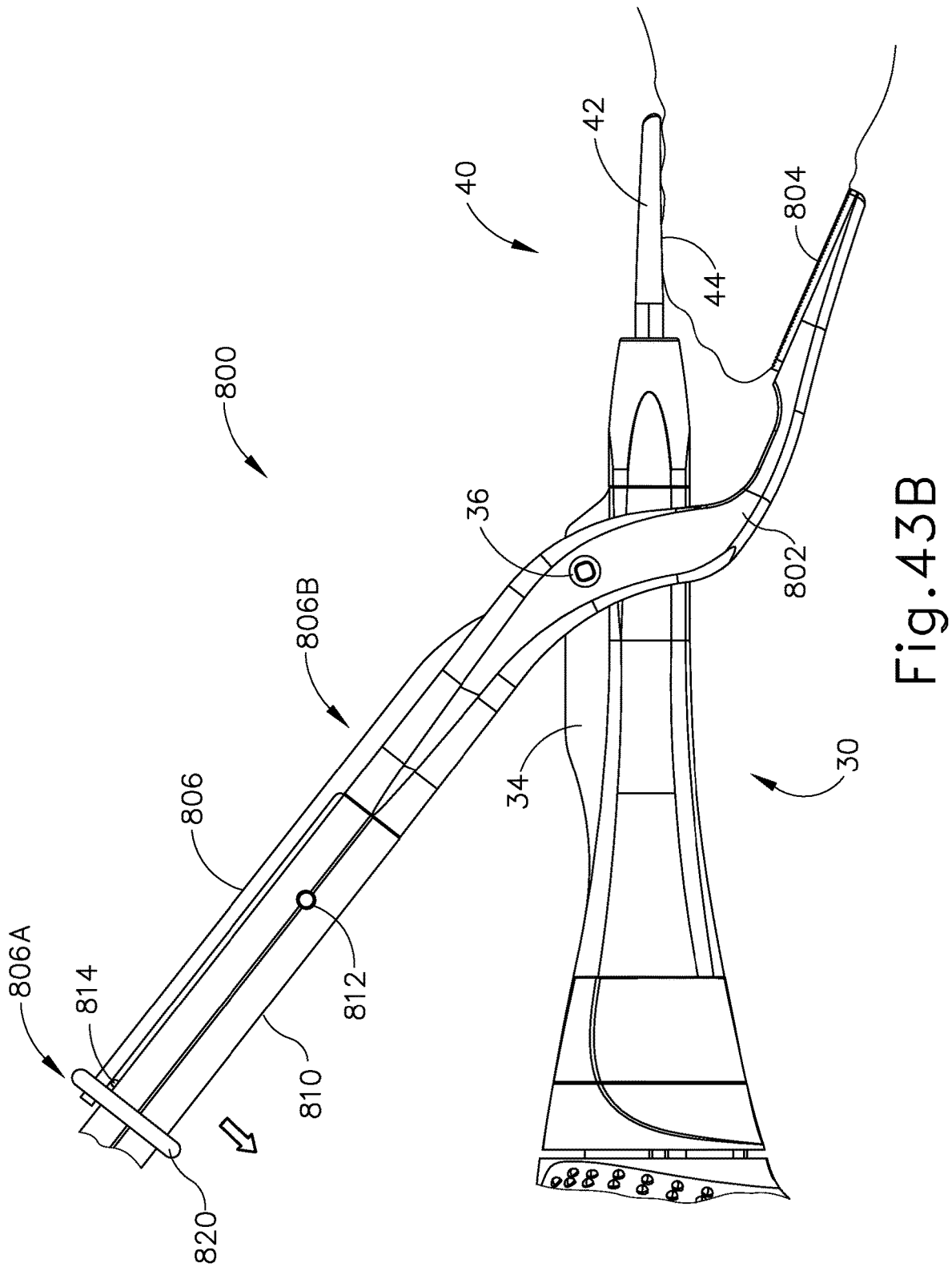
FIG. 43B depicts a side elevational view of distal end configuration of FIG. 42, with the stiffening feature in a proximal position and the end effector positioned about tissue.
Figure 43C:
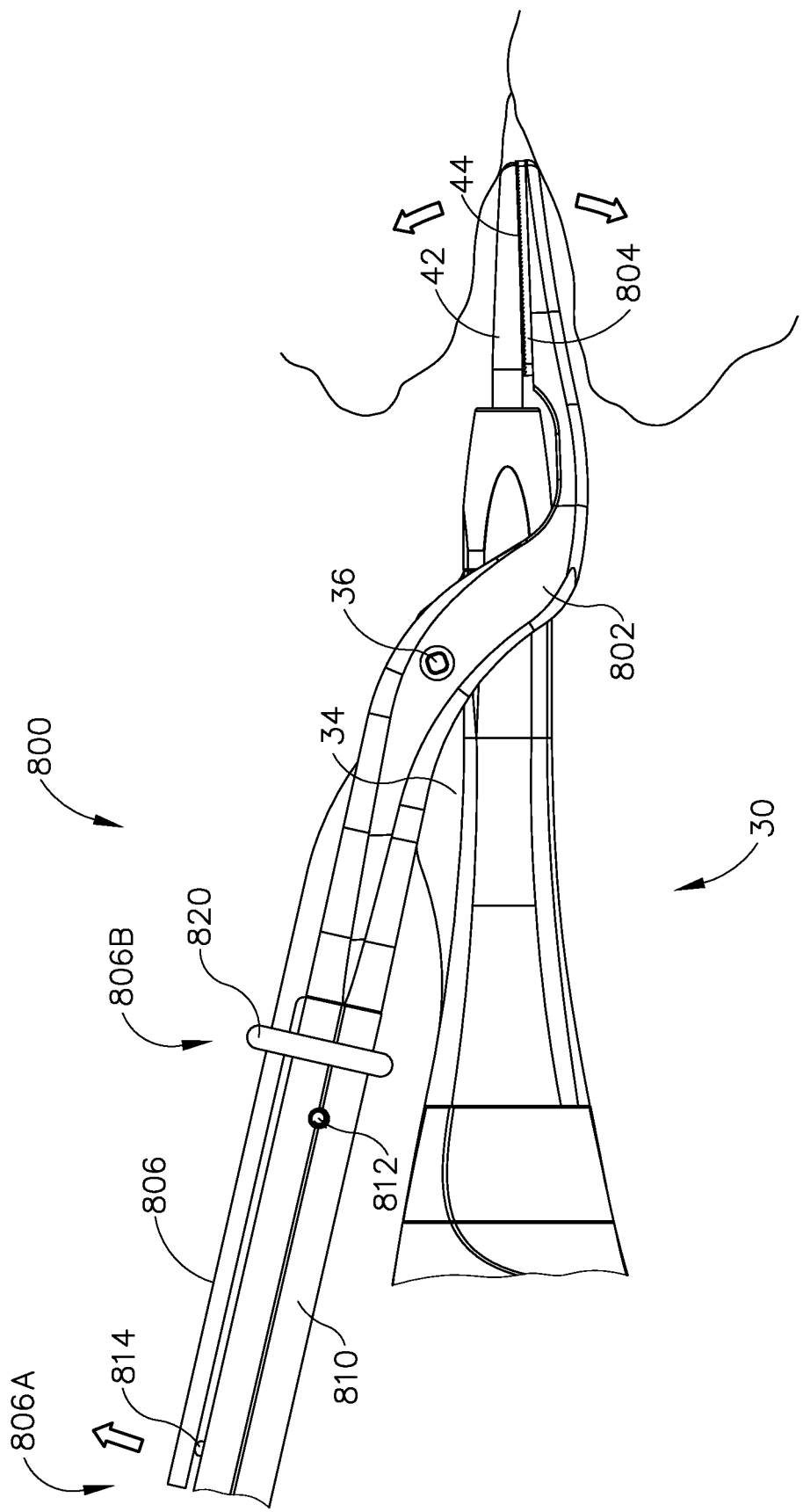
FIG. 43C depicts a side elevational view of distal end configuration of FIG. 42, with the stiffening feature in a distal position and the end effector positioned in tissue for blunt dissection.

It may be desirable to provide features that allow an operator to adjust a stiffness of clamp arm assembly (50). In addition or in the alternative, it may be desirable to provide a first stiffness when clamp arm assembly (50) is pivoted toward shaft assembly (30) and a second stiffness when clamp arm assembly (50) is pivoted away from shaft assembly (30). Merely exemplary stiffening features (800) that provide such varying stiffness are shown in FIGS. 42-43C. Stiffening features (800) comprise an exemplary alternative clamp arm (802) and arm shank (810). Clamp arm (802) of the present example is configured to operate substantially similar to clamp arm (54) discussed above except for the differences discussed below. For instance, clamp arm (802) is pivotable toward and away from ultrasonic blade (42) to thereby clamp tissue between a clamp pad (804) of clamp arm (802) and ultrasonic blade (42). A proximal end of clamp arm (802) is disposed within a distal recess (not shown) of arm shank (810) and secured therein by a pin (812) disposed through both arm shank (810) and clamp arm (802).

Clamp arm (802) comprises an integral stiffening rod (806), which extends proximally from a proximal portion of clamp arm (802) and parallel to arm shank (810). A ring (820) is slidably disposed about rod (806) and arm shank (810) such that ring (820) is slidable between a proximal portion (806A) of rod (806) (as shown in FIG. 43B) and a distal portion (806B) of rod (806) (as shown in FIG. 43A). It should be understood that as ring (820) slides relative to rod (806), ring (820) will also slide relative to arm shank (810) between a proximal position and a distal position.

Arm shank (810) of the present example is formed of a semi-rigid material (e.g., plastic), whereas rod (806) is formed of a more rigid material (e.g., metal). As shown in FIG. 43A, with ring (820) disposed about distal portion (806B) of rod (806), arm shank (810) is allowed to deform when arm shank (810) is driven toward shaft assembly (30) with sufficient force. It should be understood that, even with ring (820) in the distal position shown in FIG. 43A, arm shank (810) may still have sufficient rigidity to clamp tissue between clamp arm (802) and blade (42) with an appreciable amount of compression force. When ring (820) is slid to a proximal position where ring (820) is disposed about proximal portion (806A) of rod (806) as shown in FIG. 43B, ring (820) and rod (806) cooperate to provide more rigidity to arm shank (810), such that arm shank (810) will be relatively more stiff when clamping tissue between clamp pad (804) of clamp arm (802) and ultrasonic blade (42). It should be understood that ring (820) may be disposed about rod (806) and arm shank (810) at any longitudinal position between proximal portion (806A) and distal portion (806B) to selectively vary the effective rigidity of arm shank (810). It should also be understood that the selected effective rigidity of arm shank (810) will vary the maximum tissue clamping force provided through clamp arm assembly (50).

In some operations, it may be desirable to use instrument (10) to pry tissue apart using a blunt dissection technique. In such operations, an operator may use an outer surface of blade (42) and an outer surface of clamp arm (802) to pry tissue apart, such as by spreading rings (24, 52) apart. As shown in FIG. 43C, arm shank (810) comprises a tab (814) extending laterally from arm shank (810) within the gap between arm shank (810) and rod (806) such that proximal portion (806A) of rod (806) engages tab (814). It should therefore be understood that, even with ring (820) disposed about distal portion (806B) of rod (806), arm shank (810) will be relatively stiff when prying tissue apart using clamp arm (802) and ultrasonic blade (42) because arm shank (810) will receive significant stiffening support from rod (806). Thus, with ring (820) disposed about distal portion (806B) of rod (806), arm shank (810) will be relatively flexible when clamping tissue, but arm shank (810) will be relatively stiff when prying tissue apart without moving ring (820). In some versions, ring (820) is omitted entirely, with rod (806) still providing variable stiffness in arm shank (810) depending on whether clamp arm (802) is being driven toward or away from blade (42).

V. Exemplary Cutting Members

Figure 44B:
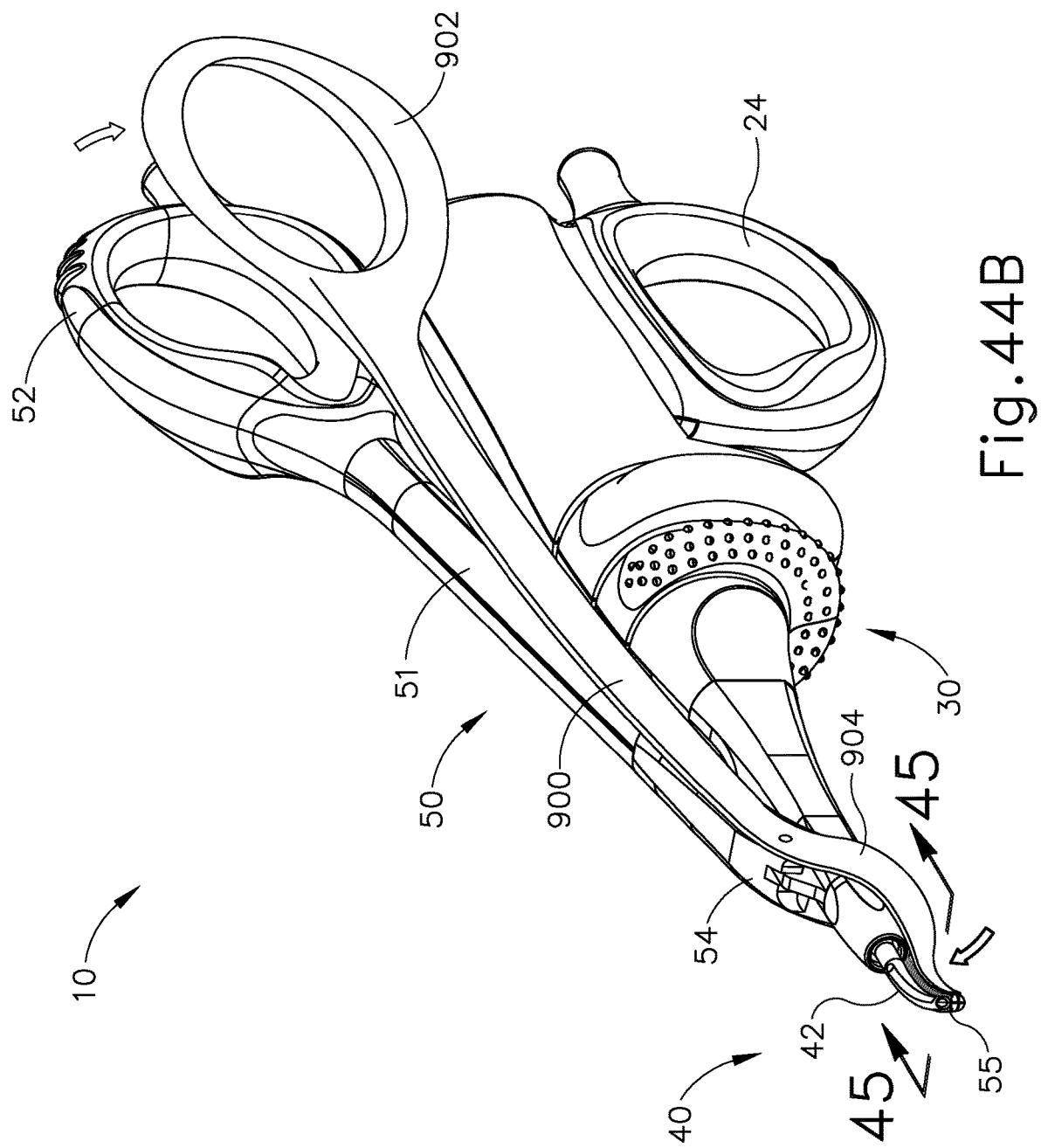
FIG. 44B depicts a perspective view of the instrument of FIG. 44A with the cutting member in a closed position.
Figure 45:
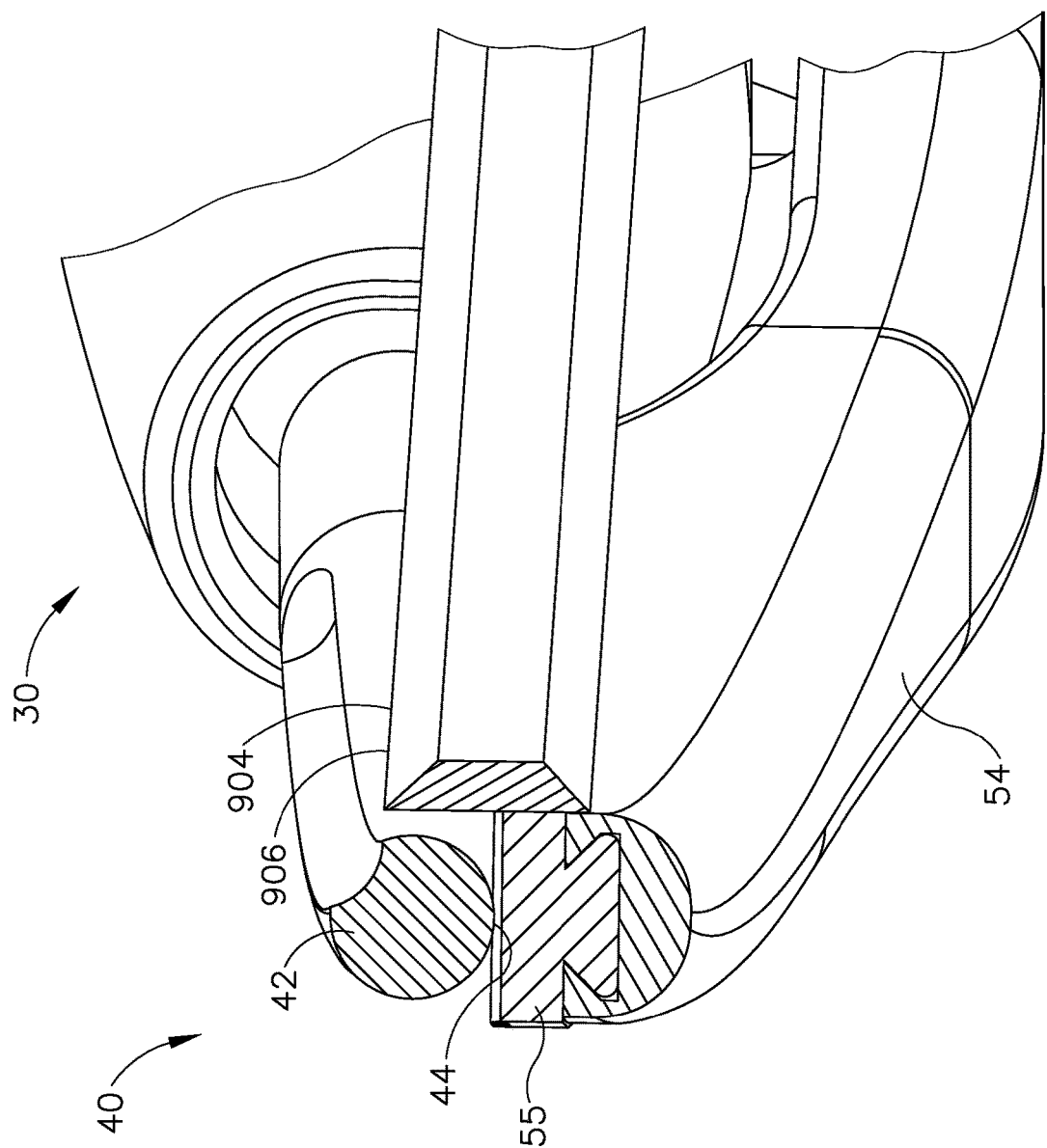
FIG. 45 depicts a cross-sectional view of the end effector of the instrument of FIG. 44A taken along line 45-45 of FIG. 44B.

As noted above, end effector (40) may be used to sever tissue using a combination of compression (between clamp pad (55) and ultrasonic blade (42)) and ultrasonic vibrations from blade (42). It may be desirable to provide additional tissue severing capability, such as with a shearing blade that is offset from blade (42) and clamp arm (54). FIGS. 44A-45 show a version of instrument (10) having an exemplary cutting member (900). Cutting member (900) is pivotably coupled with projection (34) of shaft assembly (30) such that cutting member (900) is pivotable relative to shaft assembly (30) from an open position (shown in FIG. 44A) to a closed position (shown in FIG. 44B). A proximal portion of cutting member (900) comprises a thumb grip (902). Thumb grip (902) and finger grip (24) together provide a scissor grip type of configuration. A distal portion of cutting member (900) comprises a blade (904) having a sharp edge (906).

As best seen in FIG. 45, when cutting member (900) is in a closed position, an interior surface of blade (904) is configured to slides closely to an exterior surface of clamp pad (55) such that blade (904) is operable to slice tissue clamped between clamp pad (55) of clamp arm (54) and ultrasonic blade (42) as cutting member (900) is pivoted between the open position and the closed position. Thus, cutting member (900) may be pivoted relative to shaft assembly (30) such that blade (904) slides relative to end effector (40), with sharp edge (906) slicing tissue through a shearing action. It should be understood that blade (904) may cooperate with an outer edge of ultrasonic blade (42) to shear the tissue. It should also be understood that cutting member (900) may be actuated independently relative to clamp arm assembly (50).

Figure 46A:
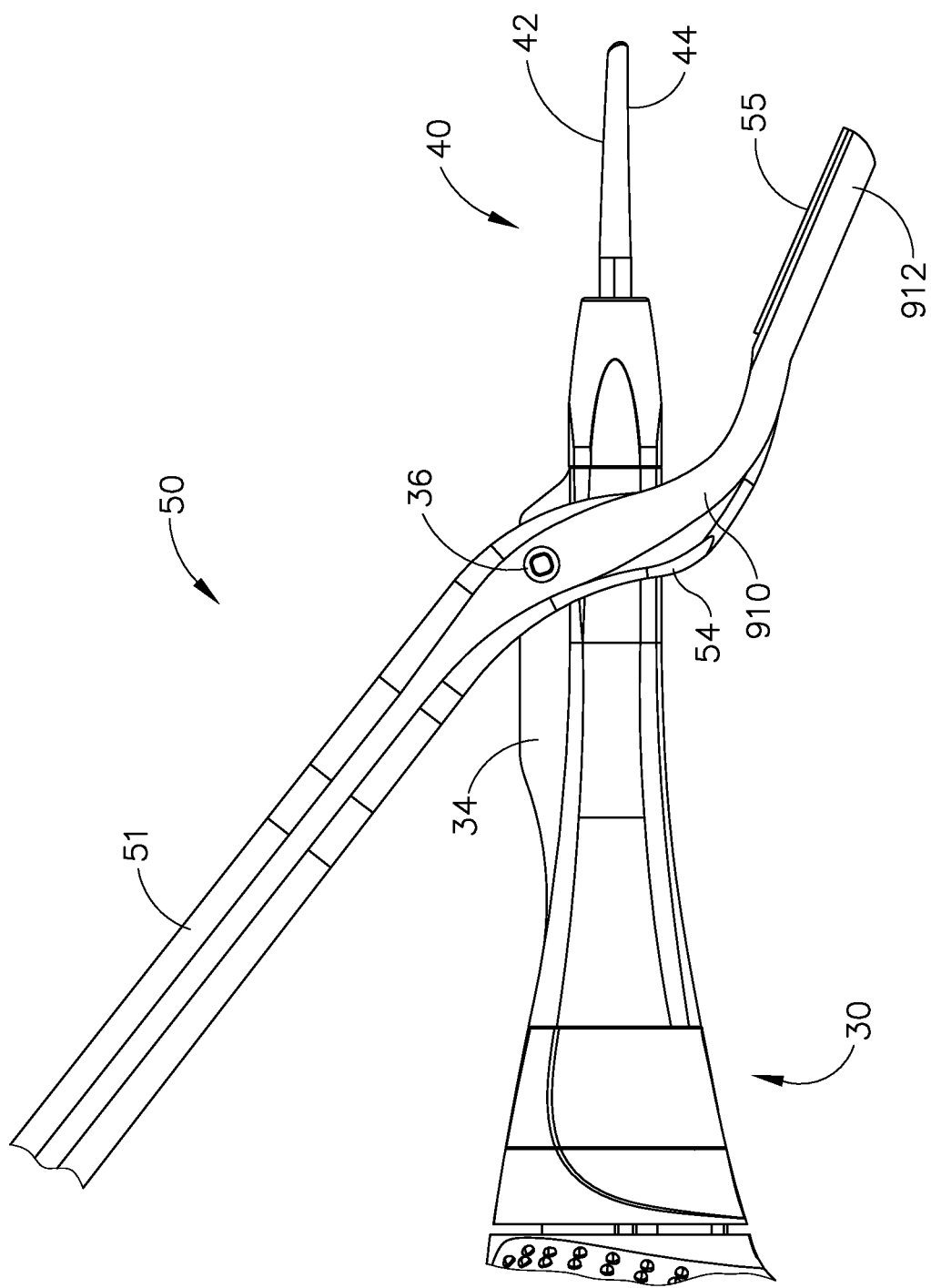
FIG. 46A depicts a side elevational view of another exemplary alternative version of the distal end of the instrument of FIG. 1, with the clamp arm in an open position.
Figure 46B:
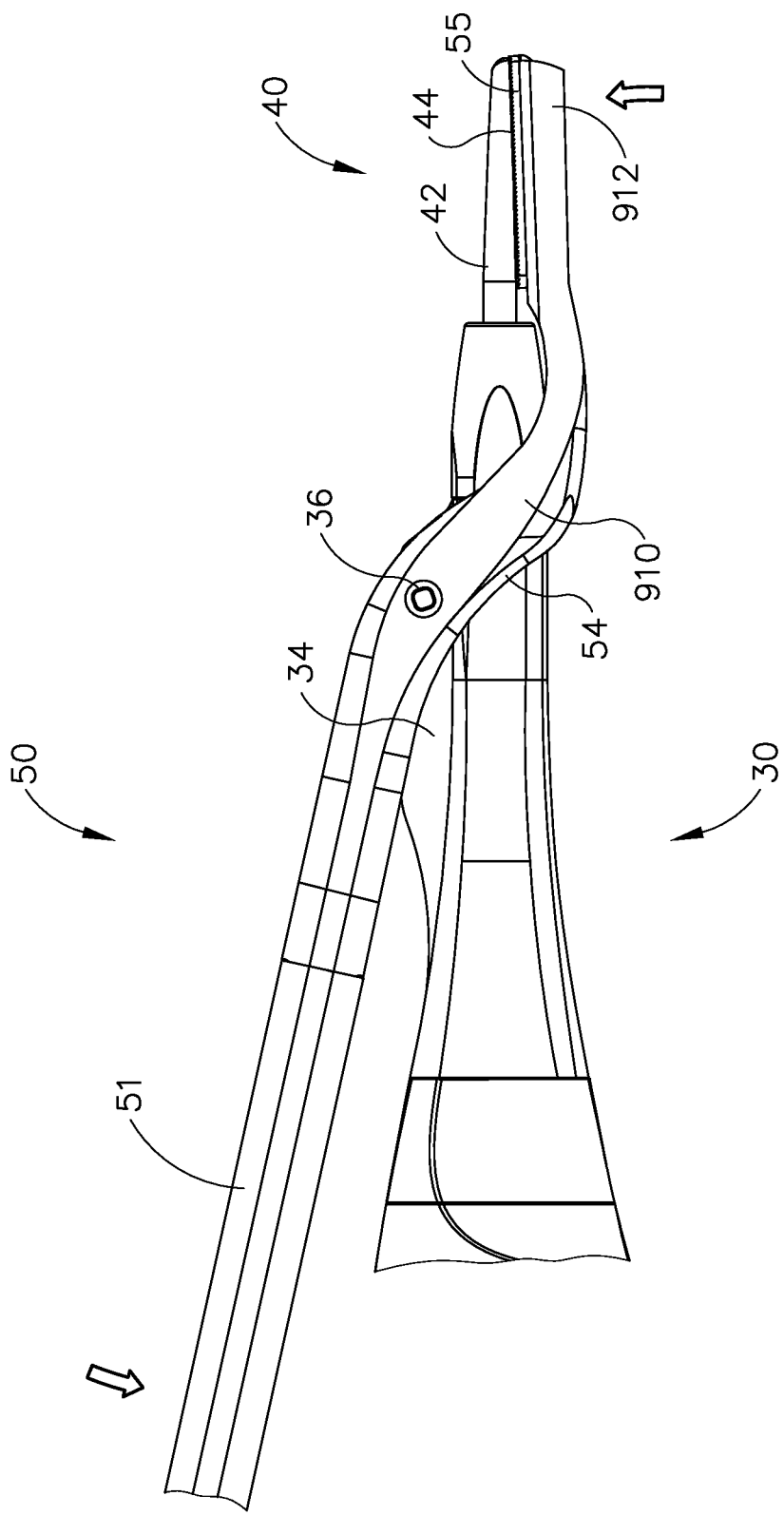
FIG. 46B depicts a side elevational view of the distal end configuration of FIG. 46A, with the clamp arm and cutting member in a first closed position.

FIGS. 46A-46B shows an exemplary alternative cutting member (910). Cutting member (910) is configured to operate substantially similar to cutting member (900) in that cutting member (910) is operable to shear tissue clamped between clamp pad (55) of clamp arm (54) and ultrasonic blade (42). A portion of cutting member (910) proximal of pivot member (36) is fixedly secured to a lateral side of clamp arm assembly (50) whereas a portion of cutting member (910) distal of pivot member (36) is not secured to the side of clamp arm assembly (50). Cutting member (910) has greater stiffness than shank portion (51) of clamp arm assembly (50). For instance, cutting member (910) may be formed of metal while shank portion (51) of clamp arm assembly (50) is formed of plastic.

Figure 46C:
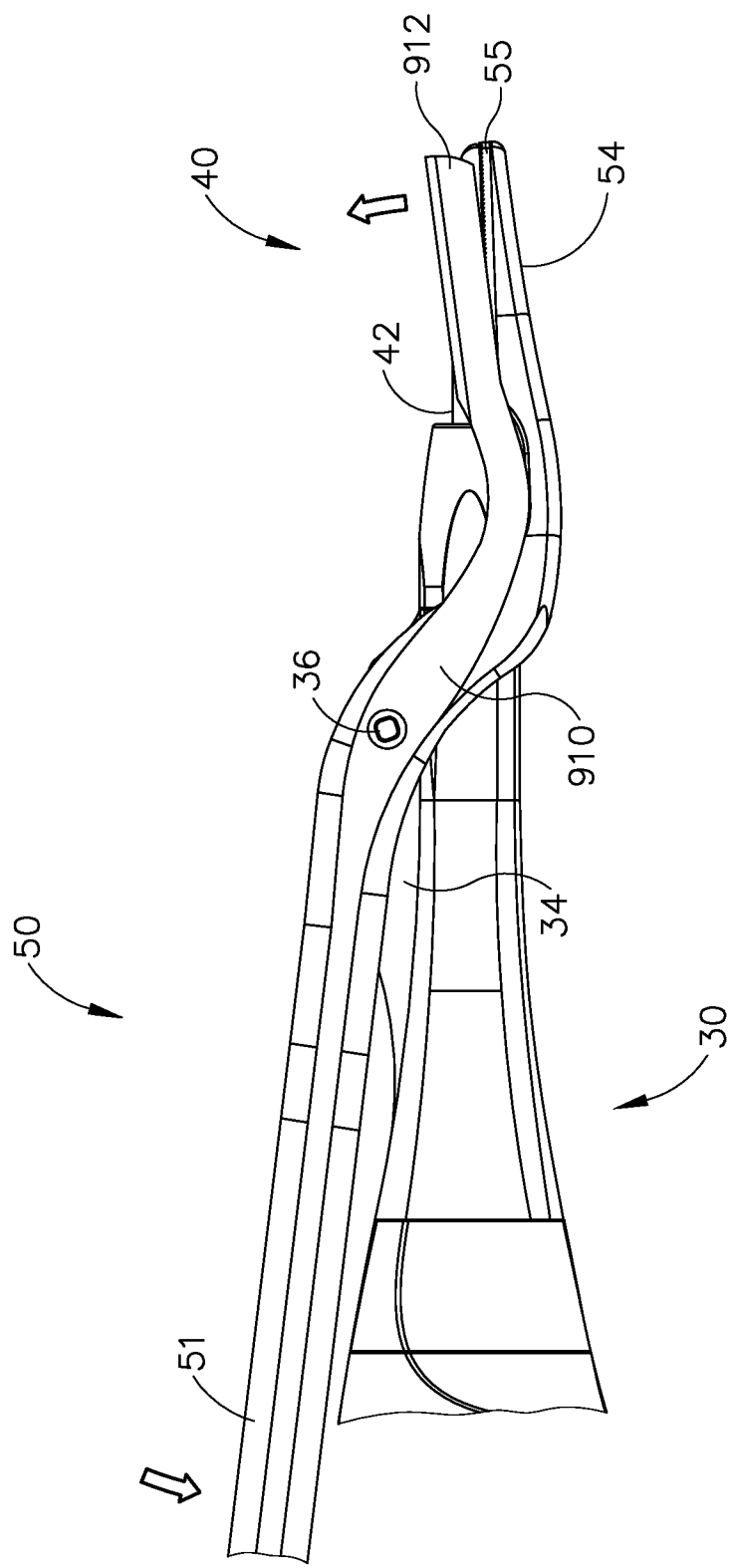
FIG. 46C depicts a side elevational view of the distal end configuration of FIG. 46A, with the clamp arm and cutting member in a second closed position.

In an open position as shown in FIG. 46A, cutting member (910) is positioned such that cutting member (910) does not cut tissue positioned between clamp pad (55) of clamp arm (54) and ultrasonic blade (42). In a first closed position shown in FIG. 46B, clamp pad (55) of clamp arm (54) is configured to engage and compress tissue between flat surface (44) of blade (42). In this first closed position, cutting member (910) still does not cut tissue positioned between clamp pad (55) of clamp arm (54) and ultrasonic blade (42). As the operator continues to drive clamp arm assembly (50) to a second closed position as shown in FIG. 46C, clamp pad (55) of clamp arm (54) continues to compress tissue against blade (42) and shank portion (51) of clamp arm assembly (50) begins to deform. Since cutting member (910) has a greater stiffness, cutting member (910) begins to pivot about pivot member (36) and relative to shank portion (51), such that blade (912) slices tissue clamped between clamp pad (55) of clamp arm (54) and ultrasonic blade (42). It should be understood that blade (912) may cooperate with an outer edge of ultrasonic blade (42) to shear the tissue. When the operator releases rings (24, 52) and returns end effector (40) to the open configuration, the resilient bias of shank portion (51) will drive cutting member (910) back to the position shown in FIG. 46A.

VI. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:

1. An ultrasonic instrument comprising:
    (a) a body;
    (b) a shaft assembly extending distally from the body;
    (c) an ultrasonic blade positioned distal to the shaft assembly;
    (d) a pivoting member comprising a clamp arm, wherein the pivoting member is pivotably coupled with the shaft assembly about a pivot axis, wherein the clamp arm is pivotable with respect to the ultrasonic blade from an open position to a closed position to thereby clamp tissue between the pivoting member and the ultrasonic blade; and
    (e) a guide feature comprising a tapered projection configured to laterally align the clamp arm relative to the ultrasonic blade as the clamp arm is pivoted toward the ultrasonic blade; wherein the tapered projection is configured to laterally align the clamp arm relative to the ultrasonic blade with a progressively increasing force as the clamp arm is pivoted toward the ultrasonic blade.

2. The ultrasonic instrument of claim 1, wherein the tapered projection extends from the shaft assembly.

3. The ultrasonic instrument of claim 1, wherein the pivoting member defines a slot dimensioned to receive the tapered projection.

4. The ultrasonic instrument of claim 3, wherein the slot comprises a consistent lateral width.

5. The ultrasonic instrument of claim 4, wherein a top portion of the tapered projection is dimensioned to fit within the consistent lateral width.

6. The ultrasonic instrument of claim 5, wherein a bottom portion of the tapered projection is not dimensioned to fit within the consistent lateral width.

7. The ultrasonic instrument of claim 1, wherein a portion of the tapered projection is longitudinally aligned with the pivot axis.

8. The ultrasonic instrument of 21, wherein the pivoting member comprises a proximal thumb ring.

9. The ultrasonic instrument of claim 1, wherein the body comprises a proximal finger ring.

10. The ultrasonic instrument of claim 1, wherein the clamp arm comprises a clamp pad.

11. The ultrasonic instrument of claim 1, wherein the body comprises an activation button.

12. The ultrasonic instrument of claim 11, wherein the body comprises a second activation button.

13. The ultrasonic instrument of claim 1, wherein the pivot axis comprises a pin extending through the pivoting member and the shaft assembly.

* * * * *